United States Patent
Chee et al.

(10) Patent No.: US 9,868,979 B2
(45) Date of Patent: Jan. 16, 2018

(54) SPATIALLY ENCODED BIOLOGICAL ASSAYS USING A MICROFLUIDIC DEVICE

(71) Applicant: Prognosys Biosciences, Inc., San Diego, CA (US)

(72) Inventors: Mark S. Chee, San Diego, CA (US); David A. Routenberg, San Diego, CA (US)

(73) Assignee: PROGNOSYS BIOSCIENCES, INC., San Diego, CA (US)

( * ) Notice: Subject to any disclaimer, the term of this patent is extended or adjusted under 35 U.S.C. 154(b) by 0 days.

(21) Appl. No.: 14/900,602

(22) PCT Filed: Jun. 25, 2014

(86) PCT No.: PCT/US2014/044191
§ 371 (c)(1),
(2) Date: Dec. 21, 2015

(87) PCT Pub. No.: WO2014/210223
PCT Pub. Date: Dec. 31, 2014

(65) Prior Publication Data
US 2016/0145677 A1    May 26, 2016

Related U.S. Application Data

(60) Provisional application No. 61/839,320, filed on Jun. 25, 2013, provisional application No. 61/839,313, filed on Jun. 25, 2013.

(51) Int. Cl.
*C12Q 1/68* (2006.01)
*B01L 3/00* (2006.01)

(52) U.S. Cl.
CPC .......... *C12Q 1/6809* (2013.01); *B01L 3/5027* (2013.01)

(58) Field of Classification Search
CPC ......... C12Q 1/68; C07H 21/04; B01L 3/5027; C40B 30/04
See application file for complete search history.

(56) References Cited

U.S. PATENT DOCUMENTS

| 5,002,882 A | 3/1991 | Lunnen et al. |
| 5,512,439 A | 4/1996 | Hornes et al. |

(Continued)

FOREIGN PATENT DOCUMENTS

| EP | 1712623 | 10/2006 |
| JP | 2011-182702 | 6/2011 |

(Continued)

OTHER PUBLICATIONS

Office Action for U.S. Appl. No. 13/266,568, dated Mar. 29, 2013.
(Continued)

*Primary Examiner* — Narayan Bhat
(74) *Attorney, Agent, or Firm* — Morrison & Foerster LLP

(57) ABSTRACT

The present disclosure provides methods and assay systems for use in spatially encoded biological assays, including assays to determine a spatial pattern of abundance, expression, and/or activity of one or more biological targets across multiple sites in a sample. In particular, the present disclosure provides methods and assay systems capable of high levels of multiplexing where reagents are provided to a biological sample in order to address tag the sites to which reagents are delivered; instrumentation capable of controlled delivery of reagents, in particular, microfluidic device based instrumentation; and a decoding scheme providing a readout that is digital in nature.

43 Claims, 22 Drawing Sheets

(56) References Cited

U.S. PATENT DOCUMENTS

| | | | |
|---|---|---|---|
| 6,210,894 B1 | 4/2001 | Brennan | |
| 6,258,558 B1 | 7/2001 | Szostak et al. | |
| 6,261,804 B1 | 7/2001 | Szostak et al. | |
| 6,281,804 B1 | 8/2001 | Haller et al. | |
| 6,344,316 B1 | 2/2002 | Lockhart et al. | |
| 6,416,950 B1 | 7/2002 | Lohse et al. | |
| 6,485,982 B1 | 11/2002 | Charlton | |
| 6,518,018 B1 | 2/2003 | Szostak et al. | |
| 6,579,695 B1 | 6/2003 | Lambalot et al. | |
| 6,632,641 B1 | 10/2003 | Brennan et al. | |
| 6,800,453 B2 | 10/2004 | LaBaer et al. | |
| 6,878,515 B1 | 4/2005 | Landegren et al. | |
| 7,118,883 B2 | 10/2006 | Inoue et al. | |
| 7,192,735 B2 | 3/2007 | Lambalot et al. | |
| 7,229,769 B2 | 6/2007 | Kozlov et al. | |
| 7,270,950 B2 | 9/2007 | Szostak et al. | |
| 7,378,242 B2 | 5/2008 | Hurt et al. | |
| 7,393,665 B2 | 7/2008 | Brenner | |
| 7,407,757 B2 | 8/2008 | Brenner | |
| 7,537,897 B2 | 5/2009 | Brenner | |
| 7,544,473 B2 | 6/2009 | Brenner | |
| 7,579,153 B2 | 8/2009 | Brenner | |
| 7,635,566 B2 | 12/2009 | Brenner | |
| 7,666,612 B2 | 2/2010 | Johnsson et al. | |
| 7,674,752 B2 | 3/2010 | He et al. | |
| 7,776,547 B2 * | 8/2010 | Roth | G01N 33/54366 435/7.1 |
| 7,858,321 B2 | 12/2010 | Glezer et al. | |
| 8,207,093 B2 | 6/2012 | Szostak et al. | |
| 8,337,851 B2 | 12/2012 | Aukerman | |
| 8,343,500 B2 | 1/2013 | Wraith | |
| 9,085,798 B2 | 7/2015 | Chee | |
| 2003/0087232 A1 | 5/2003 | Christians et al. | |
| 2003/0096323 A1 | 5/2003 | James | |
| 2003/0113713 A1 | 6/2003 | Glezer et al. | |
| 2003/0232382 A1 | 6/2003 | Brennan et al. | |
| 2003/0138879 A1 | 7/2003 | Lambalot et al. | |
| 2003/0162216 A1 | 8/2003 | Gold et al. | |
| 2003/0224419 A1 | 12/2003 | Corcoran et al. | |
| 2003/0235852 A1 | 12/2003 | Roberts et al. | |
| 2004/0112442 A1 * | 6/2004 | Maerkl | B01L 3/502738 137/597 |
| 2005/0003431 A1 | 1/2005 | Wucherpfennig | |
| 2005/0026188 A1 | 2/2005 | Van Kessel et al. | |
| 2005/0048580 A1 | 3/2005 | LaBaer et al. | |
| 2005/0164292 A1 | 7/2005 | Faroqui et al. | |
| 2005/0255548 A1 | 11/2005 | Lipovsek et al. | |
| 2005/0260653 A1 | 11/2005 | LaBaer et al. | |
| 2006/0003394 A1 | 1/2006 | Song et al. | |
| 2006/0046313 A1 | 3/2006 | Roth et al. | |
| 2006/0134669 A1 | 6/2006 | Casasanta, III | |
| 2006/0199207 A1 | 9/2006 | Matysiak | |
| 2006/0216721 A1 | 9/2006 | Kozlov et al. | |
| 2006/0216775 A1 | 9/2006 | Burkhart et al. | |
| 2006/0228758 A1 | 10/2006 | Muchhal | |
| 2006/0275799 A1 | 12/2006 | Banerjee et al. | |
| 2007/0014810 A1 | 1/2007 | Baker et al. | |
| 2007/0020625 A1 | 1/2007 | Duchaud et al. | |
| 2007/0020669 A1 | 1/2007 | Olof | |
| 2007/0026430 A1 | 2/2007 | Andersen et al. | |
| 2007/0172873 A1 | 7/2007 | Brenner et al. | |
| 2008/0071071 A1 | 3/2008 | LaBaer et al. | |
| 2008/0108804 A1 | 5/2008 | Hayashizaki et al. | |
| 2008/0220981 A1 | 9/2008 | McGregor | |
| 2008/0293591 A1 | 11/2008 | Taussig et al. | |
| 2008/0312103 A1 | 12/2008 | Nemoto et al. | |
| 2009/0280487 A1 | 11/2009 | Hung et al. | |
| 2009/0291854 A1 | 11/2009 | Weisinger-Mayr et al. | |
| 2010/0069263 A1 | 3/2010 | Shendure et al. | |
| 2010/0099103 A1 | 4/2010 | Hsieh et al. | |
| 2010/0113302 A1 | 6/2010 | Williams | |
| 2010/0159446 A1 | 6/2010 | Haff | |
| 2010/0173384 A1 | 7/2010 | Johnsson et al. | |
| 2010/0184614 A1 | 7/2010 | Ye et al. | |
| 2011/0245101 A1 | 10/2011 | Chee et al. | |
| 2011/0245111 A1 * | 10/2011 | Chee | C12Q 1/6837 506/35 |
| 2012/0065081 A1 | 3/2012 | Chee | |
| 2012/0129248 A1 | 5/2012 | Chee | |
| 2012/0195810 A1 | 8/2012 | Cohen | |
| 2012/0258871 A1 | 10/2012 | Kozlov et al. | |
| 2012/0270748 A1 | 10/2012 | Chee et al. | |
| 2013/0096033 A1 | 4/2013 | Routenberg | |
| 2013/0109595 A1 | 5/2013 | Routenberg | |
| 2013/0296174 A1 | 11/2013 | Peumans | |
| 2015/0087027 A1 * | 3/2015 | Makarov | C12P 19/34 435/91.3 |
| 2016/0024576 A1 | 1/2016 | Chee | |
| 2016/0333403 A1 | 11/2016 | Chee | |
| 2017/0058339 A1 | 3/2017 | Chee | |
| 2017/0058340 A1 | 3/2017 | Chee | |
| 2017/0058345 A1 | 3/2017 | Chee | |
| 2017/0088881 A1 | 3/2017 | Chee | |

FOREIGN PATENT DOCUMENTS

| | | |
|---|---|---|
| WO | WO 2003/010176 | 2/2003 |
| WO | WO 2004/028955 | 4/2004 |
| WO | WO 2005/026387 | 3/2005 |
| WO | WO 2006/117541 | * 11/2006 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/145612 | 12/2007 |
| WO | WO 2009/032167 | 3/2009 |
| WO | WO 2010/019826 | 2/2010 |
| WO | WO 2010/027870 | 3/2010 |
| WO | WO 2010/127186 | 11/2010 |
| WO | WO 2011/014879 | 2/2011 |
| WO | WO 2011/071943 | 6/2011 |
| WO | WO 2011/127006 | 10/2011 |
| WO | WO 2011/127099 | 10/2011 |
| WO | WO 2012/022975 | 2/2012 |
| WO | WO 2012/071428 | 5/2012 |
| WO | WO 2012/139110 | 10/2012 |
| WO | WO/2014/210223 | 12/2014 |
| WO | WO/2014/210225 | 12/2014 |

OTHER PUBLICATIONS

Response to Office Action for U.S. Appl. No. 13/266,568, filed Aug. 29, 2013.
Final Office Action for U.S. Appl. No. 13/266,568, dated Dec. 5, 2013.
Response After Final Office Action for U.S. Appl. No. 13/266,568, filed Mar. 4, 2014.
Office Action for U.S. Appl. No. 13/266,568, dated Mar. 26, 2013.
Response to Office Action for U.S. Appl. No. 13/266,568, filed Jun. 26, 2014.
Non-final Office Action in U.S. Appl. No. 14/723,332, dated Feb. 23, 2016.
Final Office Action in U.S. Appl. No. 14/723,332, dated Nov. 29, 2016.
Non-final Office Action in U.S. Appl. No. 14/723,332, dated Mar. 28, 2017.
Non-final Office Action in U.S. Appl. No. 15/224,253, dated Dec. 9, 2016.
Non-final Office Action in U.S. Appl. No. 15/224,253, dated May 18, 2017.
Final Office Action in U.S. Appl. No. 15/224,253, dated Jul. 3, 2017.
Office Action for U.S. Appl. No. 13/388,229, dated Dec. 24, 2012.
International Search Report and Written Opinion for PCT/US2010/033064, dated Jul. 30, 2010.
International Preliminary Report on Patentability Chapter I for PCT/US2010/033064, dated Nov. 1, 2011.
International Search Report and Written Opinion for PCT/US2010/044134, dated Mar. 18, 2011.
International Preliminary Report on Patentability Chapter I for PCT/US2010/044134, dated Jan. 31, 2012.

(56) References Cited

OTHER PUBLICATIONS

Patent Examination Report No. 1 for AU 2010278710, dated Feb. 11, 2014.
Communication Pursuant to Art. 94(3) EPC for EP 10747097.3-1405, dated Jul. 26, 2013.
Restriction Requirement for U.S. Appl. No. 13/514,045, dated Nov. 23, 2012.
Response to Restriction Requirement for U.S. Appl. No. 13/514,045, filed Dec. 19, 2012.
Office Action for U.S. Appl. No. 13/514,045, dated Feb. 21, 2013.
Response to Office Action for U.S. Appl. No. 13/514,045, filed Jun. 17, 2013.
Response to Office Action for U.S. Appl. No. 13/514,045, filed Jun. 27, 2013.
Final Office Action for U.S. Appl. No. 13/514,045, dated Oct. 18, 2013.
International Search Report and Written Opinion for PCT/US2010/059327, dated Mar. 29, 2011.
International Preliminary Report on Patentability Chapter I for PCT/US2010/059327, dated Jun. 12, 2012.
Patent Examination Report No. 1 for AU 2010328226, dated May 9, 2013.
First Office Action for CN 201080055351.2, dated Jul. 23, 2013.
Supplemental European Search Report for EP 10836568.5-1403, dated Feb. 13, 2013.
Response to Supplemental European Search Report for EP 10836568.5-1403, filed Sep. 10, 2013.
Communication Pursuant to Art. 94(3) EPC for EP 10836568.5-1403, dated Mar. 12, 2014.
First Examination Report for EP 10836568.5-1403, dated Oct. 1, 2013.
Response to First Examination Report for EP 10836568.5-1403, filed Feb. 17, 2014.
Response to Examination Report for EP 10836568.5-1403, dated Jul. 10, 2014.
Restriction Requirement for U.S. Appl. No. 13/080,616, dated Dec. 17, 2013.
Response to Restriction Requirement for U.S. Appl. No. 13/080,616, filed Jan. 16, 2014.
Office Action for U.S. Appl. No. 13/080,616, dated Apr. 9, 2014.
Response to Office Action for U.S. Appl. No. 13/080,616, filed Aug. 11, 2014.
Final Office Action for U.S. Appl. No. 13/080,616, dated Oct. 21, 2014.
Response to final Office Action for U.S. Appl. No. 13/080,616, filed Feb. 23, 2015.
Advisory Action for U.S. Appl. No. 13/080,616, dated Mar. 17, 2015.
International Search Report and Written Opinion for PCT/US2011/031308, dated Jun. 7, 2011.
International Preliminary Report on Patentability Chapter I for PCT/US2011/031308, dated Oct. 9, 2012.
Patent Examination Report No. 1 for AU 2011237729, dated Jul. 9, 2013.
Response to Patent Examination Report No. 1 for AU 2011237729, filed Mar. 3, 2014.
Patent Examination Report No. 1 for AU 2014203638, dated Oct. 1, 2015.
Office Action for CA 2794522, dated May 22, 2014.
Response to Office Action for CA 2794522, dated Sep. 17, 2014.
Voluntary Amendment and Observation for CN 201180017696.3, filed Jul. 25, 2013.
First Examination Report for CN 201180017696.3, dated Oct. 18, 2013.
Second Examination Report for CN 201180017696.3, dated Jul. 3, 2014.
Response to First Examination Report for CN 201180017696.3, filed Mar. 3, 2014.
Response to Second Examination Report for CN 201180017696.3, filed Sep. 17, 2014.
Third Examination Report for CN 201180017696.3, dated Jan. 27, 2015.
Response to Third Examination Report for CN 201180017696.3, filed Apr. 13, 2015.
Rule 161/162 Communication for EP 11766613.1, dated Nov. 14, 2012.
Response to Rule 161/162 Communication for EP 11766613.1, filed May 17, 2013.
European Search Report for EP 11766613.1, dated Jan. 15, 2014.
Response to European Search Report for EP 11766613.1, filed Jul. 11, 2014.
European Examination Report for EP 11766613.1, dated Aug. 22, 2014.
Response to European Examination Report for EP 11766613.1, filed Jan. 8, 2015.
Office Action for U.S. Appl. No. 13/079,878, dated Aug. 13, 2012.
International Search Report and Written Opinion for PCT/US2011/031163, dated May 23, 2011.
International Preliminary Report on Patentability Chapter I for PCT/US2011/031163, dated Oct. 9, 2012.
Restriction Requirement for U.S. Appl. No. 13/442,637, dated May 17, 2012.
Response to Restriction Requirement for U.S. Appl. No. 13/442,637, filed Jun. 5, 2012.
Supplemental Response and Amendment for U.S. Appl. No. 13/442,637, filed Jun. 6, 2012.
Office Action for U.S. Appl. No. 13/442,637, dated Aug. 9, 2012.
Response to Office Action for U.S. Appl. No. 13/442,637, filed Oct. 9, 2012.
Final Office Action for U.S. Appl. No. 13/442,637, dated Dec. 20, 2012.
Response to Final Office Action for U.S. Appl. No. 13/442,637, filed Mar. 20, 2013.
Advisory Action for U.S. Appl. No. 13/442,637, dated Apr. 1, 2013.
Preliminary Amendment and remarks with filing of RCE for U.S. Appl. No. 13/442,637, filed Apr. 17, 2013.
Office Action for U.S. Appl. No. 13/442,637, dated Jan. 22, 2015.
Office Action for U.S. Appl. No. 13/442,637, dated Oct. 8, 2015.
Preliminary Amendment for U.S. Appl. No. 14/068,921, filed Nov. 22, 2013.
Non-final Office Action in U.S. Appl. No. 14/068,921, dated Jun. 29, 2015.
Final Office Action in U.S. Appl. No. 14/068,921, dated Mar. 1, 2016.
Non-final Office Action in U.S. Appl. No. 14/068,921, dated May 8, 2017.
International Search Report and Written Opinion for PCT/US20120/032759, dated Sep. 28, 2012.
International Preliminary Report on Patentability Chapter I for PCT/US2012/032759, dated Oct. 8, 2013.
Invitation to Pay Additional Fees and, Where Applicable, Protest Fee for PCT/US2012/032759, dated Jul. 16, 2012.
Extended European Search Report for EP 12767937.1-1403, dated Nov. 18, 2014.
Extended European Search Report for EP 16183356.1, dated Apr. 24, 2017.
International Search Report and Written Opinion of PCT/US14/29691, dated Aug. 19, 2014.
Restriction Requirement in U.S. Appl. No. 14/776,537, dated Jan. 6, 2017.
Non-final Office Action in U.S. Appl. No. 14/776,537, dated May 2, 2017.
First Examination Report in CN 201480028069.3, dated Aug. 26, 2016 (Including English translation).
Second Examination Report in CN 201480028069.3, dated Jul. 10, 2017 (Including English translation).
Extended European Search Report for EP 14765026.1, dated Sep. 26, 2016.
International Search Report and Written Opinion of PCT/US14/44191, dated Nov. 7, 2014.
Extended European Search Report for EP 14816674.7, dated Feb. 3, 2017.

(56) References Cited

OTHER PUBLICATIONS

International Search Report and Written Opinion of PCT/US14/44196, dated Nov. 7, 2014.
Non-final Office Action in U.S. Appl. No. 14/900,604, dated Feb. 7, 2017.
Extended European Search Report for EP 14818012.8, dated Feb. 3, 2017.
International Search Report and Written Opinion of PCT/US14/64588, dated Mar. 11, 2015.
Non-final Office Action in U.S. Appl. No. 15/035,206, dated Jun. 30, 2017.
Valencia et al., "mRNA-display-based selections for proteins with desired functions: A protease-substrate case study," Biotechnology Progress, 2008, 24(3): 561-569.
Anderson et al., "Microarrayed Compound Screening to Identify Activators and Inhibitors of AMP-Activated Protein Kinase," J. of Biomolecular Screening (2004) 9:112 POI: 0.1177/1087057103260592.
Angenendt et al., "Cell-free expression and functional assay in a nanowell chip format," Analytical Chemistry (2004) 76(7):1844-49.
Angenendt et al., "Generation of High Density Protein Microarrays by Cell-free in Situ Expression of Unpurified PCR Products," Molecular and Cellular Proteomics (2006) Ch. 5.9, pp. 1658-1666.
Atkinson, Overview of Translation: Lecture Manuscript, U of Texas (2000) pp. 6.1-6.8.
Blokzijl et al., "Profiling protein expression and interactions: proximity ligation as a tool for personalized medicine," J Intern Med (2010) 268:232-245.
Burns et al., "Well-less, gel-permeation formats for ultra-HTS," DDT (2001) 6(12):S40-S47.
Carlson et al., "Formylglycine-generating Enzyme," J. of Biological Chemistry (2008) 283(29):20117-125.
Cerutti et al., "Generation of sequence-specific, high affinity anti-DNA antibodies," Journal of Biological Chemistry (2001) 276(16):12769-12773.
Cha et al., "Specificity, Efficiency and Fidelity of PCR," Genome Res. (1993) 3:518-29.
Chandra et al., "Cell-free synthesis-based protein microarrays and their applications," Proteomics ePub (2009) 5(6):717-30.
Chatterjee et al., "Protein Microarray On-Demand: A Novel Protein Microarray System," PLos One (2008) 3(9):e3265.
Chen et al., "DNA hybridization detection in a microfluidic Channel using two fluorescently labelled nucleic acid probes", Biosensors and Bioelectronics (2008) 23:1878-1882.
Cheng et al., "Sensitive Detection of Small Molecules by Competitive Immunomagnetic-Proximity Ligation Assay," Anal Chem (2012) 84:2129-2132.
Condina et al., "A sensitive magnetic bead method for the detection and identification of tyrosine phosphorylation in proteins by MALDI-TOF/TOF MS," Proteomics (2009) 9:3047-3057.
Cujec et al. "Selection of v-abl tyrosine kinase substate sequences from randomnized peptide and cellular proteomic libraries using mRNA display," Chemistry and Biology (2002) 9:253-264.
Darmanis, et al.,"ProteinSeq: High-Performance Proteomic Analyses by Proximity, Ligation and Next Generation Sequencing", PLos One (2011) 6(9):e25583 doi1 0.1371/journal.pone.0025583 20 1.
Eldridge et al. "An in vitro selection strategy for conferring protease resistance to ligand binding peptides," Protein Eng Des Sel (2009) 22(11):691-698.
Ellington et al., "Antibody-based protein multiplex platforms: technical and operational challenges," Clin Chem (2010) 56(2):186-193.
Flanigon et al., "Multiplex protein detection with DNA readout via mass spectrometry," N Biotechnol (2013) 30(2):153-158.
Fredriksson et al., "Protein detection using proximity-dependent DNA ligation assays," Nature Biotech. (2002) 20:473-77.
Fredriksson et al., "Multiplexed protein detection by proximity ligation for cancer detection," Nature Methods (2007) 4(4):327-29.
Fredriksson et al., "Multiplexed proximity ligation assays to profile putative plasma biomarkers relevant to pancreatic and ovarian cancer," Clin. Chem. (2008) 5(3): 582-89.
Frese et al., "Formylglycine Aldehyde Tag-Protein Engineering through a Novel Post-translational Modification," ChemBioChem (2009) 10:425-27.
Fu et al., "Counting individual DNA molecules by the stochastic attachment of diverse labels," PNAS (2011) 108:9026-9031.
Gu et al., "Protein tag-mediated conjugation of oligonucleotides to recombinant affinity binders for proximity ligation," N Biotechnol (2013) 30(2):144-152.
Hammond et al., "Profiling cellular protein complexes by proximity ligation with dual tag microarray readout," (2012) 7(7):e40405.
He et al., "In situ synthesis of protein arrays," Current Opinion in Biotechnology (2008) 19:4-9.
He et al., "In situ synthesis of protein arrays," Current Opinion in Biotechnology (2008)19:4-9 Supplementary figures.
He, "Cell-free protein synthesis: applications in proteomics and biotechnology," (2008) New Biotechnology 25:126-132.
He et al., "Printing protein arrays from DNA arrays," Nature Methods (2008) 5:175-77.
Hedskog et al., "Dynamics of HIV-1 Quasispecies during Antiviral Treatment Dissected using Ultra-Deep Pyrosequencing," PLoS One (2010) 5(7):e11345.
Hendrickson et al., "High sensitivity multianalyte immunoassay using covalent DNA-labeled antibodies and polymerase chain reaction," Nucl. Acid Res. (1995) 23(9):522-29.
Hiatt et al., "Parallel, tag-directed assembly of locally-derived short sequence reads," Nature Methods (2010) 7(2):119-25.
Mir et al., "Sequencing by cyclic ligation and cleavage (CycLiC) directly on a microarray captured template," Nucleic Acids Research (2009) 37(1):e5-1.
Kozlov et al., "A Method for Rapid Protease Substrate Evaluation and Optimization," Comb. Chem. and High Throughput (2006) 9:481-87.
Kozlov et al., "A High-Complexity Multiplexed Solution-Phase Assay for Profiling Protease Activity on Microarrays," Comb. Chem. and High Throughput (2008) 11:24-35.
Kozlov et al., "A Highly Scalable Peptide-Based Assay System for Proteomics," PLoS One (2012) 7(6):e37441.
Kurz et al., "cDNA-Protein Fusions: Covalent Protein-Gene Conjugates for the In Vitro Selection of Peptides and Proteins," ChemBioChem (2001) 2:666-72.
Larman et al., "Autoantigen discovery with a synthetic human peptidome", Nature Biotechnology (2011) doi:1 0.1038/nbt.1856.
Lundberg et al., "Multiplexed homogeneous proximity ligation assays for high-throughput protein biomarker research in serological material," Mol Cell Proteomics (2011) 10(4):M110.004978.
Lundberg et al., "Homogeneous antibody-based proximity extension assays provide sensitive and specific detection of low-abundant proteins in human blood", Nucleic Acids Res.(2011) 39(15):e1 02 (Abstract).
Mizusawa et al., "A bacteriophage lambda vector for cloning with BamHI and Sau3A," Gene (1982) 20:317-322.
Ng et al., "Massively parallel sequencing and rare disease," Human Molec. Genetics (2010) 19(2):R119-R124.
Niemeyer., "The developments of semisynthetic DNA/protein conjugates," Trends Biotechnol (2002) 20(9):395-401.
Oleinikov et al. "Self-assembling protein arrays using electronic semiconductor microchips and in vitro translation," Journal of Proteome Research (2003) 2:313-319.
Osada et al., "Epitope mapping using ribosome display in a resconstituted cell-free protein synthesis system," Journal of Biochemistry, 2009, 145(5):693-700.
O'Shannessy et al., "Detection and Quantitation of Hexa-Histidine-Tagged recombinant proteins on western blots and by a surface plasmon resonance biosensor technique," Analytical Biochemistry (1995) 229:119-124.
Proseek® Multiplex 96×96 User Manual (2013) Olink Bioscience, Uppsala, Sweden, 20 pages.
Ramachandran et al., "Next-generation high-density self-assembling functional protein arrays," Nature Methods (2008) 5(6):535-38.

(56) References Cited

OTHER PUBLICATIONS

Roberts et al., "RNA-peptide fusions for the in vitro selection of peptides and proteins," PNAS USA (1997) 94:12297-302.
Rouillard et al., "OligoArray 2.0: design of oligonucleotide probes for DNA microarrays using a thermodynamic approach," Nuc. Acid Research (2003) 31 (12):3057-62.
Rountenberg et al., "Microfluidic probe: a new tool for integrating microfluidic environments and electronic wafer-probing," Lab Chip, Oct. 29, 2009, 10: 123-127.
Rush et al., "New Aldehyde Tag Sequences Identified by Screening Formylglycine Generating Enzymes in Vitro and in Vivo," J. of American Chemical Society (2008) 130: 12240-41.
Rush et al., "New Aldehyde Tag Sequences Identified by Screening Formylglycine Generating Enzymes in Vitro and in Vivo," J. of American Chemical Society (2008) 130: 12240-41 (2008) Supplement.
Schmitt et al., "Detection of ultra-rare mutations by next-generation sequencing," PNAS (2012) 109:14508-14523.
Sergeeva et al., "Display technologies: Application for the discovery of drug and gene delivery agents," Advanced Drug Delivery Reviews (2006) 58(15):1622-1654.
Shoemaker et al., "Quantitative phenotypic analysis of yeast deletion mutants using a highly parallel molecular bar-coding strategy," Nature genetics (1996) 14:450-456.
Shults et al., "A multiplexed protein kinase assay," Chem Bio Chem (2007) 8:933-942.
Tian et al., "Antigen peptide-based immunosensors for rapid detection of antibodies and antigens," Anal Chem (2009) 81:5218-5225.
Tolbert et al., "New Methods for Proteomic Research: Preparation of Proteins with N-Terminal Cysteines for Labeling and Conjugation," Angew. Chem. Int. Ed. (2002) 41(12):2171-74.
Takahashi et al., "In Vitro Selection of Protein and Peptide Libraries Using mRNA Display," Nucleic Acid and Peptide Aptamers: Methods and Protocols (2009) 535:293-314 (Ch.17).
Vogelstein et al., "Digital PCR," PNAS USA (1999) 96:9236-41.
Waichman et al., "Functional Immobilization and Patterning of Proteins by an Enzymatic Transfer Reaction", Anal. Chem. (2010) 82:1478-85.
Weichhart et al., "Functional selection of vaccine candidate peptides from *Staphylococcus aureus* whole-genome expression libraries in vitro," Infection and Immunity, 2003, 71(8):4333-4641.
Wong et al., "Direct Site-Selective Covalent Protein Immobilization Catalyzed by a Phosphopantetheinyl Transferase," J. Am. Chem Soc. (2008) 130:12456-64.
Worthington et al., "Cloning of random oligonucleotides to create single-insert plasmid libraries," Analyt. Biochem (2001) 294:169-175.
Xiao et al., "Direct determination of haplotypes from single DNA molecules," Nature Methods (2009) 6(3):199-01.
Yin et al., "Genetically encoded short peptide tag for versatile protein labeling by Sfp phosphopantetheinyl transferase," PNAS (2005) 102(44):15815-20.
Yonezawa et al., "DNA display for in vitro selection of diverse peptide libraries", Nucleic Acids Research (2003) 31(19):e118.
Zhang et al., "Assembling DNA through Affinity Binding to Achieve Ultrasensitive Protein Detection," Angew Chem Int Ed (2013) 52:2-10.
Zhang et al., "Binding-induced DNA assembly and its application to yoctomole detection of proteins," Anal Chem (2012) 84(2):877-884.
Zhou et al., "Genetically Encoded Short Peptide Tags for Orthogonal Protein Labeling by Sfp and AcpS Phosphopentetheinyl Transferases," ACS Chemical Biology (2007) 2(5): 337-346.
Zlobec et al., "Next-generation tissue microarray (ngTMA) increases the quality of biomarker studies: an example using CD3, CD8, and CD45RO in the tumor microenvironment of six different solid tumor types," Journal of Translational Medicine (2013) 11:104.

\* cited by examiner

Figure 6
D
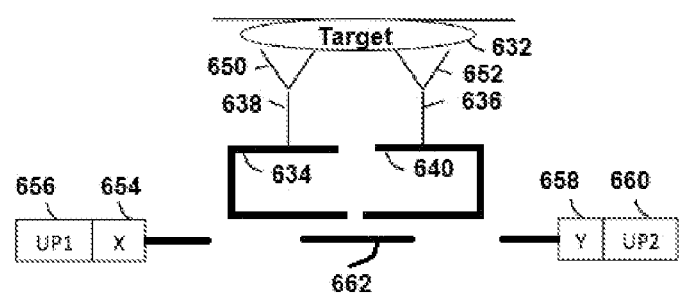
E
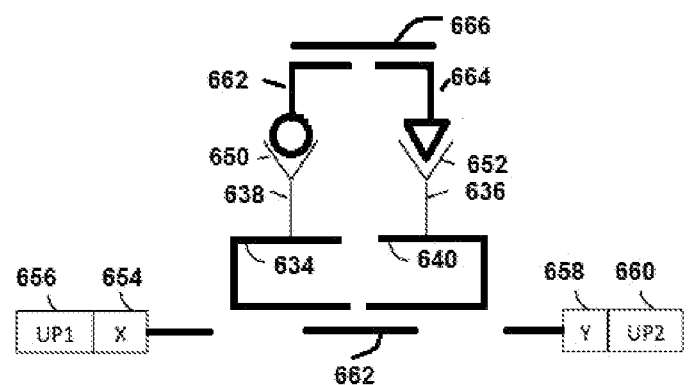

Figure 15
A
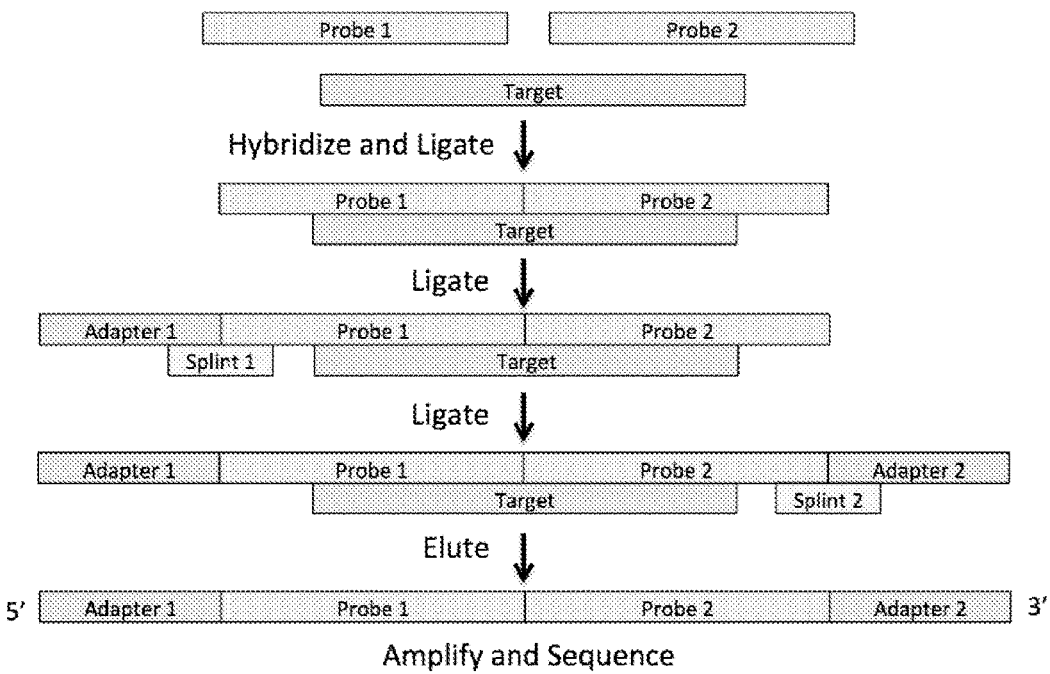
B
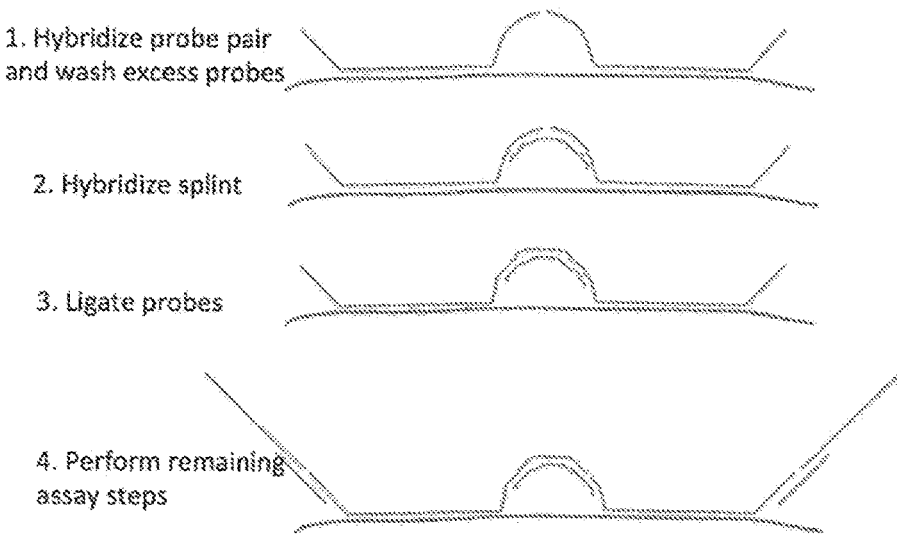

Figure 20
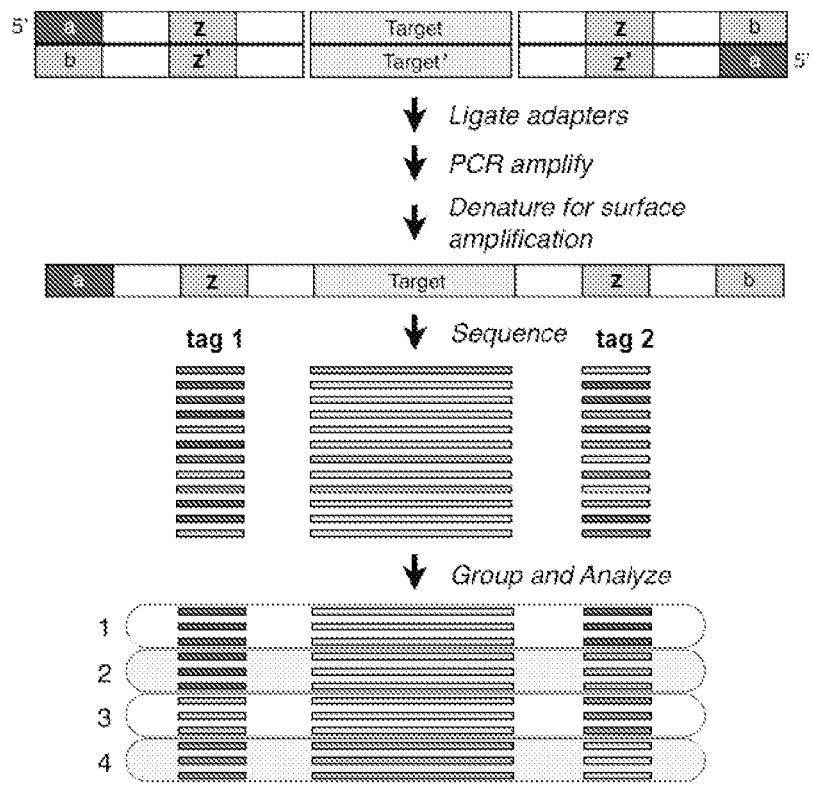
B.
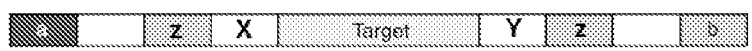
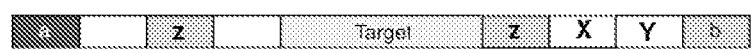

SPATIALLY ENCODED BIOLOGICAL ASSAYS USING A MICROFLUIDIC DEVICE

RELATED APPLICATIONS

This application is a national phase of International Application No. PCT/US2014/044191, filed Jun. 25, 2014, which claims benefit of priority to U.S. Provisional Patent Application Ser. No. 61/839,320, filed Jun. 25, 2013, entitled "Spatially encoded biological assays using a microfluidic device," and U.S. Provisional Patent Application Ser. No. 61/839,313, filed Jun. 25, 2013, entitled "Methods and systems for determining spatial patterns of biological targets in a sample," the disclosures of which are incorporated by reference herein in their entireties. In some embodiments, this application is related to International Application No. PCT/US2014/044196, filed Jun. 25, 2014, entitled "Methods and systems for determining spatial patterns of biological targets in a sample," the disclosure of which is incorporated by reference herein in its entirety.

STATEMENT REGARDING FEDERALLY SPONSORED RESEARCH OR DEVELOPMENT

This invention was made with the support by the Department of Health and Human Services, National Institute of General Medical Sciences Grant Number R43GM096706, and National Human Genome Research Institute Grant Number R43HG006223. The U.S. government may have certain rights in this invention.

TECHNICAL FIELD

The present disclosure generally relates to assays of biological molecules, and in particular, to methods and assay systems for determining spatial patterns of abundance, expression, and/or activity of a biological target in a sample using a microfluidic device.

BACKGROUND

In the following discussion, certain articles and methods are described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Comprehensive gene expression analysis and protein analysis have been useful tools in understanding mechanisms of biology. Use of these tools has allowed the identification of genes and proteins involved in development and in various diseases such as cancer and autoimmune disease. Conventional methods such as in situ hybridization and other multiplexed detection of different transcripts have revealed spatial patterns of gene expression and have helped shed light on the molecular basis of development and disease. Other technologies that have enabled the quantitative analysis of many RNA sequences per sample include microarrays (see Shi et al., Nature Biotechnology, 24(9): 1151-61 (2006); and Slonim and Yanai, Plos Computational Biology, 5(10):e1000543 (2009)); serial analysis of gene expression (SAGE) (see Velculescu et al., Science, 270 (5235):484-87 (1995)); high-throughput implementations of qPCR (see Spurgeon et al., Plos ONE, 3(2):e1662 (2008)); in situ PCR (see Nuovo, Genome Res., 4:151-67 (1995)); and RNA-Seq (see Mortazavi et al., Nature Methods, 5(7): 621-8 (2008)). As useful as these methods are, however, they do not enable simultaneous measurement of the expression of many genes or the presence and/or activity of multiple proteins at many spatial locations in a sample.

Laser capture microdissection has permitted the analysis of many genes at a small number of locations, but it is very expensive, laborious, and does not scale well. Certain PCR assays in a 2D format preserve spatial information (see Armani et al., Lab on a Chip, 9(24):3526-34 (2009)), but these methods have low spatial resolution because they rely on physically transferring tissues into wells, which also prevents random access to tissue samples and high levels of multiplexing.

At present, there is a need to analyze at high resolution the spatial expression patterns of large numbers of genes, proteins, or other biologically active molecules simultaneously. There is also a need for reproducible, high-resolution spatial maps of biological molecules in tissues. The present disclosure addresses these needs.

SUMMARY

In one aspect, provided herein is a method of determining a spatial pattern of abundance, expression and/or activity of a biological target in a sample, comprising:

(a) delivering a probe for a biological target to a sample, the probe comprising: (1) a binding moiety capable of binding to the biological target; and (2) an identity tag that identifies the biological target or the binding moiety;

(b) affixing the sample from step (a) to a first microfluidic device having multiple first addressing channels, wherein each first addressing channel identifies a first area in the sample;

(c) delivering a first address tag through each of the first addressing channels to each first area in the sample, wherein each first address tag is to be coupled to the probe;

(d) affixing the sample from step (c) to a second microfluidic device having multiple second addressing channels, wherein each second addressing channel identifies in the sample a second area that intersects with a first area identified by the first addressing channels at an angle greater than 0 degree;

(e) delivering a second address tag through each of the second addressing channels to each second area in the sample, wherein each second address tag is to be coupled to the probe, whereby the first address tag and the second address tag at an intersection between a first area and a second area determine the intersection's address;

(f) analyzing the probe bound to the biological target, the analysis comprising: (1) determining the abundance, expression and/or activity of the biological target by assessing the amount of the probe bound to the biological target; and (2) determining the identities of the identity tag and the first and second address tags at each address; and (g) determining a spatial pattern of the biological target abundance, expression and/or activity in the sample based on the analysis of step (f).

In another aspect, disclosed herein is a method of determining a spatial pattern of abundance, expression and/or activity of a biological target in a sample, comprising:

(a) affixing a sample to a first microfluidic device having multiple first addressing channels, wherein each first addressing channel identifies a first area in the sample;

(b) delivering a first probe for a biological target through each of the first addressing channels to each first area in the sample, the probe comprising: (1) a first binding moiety capable of binding to the biological target; (2) a first address tag that identifies an area in the sample to which the first probe is delivered; and (3) a first identity tag that identifies the biological target or the first binding moiety;

(c) affixing the sample from step (b) to a second microfluidic device having multiple second addressing channels, wherein each second addressing channel identifies in the sample a second area that intersects with a first area identified by the first addressing channels at an angle greater than 0 degree;

(d) delivering a second probe for the biological target through each of the second addressing channels to each second area in the sample, the probe comprising: (1) a second binding moiety capable of binding to the biological target; (2) a second address tag that identifies an area in the sample to which the first probe is delivered; and (3) a second identity tag that identifies the biological target or the second binding moiety, whereby the first address tag and the second address tag at an intersection between a first area and a second area determine the intersection's address;

(e) analyzing the probes bound to the biological target, the analysis comprising: (1) determining the abundance, expression and/or activity of the biological target by assessing the amount of the probes bound to the biological target; and (2) determining the identities of the first and second identity tags and the first and second address tags at each address; and (f) determining a spatial pattern of the biological target abundance, expression and/or activity in the sample based on the analysis of step (e).

In yet another aspect, provided herein is a method of determining a spatial pattern of abundance, expression and/or activity of a biological target in a sample, comprising:

(a) affixing a sample to a first microfluidic device having multiple first addressing channels, wherein each first addressing channel identifies a first area in the sample;

(b) delivering a probe for a biological target through each of the first addressing channels to each first area in the sample, the probe comprising: (1) a binding moiety capable of binding to the biological target; (2) a first address tag that identifies an area in the sample to which the probe is delivered; and (3) an identity tag that identifies the biological target or the binding moiety;

(c) affixing the sample from step (b) to a second microfluidic device having multiple second addressing channels, wherein each second addressing channel identifies in the sample a second area that intersects with a first area identified by the first addressing channels at an angle greater than 0 degree;

(d) delivering a second address tag through each of the second addressing channels to each second area in the sample, wherein each second address tag is to be coupled to the probe, whereby the first address tag and the second address tag at an intersection between a first area and a second area determine the intersection's address;

(e) analyzing the probe bound to the biological target, the analysis comprising: (1) determining the abundance, expression and/or activity of the biological target by assessing the amount of the probe bound to the biological target; and (2) determining the identities of the identity tag and the first and second address tags at each address; and (f) determining a spatial pattern of the biological target abundance, expression and/or activity in the sample based on the analysis of step (e).

In another aspect, disclosed herein is a method of determining of spatial pattern of abundance, expression and/or activity of a biological target in a sample, comprising:

(a) affixing a sample to a first microfluidic device having multiple first addressing channels, wherein each first addressing channel identifies a first area in the sample;

(b) delivering a first address tag through each of the first addressing channels to each first area in the sample;

(c) affixing the sample from step (b) to a second microfluidic device having multiple second addressing channels, wherein each second addressing channel identifies in the sample a second area that intersects with a first area identified by the first addressing channels at an angle greater than 0 degree;

(d) delivering a probe for a biological target through each of the second addressing channels to each second area in the sample, the probe comprising: (1) a binding moiety capable of binding to the biological target; (2) a second address tag that identifies an area in the sample to which the probe is delivered; and (3) an identity tag that identifies the biological target or the binding moiety, wherein each first address tag to be coupled to the probe, whereby the first address tag and the second address tag at an intersection between a first area and a second area determine the intersection's address;

(e) analyzing the probe bound to the biological target, the analysis comprising: (1) determining the abundance, expression and/or activity of the biological target by assessing the amount of the probe bound to the biological target; and (2) determining the identities of the identity tag and the first and second address tags at each address; and (f) determining a spatial pattern of the biological target abundance, expression and/or activity in the sample based on the analysis of step (e).

In one aspect, disclosed herein is a method of determining a spatial pattern of abundance, expression and/or activity of a biological target in a sample, comprising:

(a) delivering a probe for a biological target to a sample, the probe comprising a binding moiety capable of binding to the biological target, and optionally, delivering an adaptor that specifically binds to the probe, wherein the probe and/or the adaptor comprises an identity tag that identifies the biological target or target-binding moiety;

(b) affixing the sample from step (a) to a first microfluidic device having multiple first addressing channels, wherein each first addressing channel identifies a first area in the sample;

(c) delivering a first address tag through each of the first addressing channels to each first area in the sample, wherein each first address tag is to be coupled to the probe and/or the adaptor;

(d) affixing the sample from step (c) to a second microfluidic device having multiple second addressing channels, wherein each second addressing channel identifies in the sample a second area that intersects with a first area identified by the first addressing channels at an angle greater than 0 degree;

(e) delivering a second address tag through each of the second addressing channels to each second area in the sample, wherein each second address tag is to be coupled to the probe and/or the adaptor, whereby the first address tag and the second address tag at an intersection between a first area and a second area determine the intersection's address;

(f) analyzing the probe and/or the adaptor bound to the biological target, the analysis comprising: (1) determining the abundance, expression and/or activity of the biological target by assessing the amount of the probe and/or the adaptor bound to the biological target; and (2) determining the identities of the identity tag and the first and second address tags at each address; and (g) determining a spatial pattern of the biological target abundance, expression and/or activity in the sample based on the analysis of step (f).

In yet another aspect, provided herein is a method of determining a spatial pattern of abundance, expression and/or activity of a biological target in a sample, comprising:

(a) affixing a sample to a first microfluidic device having multiple first addressing channels, wherein each first addressing channel identifies a first area in the sample;

(b) delivering a probe for a biological target through each of the first addressing channels to each first area in the sample, the probe comprising a binding moiety capable of binding to the biological target, and optionally, delivering an adaptor that specifically binds to the probe, wherein the probe and/or the adaptor comprises: (1) a first address tag that identifies an area in the sample to which the probe and/or the adaptor is delivered; and (2) an identity tag that identifies the biological target or the binding moiety;

(c) affixing the sample from step (b) to a second microfluidic device having multiple second addressing channels, wherein each second addressing channel identifies in the sample a second area that intersects with a first area identified by the first addressing channels at an angle greater than 0 degree;

(d) delivering a second address tag through each of the second addressing channels to each second area in the sample, wherein each second address tag is to be coupled to the probe and/or the adaptor, whereby the first address tag and the second address tag at an intersection between a first area and a second area determine the intersection's address;

(e) analyzing the probe and/or the adaptor bound to the biological target, the analysis comprising: (1) determining the abundance, expression and/or activity of the biological target by assessing the amount of the probe and/or the adaptor bound to the biological target; and (2) determining the identities of the identity tag and the first and second address tags at each address; and (f) determining a spatial pattern of the biological target abundance, expression and/or activity in the sample based on the analysis of step (e).

In any of the preceding embodiments or combinations thereof, the angle can be about 90 degrees, about 80 degrees, about 70 degrees, about 60 degrees, about 50 degrees, about 40 degrees, about 30 degrees, about 20 degrees, or about 10 degrees. In any of the preceding embodiments, the multiple first addressing channels may substantially parallel each other and the multiple second addressing channels may substantially parallel each other.

In any of the preceding embodiments or combinations thereof, the sample can be a biological sample selected from the group consisting of a freshly isolated sample, a fixed sample, a frozen sample, an embedded sample, a processed sample, or a combination thereof.

In any of the preceding embodiments or combinations thereof, the first addressing channels may be disposed on the same device as the second addressing channels. In other embodiments, the first addressing channels can be disposed on a separate device from the second addressing channels.

In any of the preceding embodiments or combinations thereof, the first and/or second microfluidic device can be manufactured by soft-lithographic techniques. In certain aspects, the number of the first and/or second addressing channels can be n, n being an integer greater than 1. In certain examples, n can be 2, 3, 4, 5, 6, 7, 8, 9, 10, 11, 12, 13, 14, 15, 16, 17, 18, 19, 20, 30, 40, 50, 60, 70, 80, 90, 100, 150, 200, 250, 300, 350, 400, 450, 500, 550, 600, 650, 700, 750, 800, 850, 900, 950, or 1000. In other aspects, n can be an integer between 20 and 30, between 30 and 40, between 40 and 50, between 50 and 60, between 60 and 70, between 70 and 80, between 80 and 90, or between 90 and 100. In yet other aspects, n can be an integer between 100 and 150, between 150 and 200, between 200 and 250, between 250 and 300, between 300 and 350, between 350 and 400, between 400 and 450, between 450 and 500, between 500 and 550, between 550 and 600, between 600 and 650, between 650 and 700, between 700 and 750, between 750 and 800, between 800 and 850, between 850 and 900, between 900 and 950, or between 950 and 1000. In yet other aspects, n can be an integer greater than 1000.

In some embodiments, the width of the first and/or second addressing channels can be about 5 μm, about 10 μm, about 50 μm, about 100 μm, about 150 μm, about 200 μm, about 250 μm, about 300 μm, about 350 μm, about 400 μm, about 450 μm, or about 500 μm. In any of the preceding embodiments, the depth of the first and/or second addressing channels can be about 5 μm, about 10 μm, about 50 μm, about 100 μm, about 150 μm, about 200 μm, about 250 μm, about 300 μm, about 350 μm, about 400 μm, about 450 μm, or about 500 μm. In some aspects, the distance between each first addressing channel and/or between each second addressing channel can be about 5 μm, about 10 μm, about 50 μm, about 100 μm, about 150 μm, about 200 μm, about 250 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm, about 1.0 mm, about 1.2 mm, about 1.3 mm, about 1.4 mm, about 1.5 mm, about 1.6 mm, about 1.7 mm, about 1.8 mm, about 1.9 mm, or about 2.0 mm. In some embodiments, the first addressing channels and/or the second addressing channels may be evenly or unevenly spaced. The distance between each first addressing channel and/or between each second addressing channel can be chosen and/or adjusted to fit the particular need.

In any of the preceding embodiments or combinations thereof, the first and/or second address tag may comprise an oligonucleotide. In other aspects, the identity tag may comprise an oligonucleotide.

In any of the preceding embodiments or combinations thereof, the biological target can be a nucleic acid and the probe for the biological target can comprise an oligonucleotide. In certain embodiments, the biological target can be a nucleic acid and two probes for the nucleic acid target may be used.

In any of the preceding embodiments or combinations thereof, the biological target may be a protein, and the probe for the target protein can comprise an oligonucleotide and a target-binding moiety which is a protein.

In any of the preceding embodiments, the biological target may comprise an enzyme. In certain aspects, the binding moiety of the probe for the biological target can comprise an antibody, an aptamer, or a small molecule, or any combination thereof.

In any of the preceding embodiments or combinations thereof, the analyzing step may be performed by nucleic acid sequencing, for example, high-throughput digital nucleic acid sequencing. In any of the preceding embodiments or combinations thereof, spatial patterns of the abundance, expression, and/or activity of multiple biological targets in the sample may be determined in parallel.

In any of the preceding embodiments or combinations thereof, the product of the number of biological targets being assayed and the number of addresses being assayed in the sample can be greater than 20, greater than 50, greater than 75, greater than 100, greater than 1,000, greater than 10,000, greater than 100,000, or greater than 1,000,000. In any of the preceding embodiments or combinations thereof, at least one hundred thousand, at least five hundred thousand, or at least one million probes bound to the biological target may be analyzed in parallel.

In any of the preceding embodiments or combinations thereof, software programmed hardware may perform at least two steps of the delivering steps, the affixing steps, the analyzing step and the determining step.

In any of the preceding embodiments or combinations thereof, a known percentage of the probe for the biological target can be an attenuator probe. In certain aspects, the attenuator probe may prevent production of an amplifiable product. For example, an attenuator probe may compete with an active probe for binding to the target. While an active probe can lead to the generation of an amplifiable product from the target, an attenuator probe does not or has reduced ability in generating an amplifiable product. In one embodiment, the attenuator probe can lack a 5' phosphate.

In any of the preceding embodiments or combinations thereof, the probe for the biological target can comprise a variable tag region, which can be used to group sequencing products of the probe that is bound to the biological target. In certain embodiments, the variable tag region may be a 4-mer, 5-mer, 6-mer, 7-mer, 8-mer, 9-mer, 10-mer, 11-mer, 12-mer, 13-mer, 14-mer, 15-mer, 16-mer, 17-mer, 18-mer, 19-mer, 20-mer, or even longer nucleotide sequence. In one aspect, the variable tag region may be randomly produced.

In any of the preceding embodiments or any combinations thereof, the address tag may be coupled to the probe by ligation, by extension, by ligation following extension, or any combination thereof.

In yet another aspect, provided herein is a method of address coding multiple sites in a sample, comprising:

(a) providing a sample affixed to a first microfluidic device having multiple first addressing channels, wherein each first addressing channel identifies a first area in the sample;

(b) delivering a first probe capable of binding to a target in the sample through each of the first addressing channels to each first area in the sample;

(c) affixing the sample from step (b) to a second microfluidic device having multiple second addressing channels, wherein each second addressing channel identifies in the sample a second area that intersects with a first area identified by the first addressing channels at an angle greater than 0 degree;

(d) delivering a second probe capable of binding to the target in the sample through each of the second addressing channels to each second area in the sample; and (e) determining an address of an intersection between a first area and a second area in the sample based on the first probe and the second probe bound to the target at the intersection.

In one aspect, the angle can be about 90 degrees, about 80 degrees, about 70 degrees, about 60 degrees, about 50 degrees, about 40 degrees, about 30 degrees, about 20 degrees, or about 10 degrees. In another aspect, the first addressing channels may substantially parallel each other and the second addressing channels can substantially parallel each other. In certain embodiments, the sample can be a biological sample selected from the group consisting of a freshly isolated sample, a fixed sample, a frozen sample, an embedded sample, a processed sample, or a combination thereof. In other embodiments, the first addressing channels may be disposed on the same device as the second addressing channels. Alternatively, in some embodiments, the first addressing channels can be disposed on a separate device from the second addressing channels. In certain aspects, the first or second microfluidic device can be manufactured by soft-lithographic techniques. In some embodiments, the number of the first or second addressing channels is n, n being an integer greater than 1. In other embodiments, the width of the first and/or second addressing channels is about 5 μm, about 10 μm, about 50 μm, about 100 μm, about 150 μm, about 200 μm, about 250 μm, about 300 μm, about 350 μm, about 400 μm, about 450 μm, or about 500 μm. In one aspect, the depth of the first and/or second addressing channels is about 5 μm, about 10 μm, about 50 μm, about 100 μm, about 150 μm, about 200 μm, about 250 μm, about 300 μm, about 350 μm, about 400 μm, about 450 μm, or about 500 μm. In another aspect, the distance between each first addressing channel and/or between each second addressing channel is about 5 μm, about 10 μm, about 50 μm, about 100 μm, about 150 μm, about 200 μm, about 250 μm, about 300 μm, about 350 μm, about 400 μm, about 450 μm, about 500 μm, about 550 μm, about 600 μm, about 650 μm, about 700 μm, about 750 μm, about 800 μm, about 850 μm, about 900 μm, about 950 μm, about 1.0 mm, about 1.2 mm, about 1.3 mm, about 1.4 mm, about 1.5 mm, about 1.6 mm, about 1.7 mm, about 1.8 mm, about 1.9 mm, or about 2.0 mm. In yet another aspect, the first probes may be different from each other, and the second probes may be different from each other and different from the first probes.

BRIEF DESCRIPTION OF THE DRAWINGS

FIG. 15 illustrates sequential address tagging schemes, according to embodiments of the present disclosure.

FIG. 20 illustrates a method for reducing random errors during the sequencing step (FIG. 20A), and exemplary configurations of probes with integrated X and Y address tags and variable tag region z (FIG. 20B), according to some embodiments of the present disclosure.

DETAILED DESCRIPTION

Figure 1:
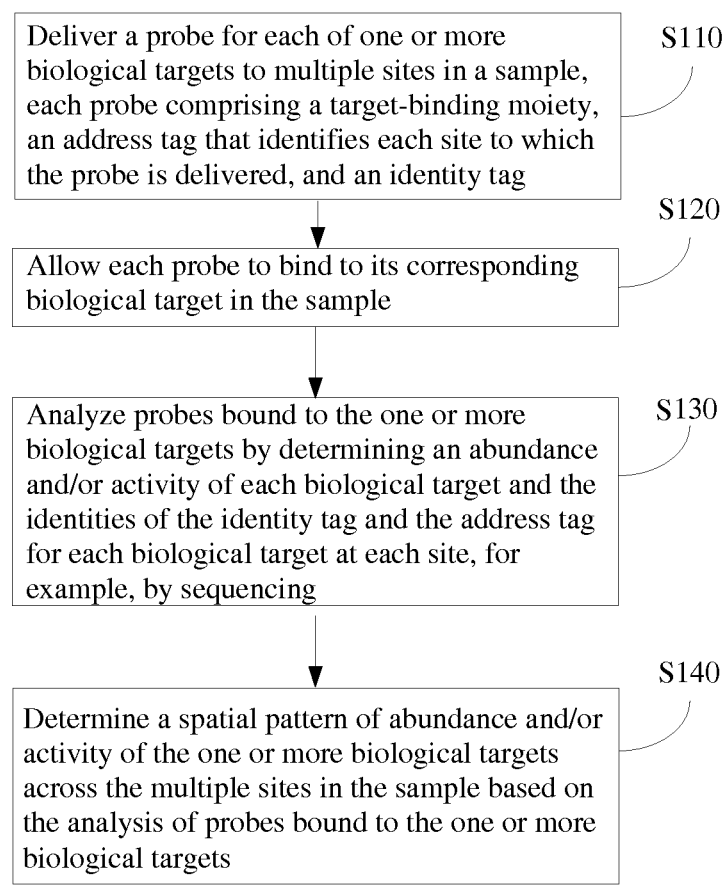
FIG. 1 is a flow chart illustrating exemplary steps of a method of determining a spatial pattern of abundance, expression, and/or activity of one or more biological targets across multiple sites in a sample, according to an embodiment of the present disclosure.

A detailed description of one or more embodiments of the claimed subject matter is provided below along with accompanying figures that illustrate the principles of the claimed subject matter. The claimed subject matter is described in connection with such embodiments, but is not limited to any embodiment. It is to be understood that the claimed subject matter may be embodied in various forms, and encompasses numerous alternatives, modifications and equivalents. Therefore, specific details disclosed herein are not to be interpreted as limiting, but rather as a basis for the claims and as a representative basis for teaching one skilled in the art to employ the claimed subject matter in virtually any appropriately detailed system, structure or manner. Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. For the purpose of clarity, technical material that is known in the technical fields related to the claimed subject matter has not been described in detail so that the claimed subject matter is not unnecessarily obscured.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

All publications, including patent documents, scientific articles and databases, referred to in this application and the bibliography and attachments are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The practice of the provided embodiments will employ, unless otherwise indicated, conventional techniques and descriptions of organic chemistry, polymer technology, molecular biology (including recombinant techniques), cell biology, biochemistry, and sequencing technology, which are within the skill of those who practice in the art. Such conventional techniques include polymer array synthesis, hybridization and ligation of polynucleotides, and detection of hybridization using a label. Specific illustrations of suitable techniques can be had by reference to the examples herein. However, other equivalent conventional procedures can, of course, also be used. Such conventional techniques and descriptions can be found in standard laboratory manuals such as Green, et al., Eds., *Genome Analysis: A Laboratory Manual Series* (Vols. I-IV)(1999); Weiner, Gabriel, Stephens, Eds., *Genetic Variation: A Laboratory Manual* (2007); Dieffenbach, Dveksler, Eds., *PCR Primer: A Laboratory Manual* (2003); Bowtell and Sambrook, *DNA Microarrays: A Molecular Cloning Manual* (2003); Mount, *Bioinformatics: Sequence and Genome Anazvsis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Ausubel et al. eds., *Current Protocols in Molecular Biology* (1987); T. Brown ed., *Essential Molecular Biology* (1991), IRL Press; Goeddel ed., *Gene Expression Technology* (1991), Academic Press; A. Bothwell et al. eds., *Methods for Cloning and Analysis of Eukaryotic Genes* (1990), Bartlett Publ.; M. Kriegler, *Gene Transfer and Expression* (1990), Stockton Press; R. Wu et al. eds., *Recombinant DNA Methodology* (1989), Academic Press; M. McPherson et al., *PCR: A Practical Approach* (1991), IRL Press at Oxford University Press; Stryer, *Biochemistry* (4th Ed.)(1995), W. H. Freeman, New York N.Y.; Gait, *Oligonucleotide Synthesis: A Practical Approach* (2002), IRL Press, London; Nelson and Cox, Lehninger, *Principles of Biochemistry* (2000) 3rd Ed., W. H. Freeman Pub., New York, N.Y.; Berg, et al., *Biochemistry* (2002) 5th Ed., W. H. Freeman Pub., New York, N.Y.; D. Weir & C. Blackwell, eds., *Handbook of Experimental Immunology* (1996), Wiley-Blackwell; A. Abbas et al., *Cellular and Molecular Immunology* (1991, 1994), W.B. Saunders Co.; and J. Coligan et al. eds., *Current Protocols in Immunology* (1991), all of which are herein incorporated in their entirety by reference for all purposes.

As used herein and in the appended claims, the singular forms "a," "an," and "the" include plural referents unless the context clearly dictates otherwise. For example, "a" or "an" means "at least one" or "one or more." Thus, reference to "a biological target" refers to one or more biological targets, and reference to "the method" includes reference to equivalent steps and methods disclosed herein and/or known to those skilled in the art, and so forth.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

As used herein, an "individual" can be any living organism, including humans and other mammals. A "subject" as used herein can be an organism to which the provided compositions, methods, kits, devices, and systems can be administered or applied. In one embodiment, the subject can be a mammal or a cell, a tissue, an organ or a part of the mammal. Mammals include, but are not limited to, humans, and non-human animals, including farm animals, sport animals, rodents and pets.

As used herein, a "biological sample" can refer to any sample obtained from a living or viral source or other source of macromolecules and biomolecules, and includes any cell type or tissue of a subject from which nucleic acid or protein or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom.

As used herein, a "composition" can be any mixture of two or more products or compounds. It may be a solution, a suspension, liquid, powder, a paste, aqueous, non-aqueous or any combination thereof.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2', 5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. A nucleic acid generally will contain phosphodiester bonds, although in some cases nucleic acid analogs may be included that have alternative backbones such as phosphoramidite, phosphorodithioate, or methylphophoroamidite linkages; or peptide nucleic acid backbones and linkages. Other analog nucleic acids include those with bicyclic structures including locked nucleic acids, positive backbones, non-ionic backbones and non-ribose backbones. Modifications of the ribose-phosphate backbone may be done to increase the stability of the molecules; for example, PNA:DNA hybrids can exhibit higher stability in some environments. The terms "polynucleotide," "oligonucleotide," "nucleic acid" and "nucleic acid molecule" can comprise any suitable length, such as at least 5, 6, 7, 8, 9, 10, 20, 30, 40, 50, 100, 200, 300, 400, 500, 1,000 or more nucleotides.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

"Nucleic acid probe" refers to a structure comprising a polynucleotide, as defined above, that contains a nucleic acid sequence that can bind to a corresponding target. The polynucleotide regions of probes may be composed of DNA, and/or RNA, and/or synthetic nucleotide analogs.

The terms "polypeptide", "oligopeptide", "peptide" and "protein" are used interchangeably herein to refer to polymers of amino acids of any length, e.g., at least 5, 6, 7, 8, 9, 10, 20, 30, 40, 50, 100, 200, 300, 400, 500, 1,000 or more amino acids. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

The terms "binding agent" and "target-binding moiety" as used herein may refer to any agent or any moiety thereof that specifically binds to a biological molecule of interest.

The biological targets or molecules to be detected can be any biological molecules including but not limited to proteins, nucleic acids, lipids, carbohydrates, ions, or multicomponent complexes containing any of the above. Examples of subcellular targets include organelles, e.g., mitochondria, Golgi apparatus, endoplasmic reticulum, chloroplasts, endocytic vesicles, exocytic vesicles, vacuoles, lysosomes, etc. Exemplary nucleic acid targets can include genomic DNA of various conformations (e.g., A-DNA, B-DNA, Z-DNA), mitochondria DNA (mtDNA), mRNA, tRNA, rRNA, hRNA, miRNA, and piRNA.

As used herein, "biological activity" may include the in vivo activities of a compound or physiological responses that result upon in vivo administration of a compound, composition or other mixture. Biological activity, thus, may encompass therapeutic effects and pharmaceutical activity of such compounds, compositions and mixtures. Biological activities may be observed in vitro systems designed to test or use such activities.

The term "binding" can refer to an attractive interaction between two molecules which results in a stable association in which the molecules are in close proximity to each other. Molecular binding can be classified into the following types: non-covalent, reversible covalent and irreversible covalent. Molecules that can participate in molecular binding include proteins, nucleic acids, carbohydrates, lipids, and small organic molecules such as pharmaceutical compounds. Proteins that form stable complexes with other molecules are often referred to as receptors while their binding partners are called ligands. Nucleic acids can also form stable complex with themselves or others, for example, DNA-protein complex, DNA-DNA complex, DNA-RNA complex.

As used herein, the term "specific binding" refers to the specificity of a binder, e.g., an antibody, such that it preferentially binds to a target, such as a polypeptide antigen. When referring to a binding partner (e.g., protein, nucleic acid, antibody or other affinity capture agent, etc.), "specific binding" can include a binding reaction of two or more binding partners with high affinity and/or complementarity to ensure selective hybridization under designated assay conditions. Typically, specific binding will be at least three times the standard deviation of the background signal. Thus, under designated conditions the binding partner binds to its particular target molecule and does not bind in a significant amount to other molecules present in the sample. Recognition by a binder or an antibody of a particular target in the presence of other potential interfering substances is one characteristic of such binding. Preferably, binders, antibodies or antibody fragments that are specific for or bind specifically to a target bind to the target with higher affinity than binding to other non-target substances. Also preferably, binders, antibodies or antibody fragments that are specific for or bind specifically to a target avoid binding to a significant percentage of non-target substances, e.g., non-target substances present in a testing sample. In some embodiments, binders, antibodies or antibody fragments of the present disclosure avoid binding greater than about 90% of non-target substances, although higher percentages are clearly contemplated and preferred. For example, binders, antibodies or antibody fragments of the present disclosure avoid binding about 91%, about 92%, about 93%, about 94%, about 95%, about 96%, about 97%, about 98%, about 99%, and about 99% or more of non-target substances. In other embodiments, binders, antibodies or antibody fragments of the present disclosure avoid binding greater than about 10%, 20%, 30%, 40%, 50%, 60%, or 70%, or greater than about 75%, or greater than about 80%, or greater than about 85% of non-target substances.

The term "antibody" as used herein may include an entire immunoglobulin or antibody or any functional fragment of an immunoglobulin molecule which is capable of specific binding to an antigen, such as a carbohydrate, polynucleotide, lipid, polypeptide, or a small molecule, etc., through at least one antigen recognition site, located in the variable region of the immunoglobulin molecule, and can be an immunoglobulin of any class, e.g., IgG, IgM, IgA, IgD and IgE. IgY, which is the major antibody type in avian species such as chicken, is also included. An antibody may include the entire antibody as well as any antibody fragments capable of binding the antigen or antigenic fragment of interest. Examples include complete antibody molecules, antibody fragments, such as Fab, F(ab')2, CDRs, VL, VH, and any other portion of an antibody which is capable of specifically binding to an antigen. Antibodies used herein are immunoreactive or immunospecific for, and therefore specifically and selectively bind to, for example, proteins either detected (i.e., biological targets) or used for detection (i.e., probes) in the assays of the invention. An antibody as used herein can be specific for any of the biological targets disclosed herein or any combinations thereof. In certain embodiments, a biological target itself of the present disclosure can be an antibody or fragments thereof.

As used herein, a "fragment thereof" "region thereof" and "portion thereof" can refer to fragments, regions and portions that substantially retain at least one function of the full length polypeptide.

As used herein, the term "antigen" may refer to a target molecule that is specifically bound by an antibody through its antigen recognition site. The antigen may be monovalent or polyvalent, i.e., it may have one or more epitopes recognized by one or more antibodies. Examples of kinds of antigens that can be recognized by antibodies include polypeptides, oligosaccharides, glycoproteins, polynucleotides, lipids, or small molecules, etc.

As used herein, the term "epitope" can refer to a peptide sequence of at least about 3 to 5, preferably about 5 to 10 or 15, and not more than about 1,000 amino acids (or any integer there between), which define a sequence that by itself or as part of a larger sequence, binds to an antibody generated in response to such sequence. There is no critical upper limit to the length of the fragment, which may, for example, comprise nearly the full-length of the antigen sequence, or even a fusion protein comprising two or more epitopes from the target antigen. An epitope for use in the subject invention is not limited to a peptide having the exact sequence of the portion of the parent protein from which it is derived, but also encompasses sequences identical to the native sequence, as well as modifications to the native sequence, such as deletions, additions and substitutions (conservative in nature).

The terms "complementary" and "substantially complementary" may include the hybridization or base pairing or the formation of a duplex between nucleotides or nucleic acids, for instance, between the two strands of a double-stranded DNA molecule or between an oligonucleotide primer and a primer binding site on a single-stranded nucleic acid. Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the other strand, usually at least about 90% to about 95%, and even about 98% to about 100%. In one aspect, two complementary sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

"Hybridization" as used herein may refer to the process in which two single-stranded polynucleotides bind non-covalently to form a stable double-stranded polynucleotide. In one aspect, the resulting double-stranded polynucleotide can be a "hybrid" or "duplex." "Hybridization conditions" typically include salt concentrations of approximately less than 1 M, often less than about 500 mM and may be less than about 200 mM. A "hybridization buffer" includes a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are often performed under stringent conditions, i.e., conditions under which a sequence will hybridize to its target sequence but will not hybridize to other, non-complementary sequences. Stringent conditions are sequence-dependent and are different in different circumstances. For example, longer fragments may require higher hybridization temperatures for specific hybridization than short fragments. As other factors may affect the stringency of hybridization, including base composition and length of the complementary strands, presence of organic solvents, and the extent of base mismatching, the combination of parameters is more important than the absolute measure of any one parameter alone. Generally stringent conditions are selected to be about 5° C. lower than the $T_m$ for the specific sequence at a defined ionic strength and pH. The melting temperature $T_m$ can be the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation, $T_m=81.5+0.41$ (% G+C), when a nucleic acid is in aqueous solution at 1 M NaCl (see e.g., Anderson and Young, Quantitative Filter Hybridization, in *Nucleic Acid Hybridization* (1985)). Other references (e.g., Allawi and SantaLucia, Jr., Biochemistry, 36:10581-94 (1997)) include alternative methods of computation which take structural and environmental, as well as sequence characteristics into account for the calculation of $T_m$.

In general, the stability of a hybrid is a function of the ion concentration and temperature. Typically, a hybridization reaction is performed under conditions of lower stringency, followed by washes of varying, but higher, stringency. Exemplary stringent conditions include a salt concentration of at least 0.01 M to no more than 1 M sodium ion concentration (or other salt) at a pH of about 7.0 to about 8.3 and a temperature of at least 25° C. For example, conditions of 5×SSPE (750 mM NaCl, 50 mM sodium phosphate, 5 mM EDTA at pH 7.4) and a temperature of approximately 30° C. are suitable for allele-specific hybridizations, though a suitable temperature depends on the length and/or GC content of the region hybridized. In one aspect, "stringency of hybridization" in determining percentage mismatch can be as follows: 1) high stringency: 0.1×SSPE, 0.1% SDS, 65° C.; 2) medium stringency: 0.2×SSPE, 0.1% SDS, 50° C. (also referred to as moderate stringency); and 3) low stringency: 1.0×SSPE, 0.1% SDS, 50° C. It is understood that equivalent stringencies may be achieved using alternative buffers, salts and temperatures. For example, moderately stringent hybridization can refer to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions can be conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization can refer to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See M. Kanehisa, Nucleic Acids Res. 12:203 (1984).

A "primer" used herein can be an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers usually are extended by a DNA polymerase.

"Ligation" may refer to the formation of a covalent bond or linkage between the termini of two or more nucleic acids, e.g., oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide.

"Sequencing," "sequence determination" and the like means determination of information relating to the nucleotide base sequence of a nucleic acid. Such information may include the identification or determination of partial as well as full sequence information of the nucleic acid. Sequence information may be determined with varying degrees of statistical reliability or confidence. In one aspect, the term includes the determination of the identity and ordering of a plurality of contiguous nucleotides in a nucleic acid. "High throughput digital sequencing" or "next generation sequencing" means sequence determination using methods that determine many (typically thousands to billions) of nucleic acid sequences in an intrinsically parallel manner, i.e. where DNA templates are prepared for sequencing not one at a time, but in a bulk process, and where many sequences are read out preferably in parallel, or alternatively using an ultra-high throughput serial process that itself may be parallelized. Such methods include but are not limited to pyrosequencing (for example, as commercialized by 454 Life Sciences, Inc., Branford, Conn.); sequencing by ligation (for example, as commercialized in the SOLiD™ technology, Life Technologies, Inc., Carlsbad, Calif.); sequencing by synthesis using modified nucleotides (such as commercialized in TruSeq™ and HiSeq™ technology by Illumina, Inc., San Diego, Calif.; HeliScope™ by Helicos Biosciences Corporation, Cambridge, Mass.; and PacBio RS by Pacific Biosciences of California, Inc., Menlo Park, Calif.), sequencing by ion detection technologies (such as Ion Torrent™ technology, Life Technologies, Carlsbad, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

"SNP" or "single nucleotide polymorphism" may include a genetic variation between individuals; e.g., a single nitrogenous base position in the DNA of organisms that is variable. SNPs are found across the genome; much of the genetic variation between individuals is due to variation at SNP loci, and often this genetic variation results in phenotypic variation between individuals. SNPs for use in the present invention and their respective alleles may be derived from any number of sources, such as public databases (U.C. Santa Cruz Human Genome Browser Gateway (genome.ucsc.edu/cgi-bin/hgGateway) or the NCBI dbSNP website (www.ncbi.nlm.nih gov/SNP/), or may be experimentally determined as described in U.S. Pat. No. 6,969,589; and US Pub. No. 2006/0188875 entitled "Human Genomic Polymorphisms." Although the use of SNPs is described in some of the embodiments presented herein, it will be understood that other biallelic or multi-allelic genetic markers may also be used. A biallelic genetic marker is one that has two polymorphic forms, or alleles. As mentioned above, for a biallelic genetic marker that is associated with a trait, the allele that is more abundant in the genetic composition of a case group as compared to a control group is termed the "associated allele," and the other allele may be referred to as the "unassociated allele." Thus, for each biallelic polymorphism that is associated with a given trait (e.g., a disease or drug response), there is a corresponding associated allele. Other biallelic polymorphisms that may be used with the methods presented herein include, but are not limited to multinucleotide changes, insertions, deletions, and translocations. It will be further appreciated that references to DNA herein may include genomic DNA, mitochondrial DNA, episomal DNA, and/or derivatives of DNA such as amplicons, RNA transcripts, cDNA, DNA analogs, etc. The polymorphic loci that are screened in an association study may be in a diploid or a haploid state and, ideally, would be from sites across the genome.

As used herein, the term "microfluidic device" may generally refer to a device through which materials, particularly fluid borne materials, such as liquids, can be transported, in some embodiments on a micro-scale, and in some embodiments on a nanoscale. Thus, the microfluidic devices described by the presently disclosed subject matter can comprise microscale features, nanoscale features, and combinations thereof.

Accordingly, an exemplary microfluidic device typically comprises structural or functional features dimensioned on the order of a millimeter-scale or less, which are capable of manipulating a fluid at a flow rate on the order of a µL/min or less. Typically, such features include, but are not limited to channels, fluid reservoirs, reaction chambers, mixing chambers, and separation regions. In some examples, the channels include at least one cross-sectional dimension that is in a range of from about 0.1 µm to about 500 µm. The use of dimensions on this order allows the incorporation of a greater number of channels in a smaller area, and utilizes smaller volumes of fluids.

A microfluidic device can exist alone or can be a part of a microfluidic system which, for example and without limitation, can include: pumps for introducing fluids, e.g., samples, reagents, buffers and the like, into the system and/or through the system; detection equipment or systems; data storage systems; and control systems for controlling fluid transport and/or direction within the device, monitoring and controlling environmental conditions to which fluids in the device are subjected, e.g., temperature, current, and the like.

As used herein, the terms "channel," "micro-channel," "fluidic channel," and "microfluidic channel" are used interchangeably and can mean a recess or cavity formed in a material by imparting a pattern from a patterned substrate into a material or by any suitable material removing technique, or can mean a recess or cavity in combination with any suitable fluid-conducting structure mounted in the recess or cavity, such as a tube, capillary, or the like. In the present invention, channel size means the cross-sectional area of the microfluidic channel.

As used herein, the terms "flow channel" and "control channel" are used interchangeably and can mean a channel in a microfluidic device in which a material, such as a fluid, e.g., a gas or a liquid, can flow through. More particularly, the term "flow channel" refers to a channel in which a material of interest, e.g., a solvent or a chemical reagent, can flow through. Further, the term "control channel" refers to a flow channel in which a material, such as a fluid, e.g., a gas or a liquid, can flow through in such a way to actuate a valve or pump.

As used herein, "chip" may refer to a solid substrate with a plurality of one-, two- or three-dimensional micro structures or micro-scale structures on which certain processes, such as physical, chemical, biological, biophysical or biochemical processes, etc., can be carried out. The micro structures or micro-scale structures such as, channels and wells, electrode elements, electromagnetic elements, are incorporated into, fabricated on or otherwise attached to the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips of the present invention can vary considerably, e.g., from about 1 $mm^2$ to about 0.25 $m^2$. Preferably, the size of the chips is from about 4 $mm^2$ to about 25 $cm^2$ with a characteristic dimension from about 1 mm to about 5 cm. The chip surfaces may be flat, or not flat. The chips with non-flat surfaces may include channels or wells fabricated on the surfaces.

A microfluidic chip can be used for the methods and assay systems disclosed herein. A microfluidic chip can be made from any suitable materials, such as PDMS (Polydimethylsiloxane), glass, PMMA (polymethylmethacrylate), PET (polyethylene terephthalate), PC (Polycarbonate), etc., or a combination thereof.

"Multiplexing" or "multiplex assay" herein may refer to an assay or other analytical method in which the presence and/or amount of multiple targets, e.g., multiple nucleic acid target sequences, can be assayed simultaneously by using more than one capture probe conjugate, each of which has at least one different detection characteristic, e.g., fluorescence characteristic (for example excitation wavelength, emission wavelength, emission intensity, FWHM (full width at half maximum peak height), or fluorescence lifetime) or a unique nucleic acid or protein sequence characteristic.

Assays for Determining Spatial Patterns of Biological Targets

Disclosed herein are spatially-encoded, multiplexed methods and assay systems capable of high levels of multiplexing with an efficient spatial encoding scheme. In one embodiment, provided herein is instrumentation capable of delivering reagents to a sample and thereby spatially encoding multiple sites to which the reagents are delivered. In one aspect, reagents can be delivered to a sample according to a known spatial pattern, for example, a spatial pattern determined by histological features of the sample. In another aspect, microfluidic devices with addressing channels and the like are used to deliver reagents to a sample, and to spatially encode multiple sites in the sample to which the reagents are delivered. In some embodiments, the spatially-encoded ("addressed," or "address tagged"), multiplexed methods and assay systems comprise a decoding feature determined by a readout that is digital in nature. In one aspect, the methods and assay systems disclosed herein detect the presence or absence of a biological target or a biological activity indicative of a biological target. In another aspect, provided herein are methods and assay systems that can detect the amount or abundance of a biological target or biological activity indicative of a biological target at multiple sites in a sample, as well as the location of each of the multiple sites in the sample. Based on the analysis of the amount or abundance and the location information of one or more biological targets or activities, spatial patterns across the multiple sites in the sample can be generated. In any of the preceding embodiments, the method or assay system may not depend on an imaging technique for determining spatial or location information of the one or more biological targets in the sample, although the method or assay system may optionally comprise using an imaging technique for other purposes. Imaging techniques may include but are not limited to conventional immunohistochemical (IHC) imaging and immunofluorescence (IF) imaging.

The present disclosure further provides instrumentation with an ability to deliver reagents to multiple sites in a sample, wherein each of the multiple sites can be identified by the reagents delivered thereto. In one embodiment, reagents are delivered in a spatially-defined pattern. The instrumentation, together with software, reagents and protocols, provides a key component of the methods and assay systems of the present disclosure, allowing for measurement of numerous biological targets or activities, including DNA, RNA and/or protein expression, and spatial localization of such biological targets or activities in a sample. In one embodiment, the abundance, expression, and/or activity and the location of biological targets in the biological samples are determined after the assay products of the multiplexed assay are removed from the biological sample and pooled for analysis. Determination of the abundance, expression, and/or activity and the location of biological targets can be performed by, e.g., next-generation sequencing, which easily provides millions to trillions of data points at low cost. The assay results such as the amount or activity of biological targets can then be mapped back to a specific location in the biological sample. The methods and assay systems provide tools to analyze the complex spatial patterns of cellular function and regulation in biological samples.

In one aspect, a method of determining a spatial pattern of abundance, expression, and/or activity of one or more biological targets across multiple sites in a sample is provided in FIG. 1. At Step 110, a probe for each of one or more biological targets is delivered to multiple sites in a sample, each probe comprising a target-binding moiety, an address tag that identifies each site to which the probe is delivered, and an identity tag.

In any of the embodiments of the present disclosure, the sample can be any biological sample or samples that can be affixed to a support or provided essentially in a two-dimensional manner, such that an assayed biological target or activity can be tied back to the location within the biological sample. In certain embodiments, the sample can be a freshly isolated sample, a fixed sample, a frozen sample, an embedded sample, a processed sample, or a combination thereof. Exemplary samples of the present disclosure include tissue sections (e.g., including whole animal sectioning and tissue biopsies), cell populations, or other biological structure disposed upon a support, such as on a slide (e.g., a microscope slide) or culture dish, and the like. In preferred embodiments, the methods and assay systems of the present disclosure are compatible with numerous biological sample types, including fresh samples, such as primary tissue sections, and preserved samples including but not limited to frozen samples and formalin-fixed, paraffin-embedded (FFPE) samples. In certain embodiments, the sample can be fixed with a suitable concentration of formaldehyde or paraformaldehyde, for example, 4% of formaldehyde or paraformaldehyde in phosphate buffered saline (PBS). In certain embodiments, the biological samples are immobilized on a substrate surface having discrete, independently measureable areas.

In one embodiment, the biological sample may contain one or more biological targets of interest. In any of the embodiment of the present disclosure, the one or more biological targets can be any biological molecules including but not limited to proteins, nucleic acids, lipids, carbohydrates, ions, or multicomponent complexes containing any of the above. Examples of subcellular targets include organelles, e.g., mitochondria, Golgi apparatus, endoplasmic reticulum, chloroplasts, endocytic vesicles, exocytic vesicles, vacuoles, lysosomes, etc. In some embodiments, the one or more biological targets can be nucleic acids, including RNA transcripts, genomic DNA sequences, cDNAs, amplicons, or other nucleic acid sequences. In other embodiments, the one or more biological targets can be proteins, enzymes (protein enzymes or ribozymes) and the like.

At Step 110, the probe for each of the multiple biological targets comprise: (1) a target-binding moiety capable of binding to the probe's corresponding biological target; (2) an address tag that identifies each site to which the probe is delivered; and (3) an identity tag that identifies the probe's corresponding biological target or target-binding moiety. Depending on the nature of the biological target, the target-binding moiety can be a target-specific nucleotide sequence (for example, a sequence complementary to a sequence of a nucleic acid target), small molecule, aptamer, antibody, lipid, carbohydrate, ion, affinity capture agent, or multicomponent complexes containing any of the above. The address tag identifies the position in the sample to which the probe is delivered, and the identity tag identifies the probe's corresponding biological target being assayed or the target-binding moiety. Thus, the identities of the address tag and the identity tag can be used to link assay results to biological targets and locations in the sample. In preferred embodiments, there can be at least two address tags for a biological target at each of multiple sites in a sample, each address tag identifying a parameter of each of the multiple sites. For example, there can be an X-axis address tag and a Y-axis address tag for each site in a sample placed on an X-Y coordinate plane. Thus, each site can be uniquely identified by its corresponding (X, Y) coordinates. In preferred embodiments of the present disclosure, the address tags and/or the identity tags can be oligonucleotides. In other embodiments, the address tags and/or the identity tags can be mass tags, fluorescent labels, or other moieties.

In some embodiments, the target-binding moiety, address tag, and/or identity tag of the probe are pre-coupled before being delivered to the biological sample. In the case where the probes are oligonucleotides, the target-binding sequence, address tag sequence, and/or identity tag sequence can be synthesized as a single oligonucleotide. Alternatively, the target-binding moiety, address tag, and/or identity tag of the probe can be synthesized or obtained separately and combined before delivery to the biological sample. For example, two separate oligonucleotides can be synthesized and coupled by, e.g., ligation; or an antibody and an oligonucleotide can be prepared separately and conjugated before delivery to the biological sample. In other embodiments, the probes and the address tags can be synthesized separately, and delivered to the biological sample at different steps (e.g., probes first and address tags thereafter, or vice versa) in the assay.

At Step 120, the probe is allowed to bind to its corresponding biological target in the sample and thereby to react or interact with the biological target. For example, conditions are provided to allow oligonucleotides to hybridize to nucleic acid targets, enzymes to catalyze reactions with protein targets, antibodies to bind epitopes within a target, etc. In the case where the biological targets are nucleic acids, the probes are typically oligonucleotides and hybridize to the target nucleic acids. In the case that the biological targets are proteins, the probes typically are aptamers, small molecules, or oligonucleotide-conjugated proteins that interact with target proteins by binding to them or by reacting with them (that is, one of the proteins is a substrate for the other). Oligonucleotides may be coupled to the probes or proteins by conjugation, chemical or photo-crosslinking via suitable groups and the like.

In some embodiments, after allowing the probes to bind to or interact with the one or more biological targets in the sample, probes bound to the biological targets may be separated from probes delivered to the sample but not bound to the biological targets. In one aspect, in the case where the biological targets are nucleic acids and the probes are oligonucleotides, the separation can be accomplished by, e.g., washing the unhybridized probes from the sample. Similarly, for other assays that are based on affinity binding, including those using aptamer, small molecule, and protein probes, washing steps can be used to remove low affinity binders. In the case where the probe is transformed via interaction with the target, e.g., in the case of a peptide, e.g., via cleavage by a protease or phosphorylation by a kinase, it is convenient to collect all probes, including both probes that have interacted with the biological targets and thus transformed and probes not transformed. After collection or pooling, an antibody or other affinity capture agent can be used to capture probes transformed by addition of a moiety (e.g., a phosphate group in cases of phosphorylation by a kinase). In cases where probes have been transformed via cleavage, the transformed probes can be separated, e.g., by capturing the non-transformed probes via a tag that is removed from the transformed probes during the transformation (e.g., by cleavage), or by adding a new tag at the site of cleavage.

In certain other embodiments, probes bound to the biological targets may not need to be separated from probes not bound to the biological targets for determining a spatial pattern of abundance, expression, and/or activity of the biological targets. At Step 130, probes bound to the one or more biological targets are analyzed. In certain embodiments, the analysis comprises determining abundance, expression, and/or activity of each biological target and the identities of the identity tag and the address tag for each biological target at each site. Numerous methods can be used to identify the address tags, identity tags and/or target-binding moieties of the probes of the methods and assay systems disclosed herein. The address tags can be detected using techniques such as mass spectroscopy (e.g., matrix-assisted laser desorption/ionization-time of flight mass spectrometry (MALDI-TOF), LC-MS/MS, and TOF/TOF™ LC/MS/MS), nuclear magnetic resonance imaging, or, preferably, nucleic acid sequencing. Examples of techniques for decoding the probes of the present invention can be found, for example, in US Pub. No. 20080220434, which is incorporated herein by reference. For example, the address tags may be oligonucleotide mass tags (OMTs or massTags). Such tags are described, e.g., in US Pub. No. 20090305237, which is incorporated by reference in its entirety. In yet another aspect, the probes can be amplified and hybridized to a microarray. This would require separate amplification reactions to be carried out, in which each amplification is specific to a particular address tag or subset of tags, accomplished by using tag-specific primers. Each amplification would also incorporate a different resolvable label (e.g. fluorophor). Following hybridization, the relative amounts of a particular target mapping to different spatial locations in the sample can be determined by the relative abundances of the resolvable labels. At Step 140, based on the analysis of probes bound to the one or more biological targets, a spatial pattern of abundance, expression, and/or activity of the one or more biological targets across the multiple sites in the sample is determined.

In a preferred aspect, the probes according to the present disclosure are substrates for high-throughput, next-generation sequencing, and highly parallel next-generation sequencing methods are used to confirm the sequence of the probes (including, for example, the sequence of the target-binding moiety, the address tag, and/or the identity tag). Suitable sequencing technologies include but are not limited to SOLiD™ technology (Life Technologies, Inc.) or Genome Ananlyzer (I lumina, Inc.). Such next-generation sequencing methods can be carried out, for example, using a one pass sequencing method or using paired-end sequencing. Next generation sequencing methods include, but are not limited to, hybridization-based methods, such as disclosed in e.g., Drmanac, U.S. Pat. Nos. 6,864,052; 6,309,824; and 6,401,267; and Drmanac et al., U.S. patent publication 2005/0191656; sequencing-by-synthesis methods, e.g., U.S. Pat. Nos. 6,210,891; 6,828,100; 6,969,488; 6,897,023; 6,833,246; 6,911,345; 6,787,308; 7,297,518; 7,462,449 and 7,501,245; US Publication Application Nos. 20110059436; 20040106110; 20030064398; and 20030022207; Ronaghi, et al., Science, 281:363-365 (1998); and Li, et al., Proc. Natl. Acad. Sci., 100:414-419 (2003); ligation-based methods, e.g., U.S. Pat. Nos. 5,912,148 and 6,130,073; and U.S. Pat. Appln Nos. 20100105052, 20070207482 and 20090018024; nanopore sequencing, e.g., U.S. Pat. Appln Nos. 20070036511; 20080032301; 20080128627; 20090082212; and Soni and Meller, Clin Chem 53:1996-2001 (2007), as well as other methods, e.g., U.S. Pat. Appln Nos. 20110033854; 20090264299; 20090155781; and 20090005252; also, see, McKernan, et al., Genome Res. 19:1527-41 (2009) and Bentley, et al., Nature 456:53-59 (2008), all of which are incorporated herein in their entirety for all purposes.

In preferred embodiments, probes bound to the one or more biological targets are analyzed by sequencing. Such analysis by sequencing comprises determining the amount of a sequencing product, which indicates the abundance, expression, and/or activity of each biological target, the sequencing product comprising all or a portion of the address tag sequence and all or a portion of the identity tag sequence identifying each biological target at each site. In one embodiment, the address tag sequence of the sequencing product allows the mapping of the assay results back to the multiple sites in the sample.

Figure 2:
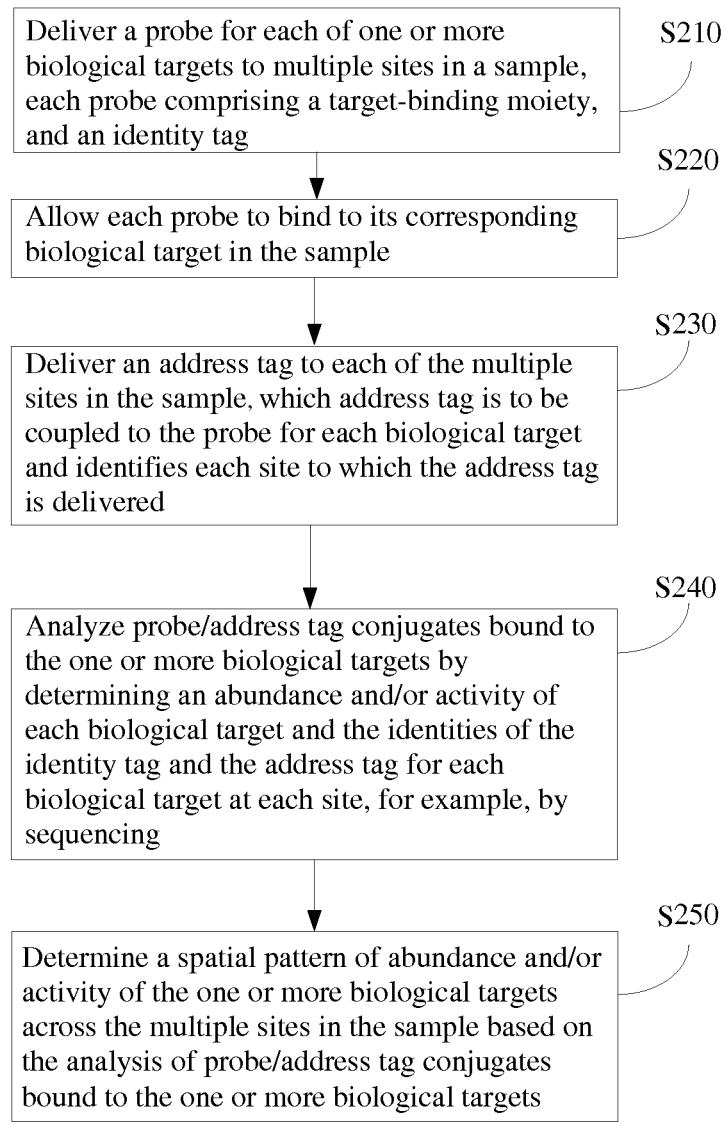
FIG. 2 is a flow chart illustrating exemplary steps of a method of determining a spatial pattern of abundance, expression, and/or activity of one or more biological targets across multiple sites in a sample, according to an embodiment of the present disclosure.

In another aspect, as shown in FIG. 2, a method of determining a spatial pattern of abundance and/or activity of one or more biological targets across multiple sites in a sample is provided, featuring an efficient implementation of an address tagging scheme for the one or more biological targets across the multiple sites. In one embodiment, the address tagging scheme is a combinatorial scheme using at least two address tags for the biological targets for each of the multiple sites in the sample. At Step 210, a probe for each of one or more biological targets to multiple sites in a sample is delivered, each probe comprising (1) a target-binding moiety capable of binding to the probe's corresponding biological target; and (2) an identity tag that identifies the probe's corresponding biological target or target-binding moiety. Depending on the nature of the biological target, the target-binding moiety can be a target-specific nucleotide sequence (for example, a sequence complementary to a sequence of a nucleic acid target), small molecule, aptamer, antibody, lipid, carbohydrate, ion, affinity capture agent, or multicomponent complexes containing any of the above. At Step 220, each probe is allowed to interact with or bind to its corresponding biological target in the sample, under appropriate conditions.

In certain embodiments, probes not bound to the biological targets may be removed, and thereby separated from probes bound to the biological targets. Such separation can be performed essentially as discussed above, for example, by washing the sample to remove unhybridized oligonucleotide probes. In certain other embodiments, probes bound to the biological targets may not need to be separated from probes not bound to the biological targets for determining a spatial pattern of abundance and/or activity of the biological targets.

Next, at Step 230, an address tag is delivered to each of the multiple sites in the sample, and the address tag is to be coupled to the probe for each biological target and identifies each site to which the address tag is delivered. Note that in this aspect, the probe and address tag are delivered in separate steps. In certain embodiments where the probes are oligonucleotides, the address tags may be coupled to the oligonucleotide probes by various means known to the skilled artisan, for example, by extension, ligation, ligation followed by extension, or any combination thereof. For instance, the information in the address tags can be transferred by using a DNA polymerase to extend a probe oligonucleotide that acts as a primer, and thereby copy and incorporate the sequence of the address tags.

At Step 240, probe/address tag conjugates bound to the one or more biological targets are analyzed. In certain embodiments, the analysis comprises determining an abundance and/or activity of each biological target and the identities of the identity tag and the address tag for each biological target at each site. Numerous methods can be used to identify the address tags, identity tags and/or target-binding moieties of the probes, as discussed above. In preferred embodiments, probe/address tag conjugates bound to the one or more biological targets are analyzed by sequencing. Any suitable sequence techniques and methods as discussed above can be used, including high-throughput, next-generation sequencing, and highly parallel next-generation sequencing methods. Preferably, in any of embodiments of the present disclosure, all or a portion of the address tag sequence and all or a portion of the identity tag sequence are determined from the same sequencing product. Preferably, also determined at the same time is the abundance and/or activity of the sequencing product, which indicates an abundance and/or activity of each biological target. In some embodiments, the abundance of sequence products reveals the relative quantity of biological targets at the location.

Based on the analysis of probe/address tag conjugates bound to the one or more biological targets at Step 240, a spatial pattern of abundance and/or activity of the one or more biological targets across the multiple sites in the sample is determined at Step 250, for example, by mapping the assayed abundance and/or activity of each biological target back to each site of the sample.

Although individual steps are discussed in a particular order in certain embodiments to better explain the claimed subject matter, the precise order of the steps can be varied. For example, steps 210 and 230 can be combined, so that a mixture of the probes and address tags is delivered. Coupling of the address tag to the probe may be carried out immediately after the combined steps 210 and 230, or concomitantly with them. It can therefore be appreciated that the address tagging of probe molecules and the separation of probes based on their ability to interact with their corresponding targets can be accomplished with flexibility. Similarly, there is considerable flexibility in the address tagging scheme. As described infra, the methods and assay systems disclosed herein are particularly amenable to combinatorial methods.

Figure 3:
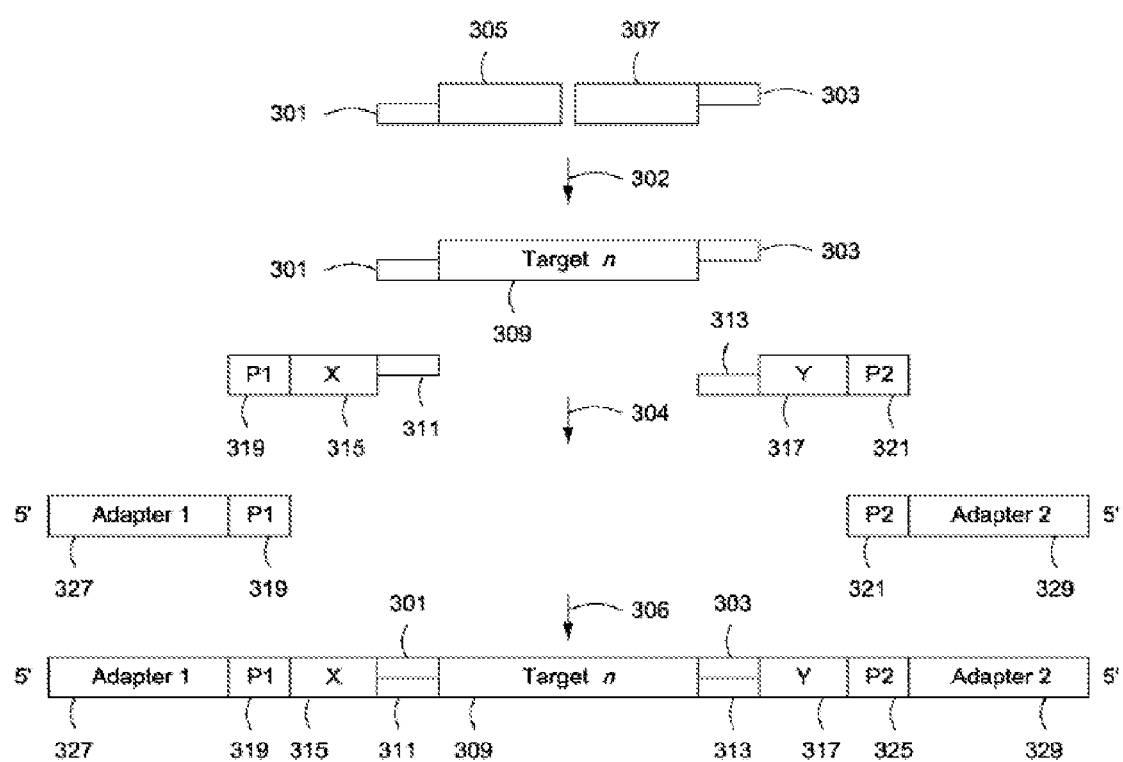
FIG. 3 illustrates a combinatorial addressing scheme, according to one embodiment of the present disclosure.

In particular embodiments, the methods and assay systems can be used for nucleic acid analysis, for example, for genotyping, detecting single nucleotide polymorphisms (SNPs), quantitation of DNA copy number or RNA transcripts, localization of particular transcripts within samples, and the like. FIG. 3 illustrates an exemplary assay and address tagging scheme. For illustrative purposes, the target is a nucleic acid sequence, and two oligonucleotide probes are provided, and it should be understood that the disclosed methods and assay systems can be used for any suitable target employing one or more suitable probes. Each oligonucleotide probe comprises a target-specific region seen at 305 and 307, respectively. In certain embodiments, for example for detecting SNPs, the two target-specific regions are located on either side of the SNP to be analyzed. Each oligonucleotide probe also comprises a ligation region, seen at 301 and 303, respectively. The oligonucleotide probes are allowed to hybridize to a target nucleic acid (not shown) in the biological sample. At Step 302, one or both of the oligonucleotide probes may be extended and ligated to the other probe to form an extended probe comprising target nucleic acid region 309 and ligation regions 301 and 303. In some embodiments, the two probes are immediately adjacent to each other, and only ligation is needed to form an extended probe. In some embodiments, Step 302 may be used to incorporate an SNP sequence or other target sequences to be assayed.

Two address tags, both comprising an address tag region (seen at 315 and 317), a ligation region (seen at 311 and 313), and a primer region (seen at 319 and 321) are combined with and ligated to the extended probe at step 304 to form a target-specific oligonucleotide. In contrast with FIG. 1, the probes and address tags are delivered at separate steps. In some embodiments, a pair of address tags ligate specifically to one side of the target sequence or the other (i.e., 5' or 3' of the target sequence), respectively. In certain embodiments, the ligation and primer regions of the address tags and probes are universal; that is, the set of ligation and primer regions used in constructing the probes and address tags are constant, and only the target-specific regions of the probes and the address tag region of the address tag differ. In alternative embodiments, the ligation and primer regions are not universal and each probe and/or address tag may comprise a different ligation and/or primer region.

Following ligation, the probe/address tag conjugates are eluted, pooled, and, optionally, sequencing adaptors are added to the probe/address tag conjugates via PCR. In alternative embodiments, sequencing primers may be ligated to the address tags, or sequencing primer sequences can be included as part of the address tags. As seen in FIG. 3, each sequencing adaptor comprises primer region 319 or 321, compatible with the primer regions 319 and 321 on the address tags. The final construct comprising first adaptor 327, first primer region 319, first coding tag 315, ligation regions 311 and 301, target region 309, ligation regions 313 and 303, second coding tag 317, second primer region 325 and second adaptor 329 can be subject to sequencing, for example, by input into a digital high-throughput sequencing process.

A combination of extension and ligation reactions are exemplified in FIG. 3, but it should be appreciated that a variety of reactions may be used to couple the address tags to the target-specific probes, including ligation only (e.g., for oligonucleotides that hybridize to contiguous portions of the target nucleic acid sequence). Alternatively, an assay utilizing an additional oligonucleotide, such as in the GOLDEN-GATE® assay (Illumina, Inc., San Diego, Calif.) (see Fan, et al., Cold Spring Symp. Quant. Biol., 68:69-78 (2003)), may be employed.

To maximize the efficiency of address tagging, a combinatorial approach using pairs of address tags can be used. By de-coupling the target-specific information and the spatial information in the address tags, the number of oligonucleotides required for determining a spatial pattern of one or more biological targets across multiple sites in a sample is dramatically reduced, with a concomitant decrease in cost.

Figure 4:
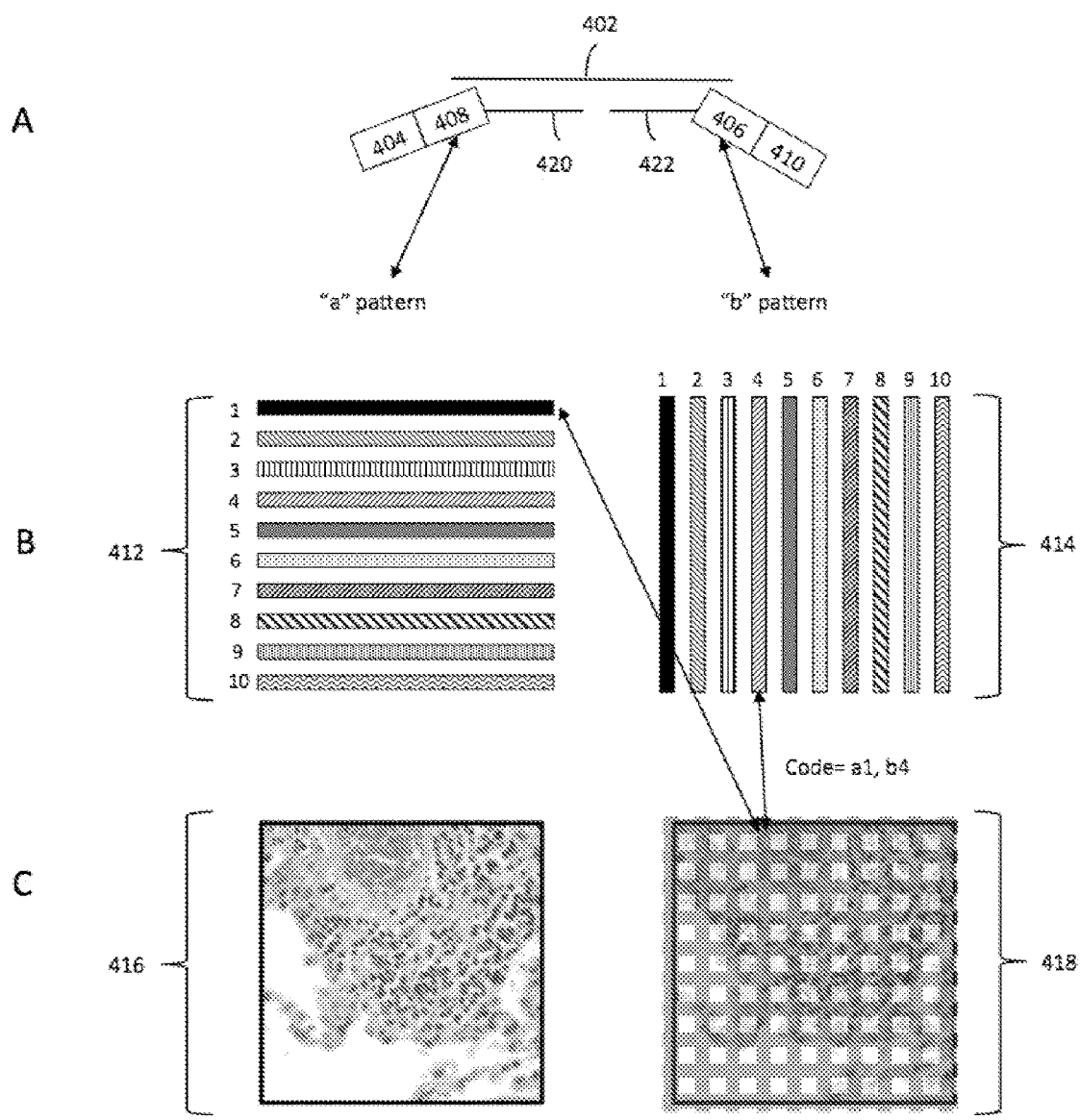
FIG. 4 illustrates combinatorial addressing schemes applied to a sample, according to embodiments of the present disclosure.
Figure 4:
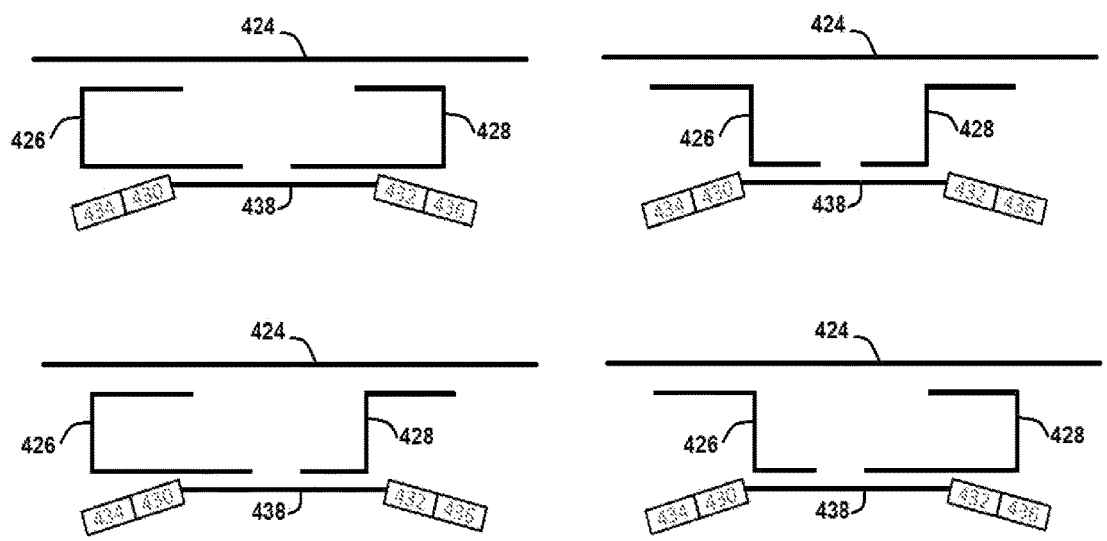

FIG. 4 illustrates one embodiment of a combinatorial address tagging scheme, where nucleic acids in a representative tissue section (shown at 416) are assayed. FIG. 4A shows two probe/address tag conjugates 420 and 422 specifically bound to a biological target 402 of interest. The first probe/address tag conjugate 420 comprises address tag 408, associated with tag 404. Tag 404 can be a universal priming site for amplification of the assay products or an adaptor to enable identification of the address tag 408 and/or other regions of probe/address tag conjugates 420, for example, using sequencing technologies. The second probe/address tag conjugate 422 comprises address tag 406, associated with tag 410. Tag 410 can be a universal priming site for amplification of the assay products or an adaptor to enable identification of the address tag 406 and/or other regions of probe/address tag conjugates 422, for example, using sequencing technologies.

In other embodiments, a biological target 424 is assayed according to the combinatorial address tagging scheme shown in FIG. 4D. Two probes 426 and 428 specifically bind to the biological target 424 of interest. In some embodiments, a portion of each of probes 426 and 428 specifically binds to the target, while each probe also has a portion that specifically binds to an adaptor 438, for example, by specific nucleic acid hybridization. In one embodiment, the probe or probes specifically hybridize to the adaptor. In cases where the biological target is a nucleic acid and the probes are oligonucleotides, the adaptor can specifically bind to the following combinations: 1) the 5' portion of probe 426 and the 3' portion of probe 428; 2) the 3' portion of probe 426 and the 5' portion of probe 428; 3) the 5' portion of probe 426 and the 5' portion of probe 428; or 4) the 3' portion of probe 426 and the 3' portion of probe 428. In certain embodiments, probe 426 or 428 is a linear molecule, a branched molecule, a circular molecule, or a combination thereof. After binding of the two probes to the biological target and the adaptor to the two probes, address tags can be delivered to the sample and coupled to the adaptor. For example, the adaptor can be tagged with address tag 430, associated with tag 434, and/or with address tag 432, associated with tag 436. Tags 434 and 436 can be universal priming sites for amplification of the assay products or sequences to enable identification of the address tags and/or other regions of adaptor/address tag conjugates, for example, using sequencing technologies. In certain embodiments, the address tags are tagged at the same end of the adaptor, or at different ends of the adaptor. In other embodiments, an address tag and/or tag 434 or 436 can be pre-coupled to the adaptor, and the adaptor/address tag or adaptor/tag conjugate or complex is then delivered to the sample in order to bind to the probe bound to the biological target. In certain aspects, the adaptor is a linear molecule, a branched molecule, a circular molecule, or a combination thereof. In some embodiments, after an address tag is attached to each end of the adaptor, the ends can be joined. For example, in FIG. 4D, address tags 434 and/or 436 can comprise structures and/or sequences that allow the two ends of the tagged adaptor 438 to be joined to form a circular construct, to facilitate amplification and/or sequencing of the construct.

In certain embodiments, all or a portion of the adaptor/address tag conjugate sequence is determined, for example, by nucleic acid sequencing. In other embodiments, all or a portion of the probe sequence, and/or all or a portion of the adaptor/address tag conjugate sequence, is determined. For example, a first address tag can be coupled to probe 426, and a second address tag can be coupled to adaptor 438. The duplex formed between probe 426 and adaptor 438 can be subjected to extension and sequencing, to generate a conjugate that comprises sequences of the first address tag, all or a portion of probe 426, all or a portion of adaptor 438, and the second address tag.

The tagging scheme is not limited to the use of two or more probes for the same biological target. For example, in cases where one probe is used, a tag (e.g., an address tag, an adaptor for ligation, or a universal sequencing primer or amplification primer sequence) can be coupled to an adaptor that specifically binds to the probe, rather than to the probe itself.

In some embodiments, at least two adaptors are used. In one aspect, more than one probes are delivered to the sample, and at least one adaptor is provided for each probe that specifically binds to the probe. In one aspect, one or more adaptors are provided for specifically binding to each probe. For example, a pair of adaptors is used to specifically bind to the probe 426 and 428, respectively. In certain embodiments, the adaptors of the pair are DNA molecules that: 1) hybridize or otherwise bind to probe 426 or 428; 2) have free 3' and/or 5' ends that enable the encoding sequences (e.g., address tags 430 and 432) to be attached in a subsequent step or steps, for example, by ligation; 3) are in a form where they can be joined if they are co-localized or in proximity to each other. In some embodiments, part of probe 426 or 428 acts as a splint to enable ligation, or extension and ligation, of the adaptors in the adaptor pair. Additional tags (e.g., an address tag, an adaptor for ligation, or a universal sequencing primer or amplification primer sequence) can be coupled to the adaptor generated by joining the adaptor pair.

FIG. 4B shows an address tagging scheme that may be used for 100 unique sites in a sample. For example, twenty probe/address tag conjugates a1 through a10 and b1 through b10 can be used, with each of a1 through a10 corresponding to a probe/address tag conjugate 420 (comprising an address tag 408) and each of b1 through b10 corresponding to a probe/address tag conjugate 422 (comprising an address tag 406). The address tag comprised in each of a1 through a10 and b1 through b10 may be uniquely identified. Probe/address tag conjugate a1, for example, is delivered to the biological sample through an addressing channel shown as the first horizontal channel in 412. Probe/address tag conjugate a2 is delivered to the biological sample through the second horizontal channel in 412. Probe/address tag conjugate a3 is delivered to the biological sample through the third horizontal channel in 412, and so on. Whereas the "a" probe/address tag conjugates are delivered in ten horizontal channels, the "b" probe/address tag conjugates are delivered in ten vertical channels as shown in 414. For example, probe/address tag conjugate b1 is delivered to the biological sample through the first horizontal channel of 414, probe/address tag conjugate b2 is delivered to the biological sample through the second horizontal channel of 414, and so on. In other embodiments, the "a" tags may be referred to as the "X" tags and the "b" tags as "Y" tags. The intersections or junctions between the horizontal and vertical channels are shown as solid squares. Each intersection or junction can be uniquely identified by the combination of the "a" probe/address tag conjugate and the "b" probe/address tag conjugate delivered to the area in the sample corresponding to the intersection or junction.

FIG. 4C shows a representative tissue section 416 coincident with grid 418. The arrows show how the "a" probe/address tag conjugates and the "b" probe/address tag conjugates are delivered on grid 418 that is coincident with tissue section 416. If, once analyzed, probe/address tag conjugates a1 and b4, e.g., are associated with a target, then that target is present in the tissue section at location (a1, b4).

Figure 5:
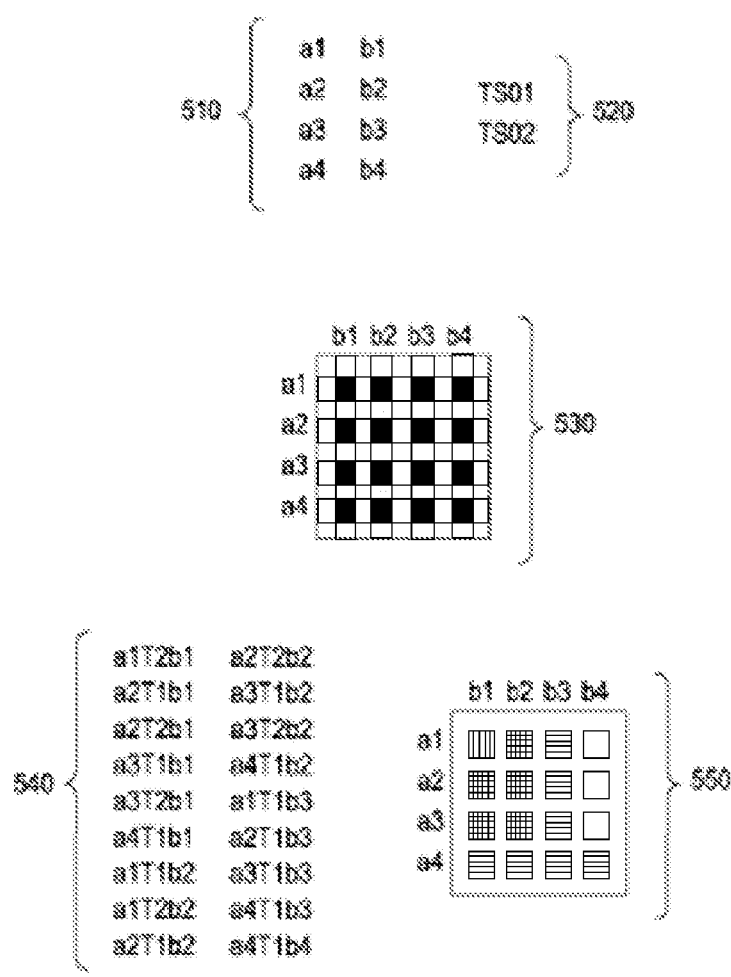
FIG. 5 illustrates a combinatorial addressing scheme applied to a sample, according to one embodiment of the present disclosure.

The methods and assay systems disclosed herein are capable of multiplexing. For example, FIG. 5 provides an address tagging (or "address coding") scheme used in a multiplexed assay. For clarity, two probes TS01 and TS02, specific for target 1 and target 2, respectively, are shown at 520. FIG. 5 shows address tags 510, comprising a1, a2, a3, a4 and b1, b2, b3 and b4. A delivery or dispensing scheme is shown at 530. Like the grid exemplified in FIG. 4, a1 through a4 are delivered to the sample through horizontal channels, and b1 through b4 are delivered to the sample through vertical channels. The intersections between the horizontal and vertical channels are shown as solid squares. Each intersection can be uniquely identified by the combination of the "a" probe/address tag conjugate and the "b" probe/address tag conjugate delivered to the area in the sample corresponding to the intersection.

Probes TS01 and TS02 are delivered to the biological sample and allowed to interact with the entire sample. Probes TS01 and TS02 specifically bind to their corresponding targets if the targets are present in the sample. Unbound probes are then removed, for example, by washing. Address tags 510 are then delivered to the biological sample according to the spatial pattern shown at 530. The address tags are coupled, for example, by ligation (or by extension followed by ligation), to probes that specifically bind to the biological target 1 or biological target 2 in the sample. The coupled constructs (or "probe/address tag conjugates") are then eluted from the biological sample and pooled. In certain embodiments, sequencing adaptors may be added through, e.g., PCR or ligation, if the sequencing adaptors are not already included in the address tags or probe/address tag conjugates. The probe/address tag conjugates are sequenced by, e.g., high throughput or next generation sequencing.

The pool of resulting assay products is shown at 540. For example, presence of the "a1T2b1" product in the pool indicates readout is obtained for TS02 at position (a1, b1) and therefore target 2 is detected at position (a1, b1). Thus, a sequence readout is obtained for only TS01 at positions (a4, b1), (a4, b2), (a1, b3), (a2, b3), (a3, b3), (a4, b3) and (a4, b4) (positions shown with horizontal lines in spatial pattern 550), and a sequence readout is obtained for TS02 only at position (a1, b1) (position shown with vertical lines in spatial pattern 550). A sequence readout is obtained for both TS01 and TS02 at positions (a2, b1), (a3, b1), (a1, b2), (a2, b2), and (a3, b2) (positions shown with cross-hatching in spatial pattern 550). No sequence readout is obtained for either TS01 or TS02 at (a1, b4), (a2, b4) or (a3, b4) (positions shown without shading in spatial pattern 550). Thus, in the biological sample, target 1 is detected in a large portion of the left side and at the bottom of the sample, while target 2 is detected only in the upper left portion of the sample, and neither target is detected in the upper right portion of the biological sample. The differential expression of the two biological targets may be mapped back to the biological sample and to the biological structures or cell types in these locations in the biological sample.

In addition to location information, relative abundance of the biological targets across the multiple sites in the sample can be obtained. For example, if it is found that there are ten times as many a4T1b1 sequences occurring in the data set as compared to a4T1b2 sequences, this would indicate that target 1 is ten times more abundant at location (a4, b1) than at location (a4, b2).

In the case of nucleotide analysis as shown in FIG. 3, by ligating the address tags directly to the probes, only 2n probes are needed for n targets. For example, assaying 100 different targets at 10,000 sites in a sample would require 2×100 probes and 2×100 address tags which are to be coupled to the probes. The total count of assay oligonucleotides would be only 400 (200 probes and 200 address tags), not counting universal primers. In contrast, if the address tags are not decoupled from the probes, the total count of assay oligonucleotides would be (n×X positions)+(n×Y positions), or in the above example, 20,000 oligonucleotides, not counting universal primer sequences. In other embodiments, for each site in the sample, three, four or more address tags may be used, and attached to the probes or one another by varying means and in varying combinations of steps.

In certain embodiments, it is desirable to correlate spatial patterns of a target polynucleotide expression, for example, mRNA expression patterns within a 2D sample, with histological features of the sample. In certain aspects, the histological features may include the expression pattern of a known marker for the sample, for example, a tissue-specific marker, a cell type marker, a cell lineage marker, a cell morphology marker, a cell cycle marker, a cell death marker, a developmental stage marker, a stem cell or progenitor cell marker, a marker for a differentiated state, an epigenetic marker, a physiological or pathophysiological marker, a marker for a transformed state, a cancer marker, or any combination thereof. In certain aspects, the histological feature comprises tissue morphology, for example, as indicate by the expression pattern of a protein marker. In certain embodiments, in order to obtain spatial information of the sample, e.g., histological features of the sample, expression pattern of a protein marker, and/or tissue morphology, an imaging technique can be used. For instance, immunohistochemical (IHC) and/or immunofluorescent (IF) imaging may need to be used.

In certain aspects, provided herein are methods called Spatially Encoded Protein In Situ Assays (SEPIA) for multiplexed in situ analysis of proteins. In some embodiments, SEPIA and related assay systems can obtain spatial information on the relative abundance of many proteins in tissue sections. In certain embodiments, the methods and assay systems of the present disclosure are based on the use of antibodies (or other affinity capture agents capable of specifically binding to a target, other than by nucleotide sequence complementarity) that are labeled with an identity tag that identifies the target protein or the antibody, and one or more address tags that identify the location of each of multiple sites in a sample. In one embodiment, there are provided at least two address tags for each site, one of the at least two address tags identifying the location in the tissue section in one dimension (for example, an X coordinate) and the other identifying the location in another dimension (for example, a Y coordinate).

In any of the embodiments disclosed herein, the biological target can be a peptide or a protein, and the methods or assay systems can be used to analyze the presence of antibodies, enzymatic and other protein activities, posttranslational modifications, active and non-active forms of peptides, as well as peptide isoforms in a biological sample. Accordingly, the probes may comprise an active region of an enzyme, a binding domain of an immunoglobulin, defined domains of proteins, whole proteins, synthetic peptides, peptides with introduced mutations, aptamers and the like.

In any of the embodiments disclosed herein, the probes can comprise substrates for enzymes or proenzymes, e.g., kinases, phosphatases, zymogens, proteases, or fragments thereof. In certain aspects, the probes may comprise phosphorylation substrates used to detect proteins involved in one or more signal transduction pathways. In other aspects, the probes can comprise specific protease substrates that associate with specific individual proteases or specific classes of proteases. In other aspects, the probes can comprise different processed forms, isoforms and/or domains of an enzyme. In certain embodiments, a protein-based probe can be conjugated or otherwise linked to an oligonucleotide address tag. In preferred embodiments, the oligonucleotide address tag may comprise a nucleotide sequence component that allows for identification of the protein probe.

In preferred embodiments, antibodies that are conjugated to oligonucleotide tags are compatible with the address tagging scheme disclosed herein. In certain aspects, provided herein are methods and assay systems that are highly multiplexed, scalable, and high-throughput for determining a spatial pattern of abundance and/or activity of a target protein across multiple sites in a sample, using a nucleic acid readout and independent of imaging for the target protein. In preferred embodiments, provided herein are methods and assay systems to correlate nucleic acid expression patterns (e.g., DNA or RNA expression patterns) with cell type-specific protein marker abundance without the need for imaging for the protein marker, for example, by immunohistochemical or immunofluorescent imaging. In preferred embodiments, spatial resolution of the present methods and assay systems may approach the scale of individual cells. In certain aspects, correlated 2D and 3D maps of RNA and protein abundance can be generated using the present methods and assay systems.

Figure 6:
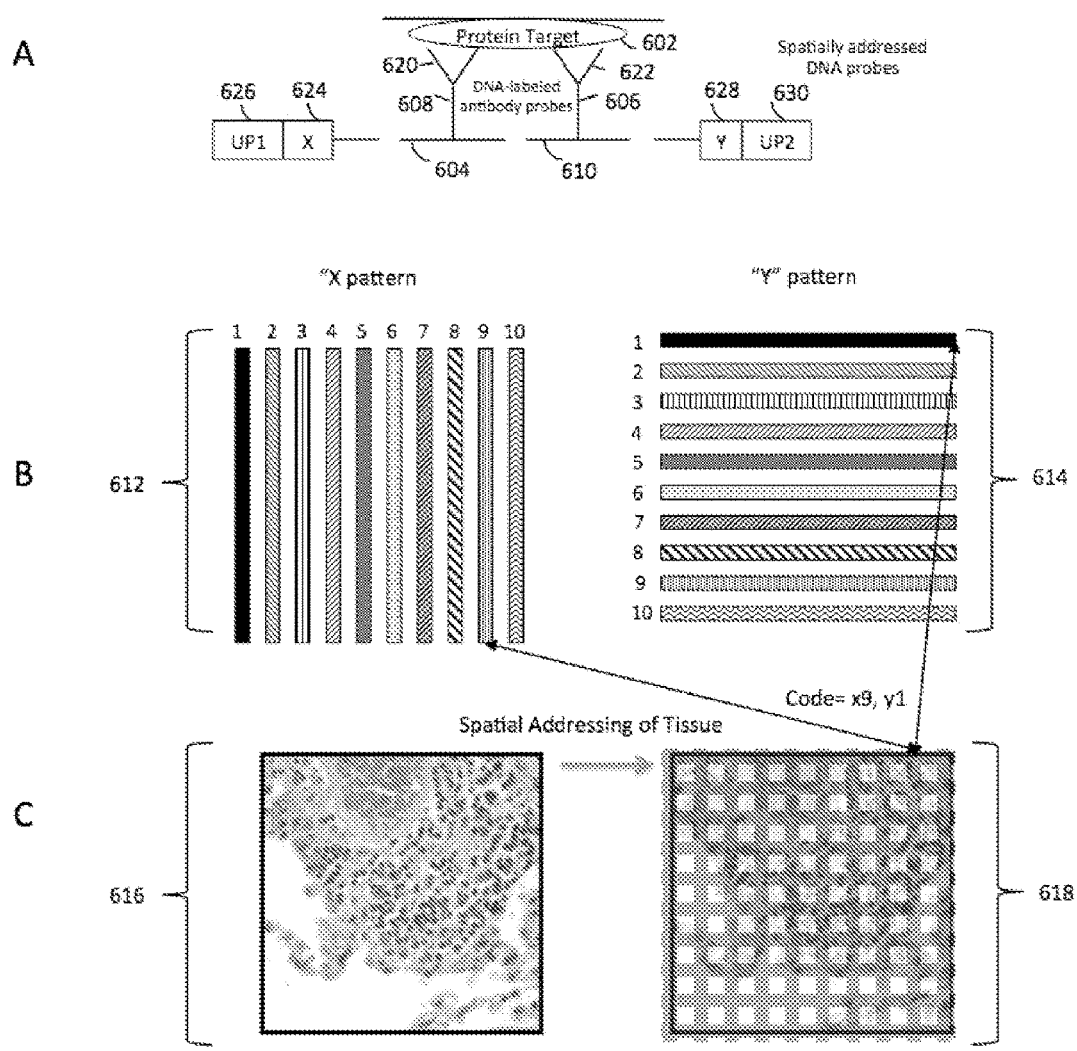
FIG. 6 illustrates multiplexable protein detection assays with combinatorial addressing schemes applied to a sample, according to embodiments of the present disclosure.

As shown in FIG. 6, in one aspect, a highly multiplexable protein detection assay is carried out on a sample 616 (shown in FIG. 6C). In preferred embodiments, sample 616 preserves the spatial organization of cells in a tissue. For example, sample 616 can be a paraffin-embedded or fresh-frozen tissue section fixed to a glass slide. FIG. 6A shows two probes 620 and 622 specifically bound to a protein target 602 of interest. The first probe 620 may comprise target-binding moiety 608, associated with oligonucleotide tag 604. Target-binding moiety 608 and oligonucleotide tag 604 can be conjugated or covalently linked. Target-binding moiety 608 can comprise any affinity capture agents, e.g., antibodies, that specifically bind to protein target 602. Probe 620 may further comprise address tag 624 and tag 626. Tag 626 can be a universal priming site for amplification of the assay products and/or an adaptor to enable identification of the address tag 624 and/or oligonucleotide tag 604 and/or other regions of probe 620, for example, using sequencing technologies. In certain embodiments, tag 626 is conjugated or linked to or otherwise associated with address tag 624, for example, by ligation, extension, ligation followed by extension, or any combination thereof. In one aspect, conjugated, linked or otherwise associated tag 626 and address tag 624 as a whole are conjugated or linked to or otherwise associated with oligonucleotide tag 604. In alternative embodiments, tag 626 and address tag 624 may be separately conjugated or linked to or otherwise associated with probe 620, for example, at target-binding moiety 608 and/or oligonucleotide tag 604.

Similarly, the second probe 622 may comprise target-binding moiety 606, associated with oligonucleotide tag 610. Target-binding moiety 606 and oligonucleotide tag 610 can be conjugated or covalently linked. Target-binding moiety 606 can comprise any affinity capture agents, e.g., antibodies, that specifically bind to protein target 602. Probe 622 may further comprise address tag 628 and tag 630. Tag 630 can be a universal priming site for amplification of the assay products and/or an adaptor to enable identification of the address tag 628 and/or oligonucleotide tag 610 and/or other regions of probe 622, for example, using sequencing technologies. In certain embodiments, tag 630 is conjugated or linked to or otherwise associated with address tag 628, for example, by ligation, extension, ligation followed by extension, or any combination thereof. In one aspect, conjugated, linked or otherwise associated tag 630 and address tag 628 as a whole are conjugated or linked to or otherwise associated with oligonucleotide tag 610. In alternative embodiments, tag 630 and address tag 628 may be separately conjugated or linked to or otherwise associated with probe 622, for example, at target-binding moiety 606 and/or oligonucleotide tag 610.

In certain embodiments, target-binding moiety 606 and target-binding moiety 608 bind to adjacent sites on target 602, so that two free ends of oligonucleotide tags 604 and 610 are brought close to each other. In one embodiment, oligonucleotide tags 604 and 610 may be ligated and the ligation product assayed. In other embodiments, one or both of oligonucleotide tags 604 and 610 may be extended and then ligated to the other probe to form an extended probe comprising target target-binding moiety 606 and target-binding moiety 608. For example, a DNA ligase may be added together with a splint to join two free ends of oligonucleotide tags 604 and 610, and the DNA ligated product can serve as the template detectable by real-time PCR and/or various sequencing technologies. Such a dual targeting approach may be used to increase assay specificity. Other aspects and embodiments of the dual targeting approach that converts specific protein detection into nucleic acid analysis, including the proximity ligation assay described in Fredriksson et al., 2002, Nat Biotechnol 20, 473-7, may be used in the methods and assay systems of the present disclosure. It is also within the present disclosure that in certain embodiments, target-binding moiety 606 and target-binding moiety 608 may bind to different protein targets. When the protein targets are in close proximity, for example, when the two are in the same complex or brought into contact with each other in a reaction, a ligation product may be formed between oligonucleotide tags 604 and 610 and detected.

In certain embodiments, a primary antibody and a secondary antibody may be used. For example, target-binding moiety 606 and/or target-binding moiety 608, instead of specifically binding to target 602 directly, may specifically bind to a primary antibody that specifically recognizes target 602. In this case, target-binding moiety 606 and/or target-binding moiety 608 may be comprised in a secondary antibody. In certain aspects, the approach involving a primary antibody and a secondary antibody may be suitable when target expression in low in a sample, because one molecule of target 602 may be able to bind multiple molecules of a primary antibody, thereby amplifying the signal.

In other embodiments, a biological target 632 is assayed according to the combinatorial address tagging scheme shown in FIG. 6D. Two probes 650 and 652 specifically bind to the biological target 632 of interest. In one embodiment, the first probe 650 comprises target-binding moiety 638, associated with oligonucleotide tag 634, and the second probe 652 comprises target-binding moiety 636, associated with oligonucleotide tag 640. Target-binding moiety 638 and oligonucleotide tag 634 (or target-binding moiety 636 and oligonucleotide tag 640) can be conjugated or covalently linked. In particular embodiments, target-binding moiety 638 or 636 comprises an affinity capture agent, e.g., an antibody, that specifically binds to target 632. In certain embodiments, target 632 comprises a protein moiety, an oligosaccharide or polysaccharide moiety, a fatty acid moiety, and/or a nucleic acid moiety. In some embodiments, each probe has a portion that specifically binds to an adaptor 662, for example, by specific nucleic acid hybridization. In one embodiment, oligonucleotide tag 634 or 640 (or a portion thereof) specifically hybridizes to the adaptor. The adaptor can specifically bind to the following combinations: 1) the 5' portion of oligonucleotide tag 634 and the 3' portion of oligonucleotide tag 640; 2) the 3' portion of oligonucleotide tag 634 and the 5' portion of oligonucleotide tag 640; 3) the 5' portion of oligonucleotide tag 634 and the 5' portion of oligonucleotide tag 640; or 4) the 3' portion of oligonucleotide tag 634 and the 3' portion of oligonucleotide tag 640. In certain embodiments, oligonucleotide tag 634 or 640 is a linear molecule, a branched molecule, a circular molecule, or a combination thereof. After binding of the two probes to the biological target and the adaptor to the two probes, address tags can be delivered to the sample and coupled to the adaptor. For example, the adaptor can be tagged with address tag 654, associated with tag 656, and/or with address tag 658, associated with tag 660. Tags 656 and 660 can be universal priming sites for amplification of the assay products or sequences to enable identification of the address tags and/or other regions of adaptor/address tag conjugates, for example, using sequencing technologies. In certain embodiments, the address tags are tagged at the same end of the adaptor, or at different ends of the adaptor. In other embodiments, an address tag and/or tag 656 or 660 can be pre-coupled to the adaptor, and the adaptor/address tag or adaptor/tag conjugate or complex is then delivered to the sample in order to bind to the probe bound to the biological target.

In certain embodiments, all or a portion of the adaptor/address tag conjugate sequence is determined, for example, by nucleic acid sequencing. In other embodiments, all or a portion of the oligonucleotide tag sequence, and/or all or a portion of the adaptor/address tag conjugate sequence, is determined. For example, a first address tag can be coupled to oligonucleotide tag 634, and a second address tag can be coupled to adaptor 662. The duplex formed between oligonucleotide tag 634 and adaptor 662 can be subjected to extension and sequencing, to generate a conjugate that comprises sequences of the first address tag, all or a portion of oligonucleotide tag 634, all or a portion of adaptor 662, and the second address tag.

The tagging scheme is not limited to the use of two or more probes for the same biological target. For example, in cases where one probe is used, a tag (e.g., an address tag, an adaptor for ligation, or a universal sequencing primer or amplification primer sequence) can be coupled to an adaptor that specifically binds to the probe, rather than to the probe itself.

Additional details of the polynucleotide-protein conjugates used in the present disclosure are disclosed in U.S. Provisional Patent Application Ser. No. 61/902,105, filed Nov. 8, 2013, entitled "Polynucleotide conjugates and methods for analyte detection," the disclosure of which is incorporated by reference in its entirety for all purposes.

In some embodiments, more than one adaptor is used. For example, a pair of adaptors is used to specifically bind the oligonucleotide tag 634 and 640, respectively. In certain embodiments, the adaptors of the pair are DNA molecules that: 1) hybridize or otherwise bind to the protein-DNA conjugates, for example, probe 650 or 652; 2) have free 3' and/or 5' ends that enable the encoding sequences (e.g., address tags 654 and 658) to be attached in a subsequent step or steps, for example, by ligation; 3) are in a form where they can be joined if they are co-localized or in proximity to each other. In some embodiments, part of the oligonucleotide portion of probe 650 or 652 acts as a splint to enable ligation, or extension and ligation, of the adaptors in the adaptor pair. Additional tags (e.g., an address tag, an adaptor for ligation, or a universal sequencing or amplification primer sequence) can be coupled to the adaptor generated by joining the adaptor pair.

In another embodiment, a method disclosed herein makes it easier to carry out protein-based assays at the same time as nucleic-acid based assays. For example, the adaptors can be designed so that they are compatible with the same encoding oligonucleotides used for the nucleic-acid based assays, e.g., RNA-based assays. Thus, two types of binding assays (i.e., detecting a protein target using a protein-polynucleotide conjugate, and detecting a nucleic acid target using a nucleic acid probe) can be carried out in the same reaction volume or in the same experimental run, and the spatial addressing can be performed on both types of probes simultaneously.

In yet another embodiment, the present disclosure provides a control for assays detecting a protein target or a biological target comprising a protein moiety. For example, the nucleic acid portion of the protein-nucleic acid conjugate is used to hybridize to a nucleic acid in the sample. This anchors an "artificial" protein (known composition and abundance based on the abundance of the hybridizing sequence) in the sample. The "artificial" protein can then be detected using a number of means, including protein-binding spatially-addressed assays disclosed herein. The approach is not limited to proteins. For example, small molecules, such as haptens, can also be used. In one aspect, FIG. 6E illustrates the general concept of a method of detecting an RNA with known composition and abundance in the sample, thereby providing a control for the detection of other targets (e.g., protein targets) in the sample. In FIG. 6E, conjugates 662 and 664 each comprises a nucleic acid portion and an antibody-binding portion (circle indicates the antibody-binding portion of conjugate 662, and triangle indicates the antibody-binding portion of conjugate 664). In certain aspects, RNA 666 with known composition and abundance in the sample is specifically bound by the nucleic acid portions of conjugates 662 and 664. In some embodiments, the composition and/or abundance of RNA 666 are determined experimentally, for example, using a method of the present disclosure, and in specific embodiments, simultaneously with the detection of the protein target. In other embodiments, the composition and/or abundance of RNA 666 is derived from prior knowledge or knowledge in the art. In particular embodiments, the antibody-binding portions can be HA or FLAG, and the antibody portions of probes 650 and 652 can be an anti-HA antibody or an anti-FLAG antibody, for example, polyclonal or monoclonal antibodies. Other protein-antibody binding pairs are known in the art and can be used in the present disclosure.

FIG. 6B shows an address tagging scheme that may be used for 100 unique sites in a sample. For example, twenty probes/address tag conjugates X1 through X10 and Y1 through Y10 can be used, with each of X1 through X10 comprising an address tag 624 and each of Y1 through Y10 comprising an address tag 628. The address tag comprised in each of X1 through X10 and Y1 through Y10 may be uniquely identified. Probe/address tag conjugate X9, for example, is delivered to the biological sample in the ninth vertical channel in 612. Whereas the "X" probe/address tag conjugates are delivered in ten vertical channels, the "Y" probe/address tag conjugates are delivered in ten horizontal channels as shown in 614. For example, probe/address tag conjugate Y1 is delivered to the biological sample in the first horizontal channel of 614. In other embodiments, the "X" tags may be referred to as the "a" tags and the "Y" tags as "b" tags.

FIG. 6C shows a representative tissue section 616 coincident with grid 618. The arrows show how the "X" probe/address tag conjugates and the "Y" probe/address tag conjugates are delivered on grid 618 that is coincident with tissue section 616. If, once analyzed, probe/address tag conjugates X9 and Y1, e.g., are associated with a target, then that target is present in the tissue section at location (X9, Y1).

Figure 7:
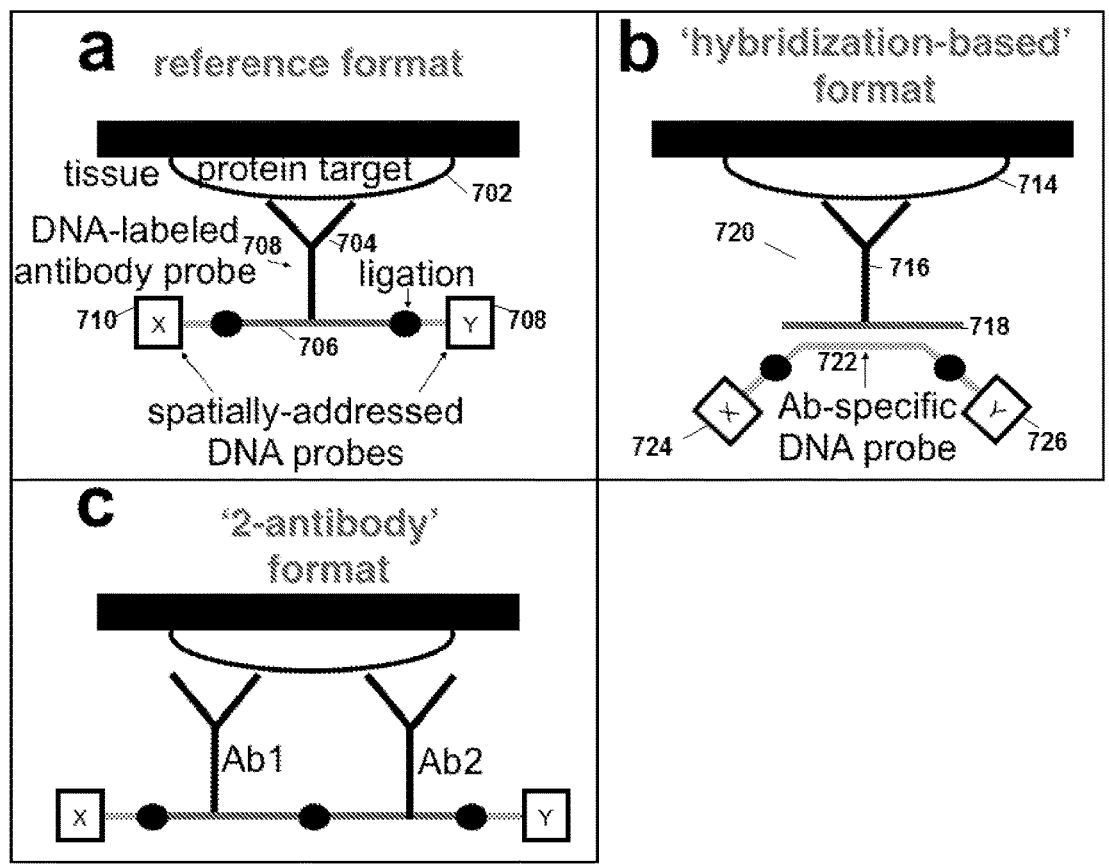
FIG. 7 illustrates exemplary antibody-DNA conjugate configurations, according to certain embodiments of the present disclosure.

Any suitable configuration of the oligonucleotide/antibody (or other target-specific binder) conjugate may be used to convert specific protein detection into nucleic acid analysis. In certain embodiments, for example, as shown in FIG. 7A, probe 708 specifically binds to protein target 702. Probe 708 may comprise target-binding moiety 704, associated with oligonucleotide tag 706. Target-binding moiety 704 and oligonucleotide tag 706 can be conjugated or covalently linked. Target-binding moiety 704 can comprise any affinity capture agents, e.g., antibodies, that specifically bind to protein target 702. Probe 708 may further comprise "X" address tag 710 and "Y" address tag 712. Both address tags 710 and 712 may be conjugated to a universal priming site for amplification of the assay products and/or an adaptor (not shown in FIG. 7) to enable identification of the address tags 710 and 712 and/or oligonucleotide tag 706 and/or other regions of probe 708, for example, using sequencing technologies. Conjugation of the various tags may be accomplished by ligation, extension, ligation followed by extension, or any combination thereof. In some embodiments, address tags 710 and 712 are conjugated to one side of oligonucleotide tag 706 or the other (i.e., 5' or 3' of the sequence), respectively. In alternative embodiments, both address tags 710 and 712 may be conjugated to either 5' or 3' of oligonucleotide tag 706. For example, address tags 710 and 712 may be directly or indirectly conjugated, and address tag 710 or 712 may be directly or indirectly conjugated to either 5' or 3' of oligonucleotide tag 706.

In other embodiments, for example, as shown in FIG. 7B, probe 720 specifically binds to protein target 714. Probe 720 may comprise target-binding moiety 716, conjugated, linked, or otherwise associated with oligonucleotide tag 718. Target-binding moiety 716 can comprise any affinity capture agents, e.g., antibodies, that specifically bind to protein target 714. Probe 720 may further comprise oligonucleotide sequence 722 that specifically hybridizes to oligonucleotide tag 718. In one embodiment, sequence 722 is complementary to oligonucleotide tag 718. Sequence 722 may be conjugated to "X" address tag 724 and "Y" address tag 726. Both address tags 724 and 726 may be conjugated to a universal priming site for amplification of the assay products and/or an adaptor (not shown in FIG. 7) to enable identification of the address tags 724 and 726 and/or sequence 722 and/or other regions of probe 720, for example, using sequencing technologies. Conjugation of the various tags may be accomplished by ligation, extension, ligation followed by extension, or any combination thereof. Similar to FIG. 7A, address tags 724 and/or 726 can be conjugated to either side of oligonucleotide sequence 722 (i.e., 5' or 3' of the sequence), either directly or indirectly.

In further embodiments, for example, as shown in FIG. 7C, a "2-antibody" format may be used. The "2-antibody" format is similar to the dual targeting approach discussed above, for example, in FIG. 6. In this embodiment, two antibodies specific for a protein target are conjugated to an oligonucleotide, which can be directly or indirectly conjugated to the "X" and "Y" address tags and a universal priming site for amplification of assay products and/or an adaptor for sequencing. In some embodiments, the two antibodies may bind to different epitopes or sites on the protein target. In preferred embodiments, binding of both antibodies to the target is required to generate a signal, thus providing higher specificity than using only one antibody. It is also contemplated that more than two antibodies may be conjugated to an oligonucleotide and used in the methods and assay systems of the present disclosure.

As disclosed herein, the methods and assay systems permit high levels of multiplexing. In one embodiment, the probes can be delivered over the entire surface of a 2D sample in a bulk process, and then address tagged by delivering the address tags in a spatially defined pattern. For example, two sets of address tags (the "X" and "Y" tags) can be used in a combinatorial fashion as discussed supra. Once the in situ assay is completed, the assay products are eluted and sequenced. The address tag sequence information identifies the location at which the assay is performed, and the probe sequence information (the identity tag) identifies the protein that is targeted. In one aspect, the frequency of a particular assay product (for example, a sequencing product) in the digital readout can be used to infer the relative abundance of its target in the sample. This information can then be associated with other information, including conventional histological information, and/or transcript abundance obtained via the related Spatially Encoded Genomic Assays (SEGA). In preferred embodiments, the methods and assay systems do not depend on an imaging technique for the spatial information of the target protein. Instead, in preferred embodiments, the spatial pattern of the target protein abundance and/or activity can be determined by sequencing.

In one embodiment, in order to integrate the protein and gene expression assays, the same address tagging scheme is compatible with and can be used for both assay types. For example, for each of multiple sites in a sample, the same combination of "X" and "Y" address tags can be tagged to an antibody-DNA conjugate for a target protein, and to a probe for a target polynucleotide sequence. In one embodiment, the target polynucleotide or the complement thereof encodes all or a portion of the target protein. Therefore, for each site in the sample, the abundance and/or activity of the target protein and its corresponding polynucleotide can be detected by assaying for sequencing products with the same set of address tags. In preferred embodiments, the step of analyzing probes or probe/address tag conjugates bound to the target protein and the step of analyzing probes or probe/address tag conjugates bound to the target polynucleotide can be performed in parallel in the same reaction run. In alternative embodiments, different address tags may be coupled to an antibody-DNA conjugate for a target protein, and to a probe for a target polynucleotide sequence, to determine the abundance and/or activity of the target protein and the target polynucleotide at a given site. Assay results for the target protein and the target polynucleotide can then be integrated for each site in the sample.

The methods and assay systems disclosed herein are particularly suitable for generating a large amount of information with even a modest number of assays. For example, five or more biological targets assayed at five or more positions in the sample generates 25 or more combinations. Using digital sequencing as a readout, the optimum number of sequence reads per combination depends on the sensitivity and dynamic range required, and can be adjusted. For example, if for each combination on average 100 reads are sampled, the total for 25 combination is 2,500 reads. If 1,000 targets are assayed at 1,000 locations with an average sampling depth of 1,000, then $10^9$ reads are required. These numbers, although large, are within the capacity of intrinsically parallel digital sequencing methods, which can generate datasets of billions or even trillions of reads in a reasonable timeframe and at a very low cost per read. Therefore, by varying the numbers of positions or biological targets assayed, or both, and using digital sequencing, large amounts of information can be obtained. In specific aspects, multiple locations are assayed for two or more biological molecules.

Thus, provided herein is an ability to look at many different biological targets in many locations of a sample at the same time, for example, in the same reaction run. In some embodiments, the product of the multiple biological targets being assayed and the multiple sites in the biological sample is greater than about 20. In other embodiments, the product of the multiple biological targets being assayed and the multiple sites in the biological sample is greater than about 50. In other embodiments, the product of the multiple biological targets being assayed and the multiple sites in the biological sample is greater than about 100, greater than about 500, greater than about 1,000, greater than about 10,000, greater than about 25,000, greater than about 100,000, greater than about 500,000, or greater than about 1,000,000. It will be appreciated that even much larger numbers can be contemplated. For example, assaying 10,000 targets per location for 10,000 locations in a sample would generate $10^8$ different assays. In some embodiments, sufficient numbers of sites in a sample can be assayed to reach a resolution on the order of that of single cells. Further, in embodiments where high-throughput digital sequencing is employed, the sequences of at least 1,000 probes or probe/address tag conjugates are typically determined in parallel. More typically, using a digital readout, it is desirable to obtain multiple sequence reads for each assay (defined by a target and a location, i.e., by the identities of an identity tag and an address tag of a target). It is desirable to obtain an average of at least 3 copies per assay, and more typically at least 10 or at least 30 copies per assay, depending on the design of the experiment and requirements of the assay. For a quantitative readout with suitable dynamic range, it may be desirable to obtain at least 1,000 reads per assay. Therefore, if 1,000,000 assays are carried out, the number of sequence reads may be 1 billion or more. With high-throughput digital sequencing, and allowing for redundancy, the sequence of at least 10,000 probes or probe/address tag conjugates can be determined in parallel, or the sequence of at least 100,000, 500,000, 1,000,000, 10,000,000, 100,000,000, 1,000,000,000 or more probes or probe/address tag conjugates can be determined in parallel.

In certain aspects, disclosed herein are methods and assay systems for evaluating differences in the amount and/or activity of biological targets between different locations in a sample and/or between samples. In one embodiment, the method comprises evaluating the differences in quantity of the biological targets at each location in the biological sample. In another embodiment, the method comprises comparing spatial patterns of abundance and/or activity of one or more biological targets among multiple samples.

Methods and assays systems to determine a spatial pattern of abundance and/or activity of a biological target in a sample are disclosed in detail in U.S. Application Ser. No. 61/839,313, filed Jun. 25, 2013, entitled "Methods and systems for determining spatial patterns of biological targets in a sample," U.S. application Ser. No. 13/080,616, entitled "Spatially encoded biological assays" (Pub. No.: US 2011/0245111), and in International Application No. PCT/US2014/044196, filed Jun. 25, 2014, entitled "Methods and systems for determining spatial patterns of biological targets in a sample," the disclosures of which are incorporated herein by reference for all purposes.

Spatially Encoded Biological Assays Using Microfluidic Device

The reagent delivery system of the present disclosure includes instrumentation that allows the delivery of reagents to discrete portions of the biological sample, maintaining the integrity of the spatial patterns of the addressing scheme. Reagent delivery systems of the present assay systems comprise optional imaging means, reagent delivery hardware and control software. Reagent delivery can be achieved in a number of different ways. It should be noted that reagents may be delivered to many different biological samples at one time. A single tissue section has been exemplified herein; however, multiple biological samples may be manipulated and analyzed simultaneously. For example, serial sections of a tissue sample can be analyzed in parallel and the data combined to build a 3D map.

Integral to the assay system of the present disclosure is instrumentation that allows for spatial patterning of reagents onto the biological sample. Technologies for formulating and delivering both biological molecules (e.g. oligonucleotides or antibodies) and chemical reagents (e.g., small molecules or dNTPs) are known in the art, and uses of these instrument systems are known to one skilled in the art and easily adaptable to the assay systems of the present disclosure. One example of a suitable reagent delivery system is the Labcyte™ Echo acoustic liquid handler, which can be used to deliver nanoliter scale droplets containing biological molecules with high precision and reproducibility. One skilled in the art could incorporate this reagent delivery device into the overall system using software to specify the locations to which reagents should be delivered.

In certain embodiments, it may be preferred to segment or sequester certain areas of the biological samples into one or more assay areas for different reagent distributions and/or biological target determination. The assay areas may be physically separated using barriers or channels.

In one exemplary aspect, the reagent delivery system may be a flow-based system. The flow-based systems for reagent delivery in the present invention can include instrumentation such as one or more pumps, valves, fluid reservoirs, channels, and/or reagent storage cells. Reagent delivery systems are configured to move fluid to contact a discrete section of the biological sample. Movement of the reagents can be driven by a pump disposed, for example, downstream of the fluid reagents. The pump can drive each fluid reagent to (and past) the reaction compartment. Alternatively, reagents may be driven through the fluid by gravity. US Pub. Nos. 20070166725 and 20050239192 disclose certain general purpose fluidics tools that can be used with the assay systems of the present disclosure, allowing for the precise manipulation of gases, liquids and solids to accomplish very complex analytical manipulations with relatively simple hardware.

In a more specific example, one or more flow-cells can be attached to the substrate-affixed biological sample from above. The flow-cell can include inlet and outlet tubes connected thereto and optionally an external pump is used to deliver reagents to the flow-cell and across the biological sample. The flow cells are configured to deliver reagents only to certain portions of the biological sample, restricting the amount and type of reagent delivered to any specific section of the biological sample.

In another aspect, a microfluidic system can be integrated into the substrate upon which the biological sample is disposed or externally attached on top of the substrate. Microfluidic passages for holding and carrying fluid may be formed on and/or above the planar substrate by a fluidics layer abutted to the substrate. Fluid reagents can be selected and delivered according to selective opening and closing of valves disposed between reagent reservoirs.

Pumps generally include any mechanism for moving fluid and/or reagents disposed in fluid. In some examples, the pump can be configured to move fluid and/or reagents through passages with small volumes (i.e., microfluidic structures). The pump can operate mechanically by exerting a positive or negative pressure on fluid and/or on a structure carrying fluid, electrically by appropriate application of an electric field(s), or both, among other means. Exemplary mechanical pumps may include syringe pumps, peristaltic pumps, rotary pumps, pressurized gas, pipettors, etc. For example, external syringes and pneumatic pumps may be used to inject fluids and generate fluid flow within microfluidic devices. Another type of pump that may be used is a capillary pump that works on the principle of a fluid filling a set of thin capillaries. As such, a capillary pump provides a single-pass capability. Since a capillary pump can be completely passive, the flow of fluid can be "hardwired" into the design. Mechanical pumps may be micromachined, molded, etc. Exemplary electrical pumps may include electrodes and may operate by electrophoresis, electroendosmosis, electrocapillarity, dielectrophoresis (including traveling wave forms thereof), and/or the like. In one embodiment, a thumb-driven peristaltic mechanism can be used to drive liquid through the addressing channels. In alternative embodiments, the loading mechanism can be by centrifugation. In one aspect, loading by centrifugation is scalable.

Valves generally include any mechanism for regulating the passage of fluid through a chatmel. Valves can include, for example, deformable members that can be selectively deformed to partially or completely close a channel, a movable projection that can be selectively extended into a channel to partially or completely block a channel, an electrocapillary structure, and/or the like.

An open gasket can be attached to the top of the biological sample and the sample and reagents can be injected into the gasket. Suitable gasket materials include, but are not limited to, neoprene, nitrile, and silicone rubber. Alternatively, a watertight reaction chamber may be formed by a gasket sandwiched between the biological sample on the substrate and a chemically inert, water resistant material such as, but not limited to, black-anodized aluminum, thermoplastics (e.g., polystyrene, polycarbonate, etc.), glass, etc.

Embodiments of the present disclosure may comprise integrated pumps, valves, and fluid actuators, to enable complex and versatile microfluidic networks. Each addressing channel may contain one, more than one, or no fluid actuator. Fluid actuators integrated within microfluidic device at asymmetric locations can generate both unidirectional and bidirectional fluid flow through the channels. Selective activation of multiple fluid actuators located asymmetrically toward the ends of multiple microfluidic addressing channels enables the generation of arbitrary and/or directionally-controlled fluid flow patterns. In addition, temporal control over the mechanical operation or motion of a fluid actuator enables directional control of fluid flow through an addressing channel. Thus, in some embodiments precise control over the forward and reverse strokes (i.e., compressive and tensile fluid displacements) of a single fluid actuator can provide bidirectional fluid flow within an addressing channel and generate arbitrary and/or directionally-controlled fluid flow patterns within the channel.

The fluid actuators can be driven by a variety of actuator mechanisms such as thermal bubble resistor actuators, piezo membrane actuators, electrostatic (MEMS) membrane actuators, mechanical/impact driven membrane actuators, voice coil actuators, magnetostrictive drive actuators, and so on. The fluid actuators can be integrated into microfluidic device systems using conventional micro-fabrication processes. This enables complex microfluidic devices having arbitrary pressure and flow distributions. The microfluidic devices may also include various integrated active elements such as resistive heaters, Peltier coolers, physical, chemical and biological sensors, light sources, and combinations thereof. The microfluidic devices may or may not be connected to external fluid reservoirs. Advantages of the disclosed microfluidic devices and networks generally include a reduced amount of equipment needed to operate microfluidic systems, which increases mobility and widens the range of potential applications in the methods and assay systems disclosed herein.

Figure 8:
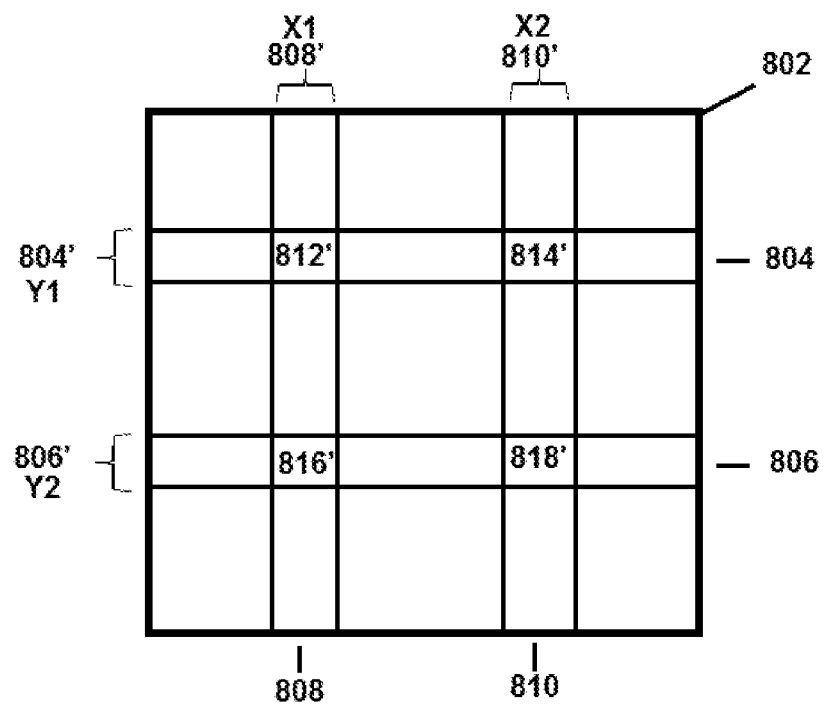
FIG. 8 illustrates a microfluidic device based reagent delivery and address tagging scheme, according to one embodiment of the present disclosure.

Provided herein is a method of determining a spatial pattern of abundance and/or activity of a biological target in a sample using a microfluidic device. Basic components, structures, and mechanisms of microfluidic devices are discussed supra, and are known to one of skill in the art. The method comprises delivering a probe for a biological target to a sample, the probe comprising: (1) a binding moiety capable of binding to the biological target; and (2) an identity tag that identifies the biological target or the binding moiety. As shown in FIG. 8, after delivering the probe to sample 802 and allowing the probe to interact with its biological target, sample 802 is affixed to a first microfluidic device having multiple first addressing channels 804 and 806, wherein each first addressing channel identifies a first area (804' and 806', respectively) in the sample. Two first addressing channels are shown in FIGS. 8-11 for illustrative purposes only, and it should be understood that more first addressing channels may be used. A first address tag is then delivered through each of the first addressing channels to each first area in the sample, wherein each first address tag is to be coupled to the probe. For example, in FIG. 8, address tag Y1 is delivered through first addressing channel 804 to first area 804', and address tag Y2 is delivered through first addressing channel 806 to first area 806'. Sample 802 with the delivered first address tags Y1 and Y2 is then affixed to a second microfluidic device. In certain embodiments, first address tags Y1 and Y2 are coupled to probes bound to biological targets in first areas 804' and 806', respectively, before sample 802 is optionally washed (to separate address tags not coupled to probes bound to targets) and affixed to a second microfluidic device. In alternative embodiments, first address tags Y1 and Y2 are delivered to the sample, and are not coupled to probes until second address tags X1 and X2 are delivered and coupled to probes, as discussed infra.

The second microfluidic device comprises multiple second addressing channels 808 and 810, wherein each second addressing channel identifies a second area (808' and 810', respectively) in the sample. Two second addressing channels are shown in FIGS. 8-11 for illustrative purposes only, and it should be understood that more second addressing channels may be used. In certain embodiments, second areas 808' and 810' intersect with first areas 804' and 806' at an angle greater than 0 degree, for example, at about 90 degrees as shown in FIG. 8. A second address tag is then delivered through each of the second addressing channels to each second area in the sample, wherein each second address tag is to be coupled to the probe. For example, in FIG. 8, address tag X1 is delivered through second addressing channel 808 to second area 808', and address tag X2 is delivered through second addressing channel 810 to second area 810'. Address tags X1 and X2 are then coupled to probes bound to biological targets in second areas 808' and 810', respectively. In this illustrative example, four intersections are formed between the first and second areas: 812', 814', 816', and 818'. In certain embodiments, before second address tags are delivered, probes bound to targets at intersection 812' and 814' have already been coupled with first address tag Y1, and probes bound to targets at intersection 816' and 818' have already been coupled with first address tag Y2. Therefore, in these embodiments, second address tag X1 is to be coupled to probes already coupled with first address tags Y1 (at intersection 812') and Y2 (at intersection 816'), and second address tag X2 is to be coupled to probes already coupled with first address tags Y1 (at intersection 814') and Y2 (at intersection 818'). Therefore, intersections 812', 814', 816', and 818' can be identified at location (X1, Y1), (X2, Y1), (X1, Y2), and (X2, Y2), respectively, in sample 802. The method further comprises analyzing probes bound to the biological target, including determining an expression and/or activity of the biological target and the identities of the identity tag and the first and second address tags at each address. Thus, this reagent delivery and address tagging scheme is compatible with methods and assays described supra.

The reagent delivery and address tagging scheme based on microfluidic device is also compatible with probes preassembled with address tags. For example, in FIG. 9, sample 902 is affixed to a first microfluidic device having multiple first addressing channels 904 and 906, wherein each first addressing channel identifies a first area (904' and 906', respectively) in the sample. A probe with a first address tag already installed is then delivered through each of the first addressing channels to each first area in the sample. For example, in FIG. 9, a probe with address tag Y1 ("P-Y1") is delivered through first addressing channel 904 to first area 904', and the same probe with address tag Y2 ("P-Y2") is delivered through first addressing channel 906 to first area 906'. Sample 902 with the delivered P-Y1 and P-Y2 probes is then affixed to a second microfluidic device comprising multiple second addressing channels 908 and 910, wherein each second addressing channel identifies a second area (908' and 910', respectively) in the sample. A second address tag is then delivered through each of the second addressing channels to each second area in the sample, wherein each second address tag is to be coupled to the probe. For example, in FIG. 9, address tag X1 is delivered through second addressing channel 908 to second area 908', and address tag X2 is delivered through second addressing channel 910 to second area 910'. Address tags X1 and X2 are then coupled to probes bound to biological targets in second areas 908' and 910', respectively. In this illustrative example, four intersections are formed between the first and second areas: 912', 914', 916', and 918', comprising probes with the coupled second address tags X1-P-Y1, X2-P-Y1, X1-P-Y2, and X2-P-Y2, respectively. Therefore, intersections 912', 914', 916', and 918' can similarly be identified at location (X1, Y1), (X2, Y1), (X1, Y2), and (X2, Y2), respectively, in sample 902.

Figure 10:
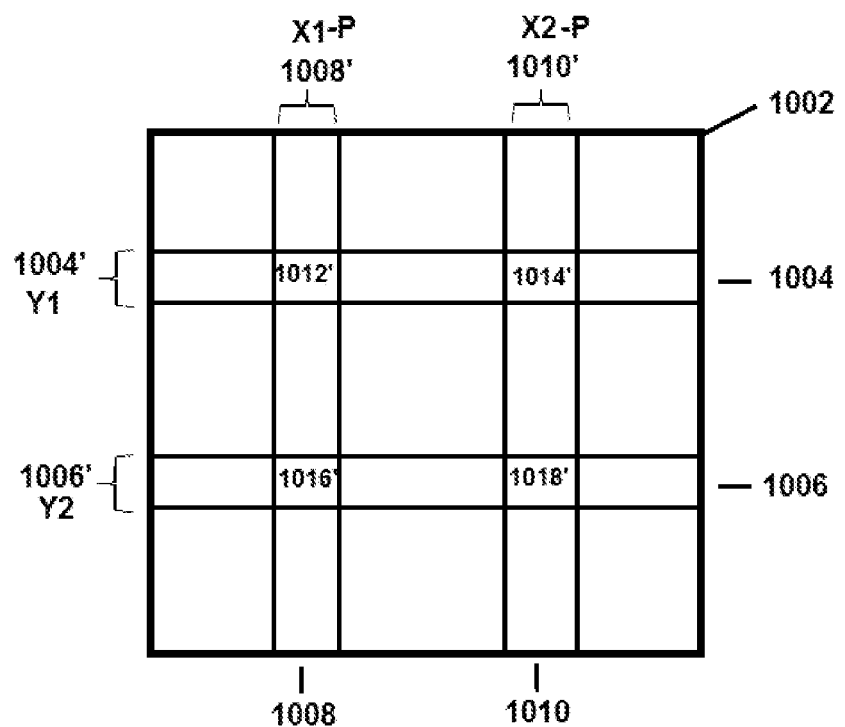
FIG. 10 illustrates a microfluidic device based reagent delivery and address tagging scheme, according to one embodiment of the present disclosure.

In another embodiment as shown in FIG. 10, sample 1002 is affixed to a first microfluidic device having multiple first addressing channels 1004 and 1006, wherein each first addressing channel identifies a first area (1004' and 1006', respectively) in the sample. A first address tag is then delivered through each of the first addressing channels to each first area in the sample. For example, in FIG. 10, address tag Y1 is delivered through first addressing channel 1004 to first area 1004', and address tag Y2 is delivered through first addressing channel 1006 to first area 1006'. Sample 1002 with the delivered address tags Y1 and Y2 is then affixed to a second microfluidic device comprising multiple second addressing channels 1008 and 1010, wherein each second addressing channel identifies a second area (1008' and 1010', respectively) in the sample. A probe with a second address tag already installed is then delivered through each of the second addressing channels to each second area in the sample. For example, in FIG. 10, a probe with address tag X1 ("X1-P") is delivered through second addressing channel 1008 to second area 1008', and the same probe with address tag X2 ("X2-P") is delivered through second addressing channel 1010 to second area 1010'. In this embodiment, the previously delivered address tags Y1 and Y2 must remain in situ until the probes X1-P and X2-P are made available for reaction. This can be achieved by allowing Y1 and Y2 to dry in situ and avoiding any wash steps prior to attachment to the probes X1-P and X2-P. After drying, delivery of probes X1-P and X2-P rehydrates the sample and permits attachment of Y1 and Y2. Alternatively, in order to achieve greater efficiency, tags Y1 and Y2 can contain a tethering moiety, allowing them to be tethered to the sample to prevent diffusion. Tethering can be covalent or non-covalent. For example, Y1 and Y2 can be conjugated at their 3' ends to a photo-activatable moiety, and upon delivery, UV irradiation can be used to link Y1 and Y2 to reactive groups in the sample. Non-covalent attachment can be achieved by conjugating Y1 and Y2 to an antibody that binds to an abundant structural component of the sample, such as actin, or to proteins in general. Following tethering of Y1 and Y2, probes X1-P and X2-P are delivered and allowed to hybridize to their targets, without the duration of this step being limited by the loss of spatial resolution or signal due to diffusion of Y1 and Y2. By preventing diffusion, tethering also permits stringency washing to remove molecules of X1-P and X2-P that are non-specifically bound, thereby increasing specificity. Subsequently, Y1 and Y2 can be untethered for reaction with X1-P and X2-P. This can be accomplished using a variety of techniques. For example, a photo-cleavable linker that connects Y1 and Y2 to their tethering moieties can be cleaved by photolysis. If, however, a photo-reactive group is used for tethering, a type of linker that is not prone to photolysis during the tethering reaction should be used. A wide variety of cleavable linkers are available, including chemically or enzymatically cleavable linkers. An example of the latter is a nucleic acid sequence that is specifically cleaved by a restriction enzyme. If necessary, the sequence can be made double-stranded by hybridization of a complementary sequence. The complementary sequence can be added separately or can be a part of the Y1 and Y2 molecules, in which case they would be designed to fold back and hybridize in a hairpin configuration. Previously delivered address tags Y1 and Y2 are then coupled to probes bound to biological targets in first areas 1004' and 1006', respectively. The untethering of Y1 and Y2 can be carried out contemporaneously with coupling. For example, the second addressing channels can be kept in place and used to add a mixture of a suitable restriction enzyme and T4 DNA ligase. The restriction enzyme untethers Y1 and Y2 by cleaving the linker, and ligase couples Y1 and Y2 to X1-P and X2-P respectively. Conditions that are compatible with both a restriction endonuclease and a DNA ligase are well known in the art. In this illustrative example, four intersections are formed between the first and second areas: 1012', 1014', 1016', and 1018', comprising probes with the coupled first address tags X1-P-Y1, X2-P-Y1, X1-P-Y2, and X2-P-Y2, respectively. Therefore, intersections 1012', 1014', 1016', and 1018' can similarly be identified at location (X1, Y1), (X2, Y1), (X1, Y2), and (X2, Y2), respectively, in sample 1002.

The reagent delivery and address tagging scheme based on microfluidic device is also compatible with the two-probe approach (e.g., those shown in FIG. 4 and FIG. 6) or dual targeting approach described supra. For example, in FIG. 11A, probes P and P' both specifically bind to a biological target. In FIG. 11B, sample 1102 is affixed to a first microfluidic device having multiple first addressing channels 1104 and 1106, wherein each first addressing channel identifies a first area (1104' and 1106', respectively) in the sample. A probe with a first address tag already installed is then delivered through each of the first addressing channels to each first area in the sample. For example, in FIG. 11B, a probe with address tag Y1 ("P'-Y1") is delivered through first addressing channel 1104 to first area 1104', and the same probe with address tag Y2 ("P'-Y2") is delivered through first addressing channel 1106 to first area 1106'. Sample 1102 with the delivered P'-Y1 and P'-Y2 probes is then affixed to a second microfluidic device comprising multiple second addressing channels 1108 and 1110, wherein each second addressing channel identifies a second area (1108' and 1110', respectively) in the sample. A probe with a second address tag already installed is then delivered through each of the second addressing channels to each second area in the sample. For example, in FIG. 11B, a probe with address tag X1 ("X1-P") is delivered through second addressing channel 1108 to first area 1108', and the same probe with address tag X2 ("X2-P") is delivered through second addressing channel 1110 to second area 1110'. In this illustrative example, four intersections are formed between the first and second areas: 1112', 1114', 1116', and 1118', comprising probe pairs (X1-P, P'-Y1), (X2-P, P'-Y1), (X1-P, P'-Y2), and (X2-P, P'-Y2), respectively. Therefore, intersections 1112', 1114', 1116', and 1118' can similarly be identified at location (X1, Y1), (X2, Y1), (X1, Y2), and (X2, Y2), respectively, in sample 1102.

Figure 9:
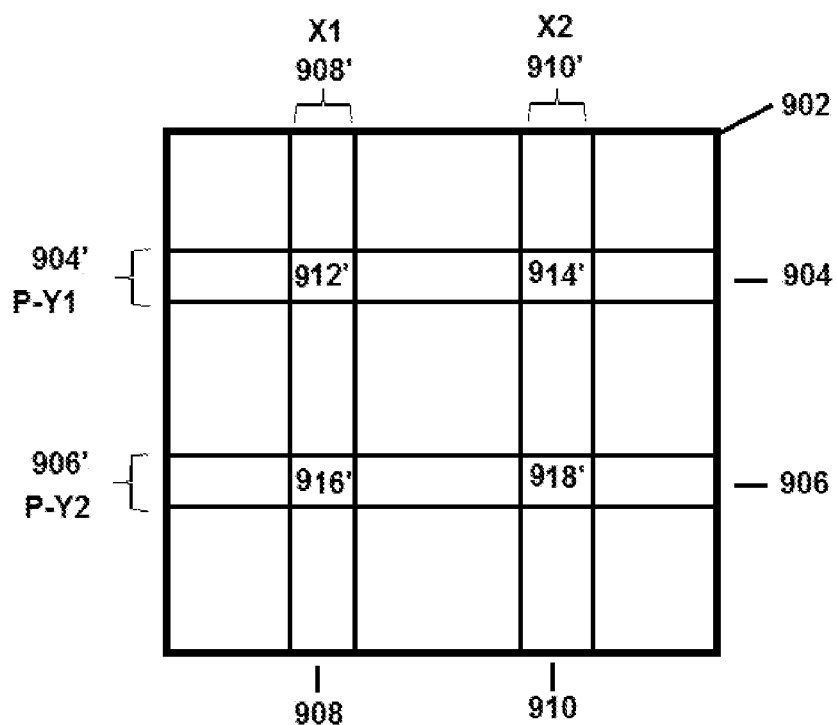
FIG. 9 illustrates a microfluidic device based reagent delivery and address tagging scheme, according to one embodiment of the present disclosure.
Figure 11:
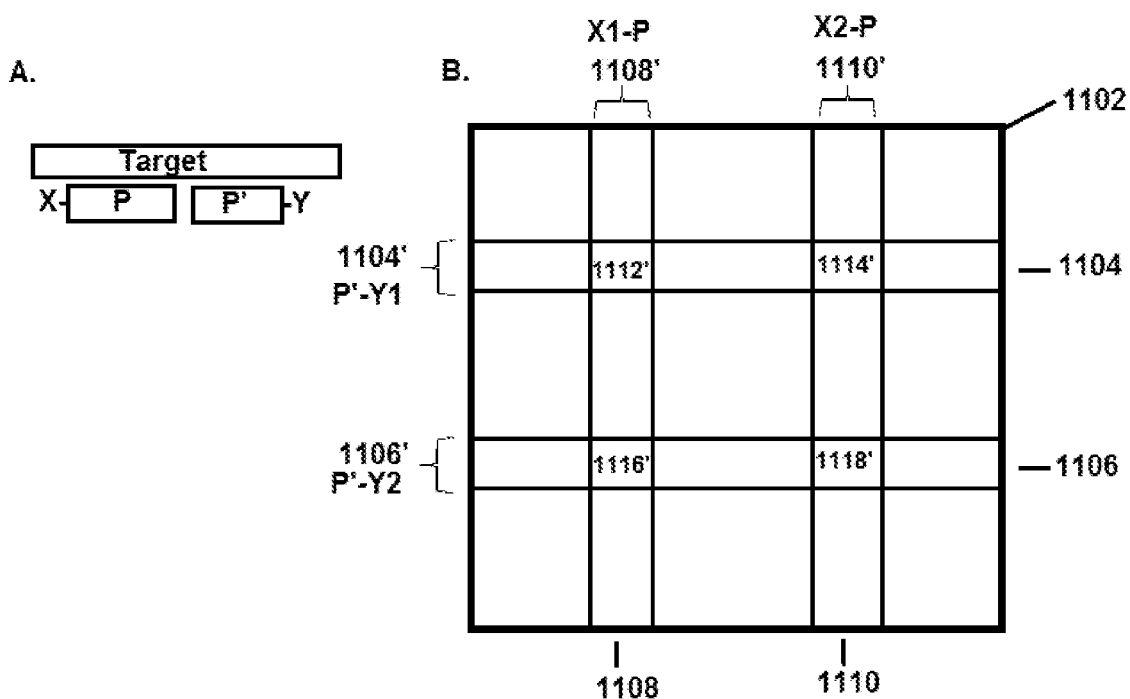
FIG. 11 illustrates a microfluidic device based reagent delivery and address tagging scheme, according to one embodiment of the present disclosure.

In any of the embodiments disclosed herein, channel-level probes may be used. In one aspect, a channel-level probe spatially encodes an entire X or Y channel, and may be used to assay target abundance, expression, and/or activity in the entire channel. In any of the embodiments disclosed herein, probes may be designed so that either the X or the Y address tag is not specific to a particular X or Y channel, respectively. Address tags that are not channel-specific are designated as "X0" or "Y0" tags. For example, a probe with the sequence X0-P-Yn is localized to a stripe corresponding to the Yn channel, because the X0 address tag can be found in all X channels. In certain embodiments, this can be accomplished by including a probe X0-P together with probe P, which can be pre-hybridized to the sample, for example, as shown in FIG. 8. The X0-P probe can hybridize to targets in the entire sample, together with probe P. When the sample is affixed to a second microfluidic device, and channel-specific address tag Xn is delivered and coupled to probe P, the Xn channel would contain a mixture of probe X0-P and probe Xn-P. In this case, the sample has been affixed to a first microfluidic device, and channel-specific address tags Y1, Y2, . . . , and Yn have been delivered and coupled to probe P. Thus, target abundance, expression, and/or activity at a particular location (Xn, Yn) in the sample can be indicated by the level of the Xn-P-Yn probe bound to the sample, while target abundance, expression, and/or activity in the entire Yn channel can be indicated by signals from the X0-P-Yn probe. In cases where probes are pre-installed with address tags before being delivered to the sample (for example, as shown in FIGS. 9-11), each channel can receive a mixture of the channel-specific probe together with the X0-P probe (or P-Y0 probe). In one embodiment, a channel-level probe or address tag may be used in conjunction with site-specific probes or address tags X1, X2, . . . , and Xn, and/or Y1, Y2, . . . , and Yn. X0 and/or X0-P can be delivered to the entire sample, or to the sample through any Y channel together with the site-specific Y probe or address tag. Similarly, channel-level probe P-Y0 or address tag Y0 can be delivered to the entire sample, or to the sample through any X channel together with the site-specific X probe or address tag. In certain embodiments, readout based on probe X0-P-Yn captures signals from all X-dimension signals of the Yn channel, and readout based on probe Xn-P-Y0 captures signals from all Y-dimension signals of the Xn channel. In certain aspects, the input ratio of a probe containing an X0 address tag can be adjusted relative to probes containing Xn address tags (where n≥1) in order to produce a suitable output ratio of X0 to Xn tagged probes, taking into account, for example, the channel dimensions or number of intersecting channels. Similarly, in certain embodiments, the input ratio of X0 address tags to Xn address tags, the input ratio of Y0 probes to Yn probes, and the input ratio of Y0 address tags to Yn address tags, can also be adjusted. In certain embodiments, channel-level probes or address tags provide controls for and allow estimation of ligation efficiency of the address tags to the probe, for example, relative ligation yield of X1 to Xn versus X0, and relative ligation yield of Y1 to Yn versus Y0. In other embodiments, channel-level probes or address tags provide controls for and allow estimation of adaptor-specific yield variation, for example, relative yields of X1 through Xn paired with Y0, and Y1 through Yn paired with X0. In one aspect, channel-level probes or address tags provide channel-level measurements of target abundance, expression, and/or activity. In another aspect, channel-level probes or address tags enable comparison of target abundance, expression, and/or activity at each (X, Y) location in a channel versus the channel average.

Figure 12:
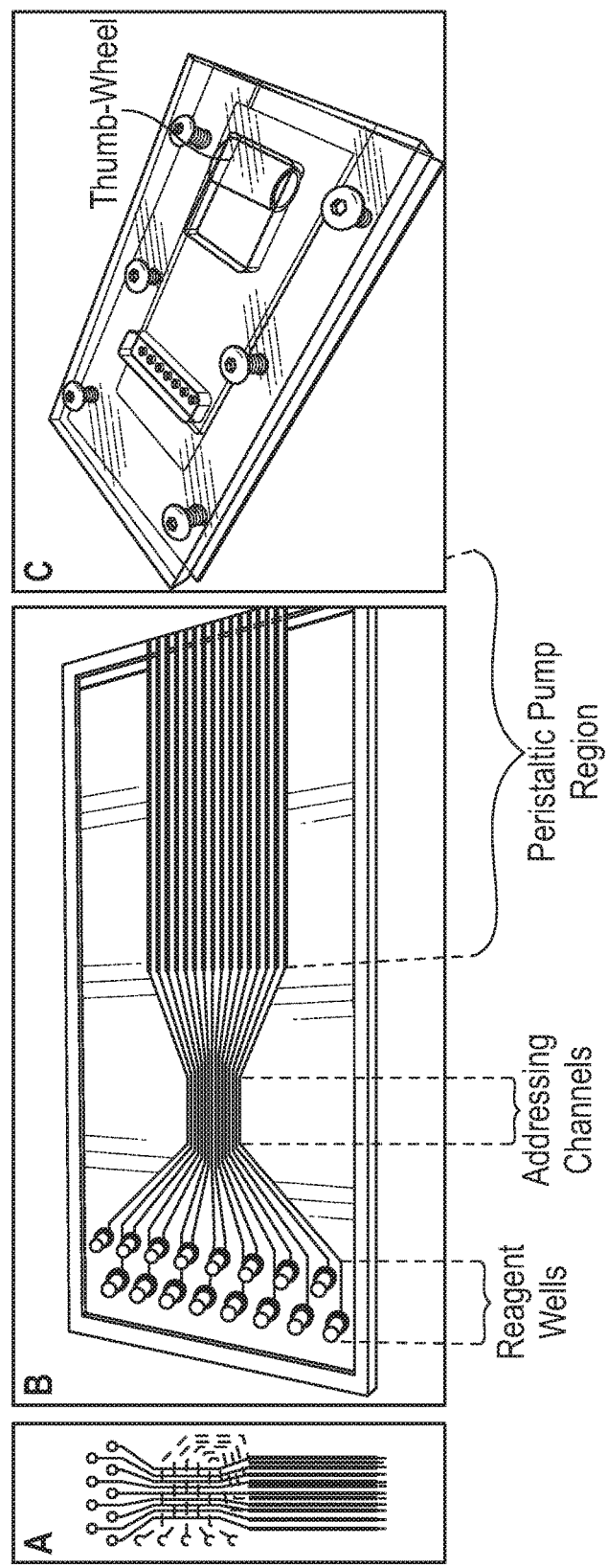
FIG. 12 illustrates a microfluidic addressing device, according to one embodiment of the present disclosure.

Although a number of different reagent delivery technologies, including random-access methods (e.g., inkjet and pin-spotting), may be used for the multiplex assays, a system using microfluidic flow-channel devices is used in preferred embodiments. In certain aspects, microfluidic devices used in any of the embodiments disclosed herein can be made by soft-lithographic techniques. Soft-lithographic techniques typically allow rapid development of microfluidic devices at a fraction of the cost and time needed to develop or buy a suitable instrument for printing or spotting reagents. In certain other embodiments, the size of the sampling area can be strictly defined using microfluidic devices of the present disclosure. In contrast, use of printed droplets of reagents would require special care and more complex technology to reduce or avoid spreading of reagents non-uniformly on the surface of an FFPE sample, which may result in sampling areas of varying sizes and shapes. In other embodiments, the reagent delivery system using microfluidic devices does not require precise alignment of the sample. This feature allows sequential ligation of the two encoding positional adaptors (i.e., the two address tags). Compared to simultaneous ligation of the two address tags, sequential ligation may reduce the formation of undesired products. In certain aspects, for reagent delivery technologies using inkjet or pin-spotting, the location of each droplet or spot of the first address tag must coincide with a droplet or spot of the second address tag in order to form the full construct during sequential ligation. This would require that the precise registration of the sample be preserved throughout both printing steps. In contrast, in certain embodiments, the microfluidic device based methods and systems use a pair of microfluidic devices each having a set of parallel channels, where the first and second devices have their channels oriented perpendicular to one another as shown in FIG. 12A. A microfluidic addressing device is shown with overlayed layout for a pair of addressing devices in FIG. 12A, a poly(dimethylsiloxane) (PDMS) elastomer device with 16×16 channels and 100 µm channel width in FIG. 12B, and an assembled device with the clamp and peristaltic pump mechanism in FIG. 12C.

In certain embodiments, the device can be cast out of a PDMS elastomer. In alternative embodiments, the device can be made of compression molded silicone rubber. In other aspects, the device can be made by a multilayer plastic and elastomer bonding process. In yet another aspect, thermoplastics may also be used for the manufacture of the present device.

In certain aspects, the geometry of the devices defines a rectangular array of junctions (or intersections), each having an area that is defined by the width of the two channels. When each first channel and each second channel receive and deliver a different address tag, the result is a unique pair of identifying address tags for each junction or intersection in the array. In certain embodiments, fluid flow in microfluidic devices can be driven by external syringe pumps or vacuum. In other embodiments, microfluidic devices may include connections between the microscopic channels and the macroscopic components of the systems. In preferred embodiments, the reagent delivery system used in the present disclosure can be a self-contained system for loading reagents into the channels. In some aspects, the device may include reagent reservoirs and microscopic addressing channels, each of which can be connected to a larger peristaltic pump channel either upstream or downstream of the reservoir, and either upstream or downstream of the addressing channels. In other aspects, the device can be applied to the surface of an FFPE sample and clamped in place. In other embodiments, a thumb-wheel or other rolling device can be applied across some or all the pump channels and the rolling action can draw or push the liquid from each reservoir through the addressing channels. In other embodiments, centrifugal force can be used to move liquid through the channels. In other embodiments, liquid can be moved by electroosmotic force, surface acoustic waves, or other electromechanical means. In further embodiments, the liquid can contain reagents, for example, address tags, and can contact the tissue sample via the addressing channels.

When address tags are delivered to the sample through the addressing channels, each address tag can be ligated onto the hybridized probes. In certain aspects, after the first ligation, the device can be removed and the sample optionally washed, for example, to remove address tags not ligated or otherwise coupled to the probes. In certain embodiments, a second device positioned on the sample with its addressing channels substantially perpendicular to the addressing channels of the first device may be used to install the second set of address tags. In these embodiments, the first addressing channels are disposed on a separate device from the second addressing channels. In alternative embodiments, the first addressing channels are disposed on the same device as the second addressing channels. In particular embodiments, the sample after receiving a first set of reagents, for example, a first set of address tags to be coupled to the probe, may be rotated about 90 degrees and affixed on the same device to receive a second set of reagents. In this case, the first and second addressing channels are not only disposed on the same device but also are essentially the same set of addressing channels. In certain aspects, only the areas of the sample at the intersection of the first and second addressing channels receive both address tags. In some aspects, the devices can be cleaned and reused. Other configurations of microfluidic devices providing a first and second set of addressing channels may be used, and the process of placing or affixing samples to the devices, the process of transferring samples between or within devices, the process of sample processing (e.g., washing), and the process of delivering reagents to samples may be automated or streamlined.

In certain embodiments, the angle between the first and second addressing channels may be about 90 degrees, about 80 degrees, about 70 degrees, about 60 degrees, about 50 degrees, about 40 degrees, about 30 degrees, about 20 degrees, or about 10 degrees. In certain other embodiments, the angle between the first and second addressing channels may be between about 90 degrees and about 80 degrees, between about 80 degrees and about 70 degrees, between about 70 degrees and about 60 degrees, between about 60 degrees and about 50 degrees, between about 50 degrees and about 40 degrees, between about 40 degrees and about 30 degrees, between about 30 degrees and about 20 degrees, or between about 20 degrees and about 10 degrees. In other embodiments, the multiple first addressing channels may substantially parallel each other and the multiple second addressing channels may substantially parallel each other.

In certain embodiments, the number of the first and/or second addressing channels can be any integer greater than 1. In any of the preceding embodiments, the width of the first and/or second addressing channels can be about 1 μm, about 2 μm, about 5 μm, about 10 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, about 100 μm, about 105 μm, about 110 μm, about 115 μm, about 120 μm, about 125 μm, about 130 μm, about 135 μm, about 140 μm, about 145 μm, about 150 μm, about 155 μm, about 160 μm, about 165 μm, about 170 μm, about 175 μm, about 180 μm, about 185 μm, about 190 μm, about 195 μm, or about 200 μm. In some aspects, the width of the first and/or second addressing channels can be between about 200 μm and about 250 μm, between about 250 μm and about 300 μm, between about 300 μm and about 350 μm, between about 350 μm and about 400 μm, between about 400 μm and about 450 μm, between about 450 μm and about 500 μm, between about 500 μm and about 550 μm, between about 550 μm and about 600 μm, between about 600 μm and about 650 μm, between about 650 μm and about 700 μm, between about 700 μm and about 750 μm, between about 750 μm and about 800 μm, between about 800 μm and about 850 μm, between about 850 μm and about 900 μm, between about 900 μm and about 950 μm, or between about 950 μm and about 1000 μm. In other aspects, the width of the first and/or second addressing channels can be greater than about 1000 μm.

In any of the preceding embodiments, the depth of the first and/or second addressing channels can be about 1 μm, about 2 μm, about 5 μm, about 10 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, about 100 μm, about 105 μm, about 110 μm, about 115 μm, about 120 μm, about 125 μm, about 130 μm, about 135 μm, about 140 μm, about 145 μm, about 150 μm, about 155 μm, about 160 μm, about 165 μm, about 170 μm, about 175 μm, about 180 μm, about 185 μm, about 190 μm, about 195 μm, or about 200 μm. In some aspects, the depth of the first and/or second addressing channels can be between about 200 μm and about 250 μm, between about 250 μm and about 300 μm, between about 300 μm and about 350 μm, between about 350 μm and about 400 μm, between about 400 μm and about 450 μm, between about 450 μm and about 500 μm, between about 500 μm and about 550 μm, between about 550 μm and about 600 μm, between about 600 μm and about 650 μm, between about 650 μm and about 700 μm, between about 700 μm and about 750 μm, between about 750 μm and about 800 μm, between about 800 μm and about 850 μm, between about 850 μm and about 900 μm, between about 900 μm and about 950 μm, or between about 950 μm and about 1000 μm. In other aspects, the depth of the first and/or second addressing channels can be greater than about 1000 μm.

In any of the preceding embodiments, the distance between each first addressing channel and/or between each second addressing channel can be about 1 μm, about 2 μm, about 5 μm, about 10 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 75 μm, about 80 μm, about 85 μm, about 90 μm, about 95 μm, about 100 μm, about 105 μm, about 110 μm, about 115 μm, about 120 μm, about 125 μm, about 130 μm, about 135 μm, about 140 μm, about 145 μm, about 150 μm, about 155 μm, about 160 μm, about 165 μm, about 170 μm, about 175 μm, about 180 μm, about 185 μm, about 190 μm, about 195 μm, or about 200 μm. In certain aspects, the distance between each first addressing channel and/or between each second addressing channel can be between about 1 μm and about 2 μm, between about 2 μm and about 5 μm, between about 5 μm and about 10 μm, between about 10 μm and about 15 μm, between about 15 μm and about 20 μm, between about 20 μm and about 25 μm, between about 25 μm and about 30 μm, between about 30 μm and about 35 μm, between about 35 μm and about 40 μm, between about 40 μm and about 45 μm, between about 45 μm and about 50 μm, between about 50 μm and about 55 μm, between about 55 μm and about 60 μm, between about 60 μm and about 65 μm, between about 65 μm and about 70 μm, between about 70 μm and about 75 μm, between about 75 μm and about 80 μm, between about 80 μm and about 85 μm, between about 85 μm and about 90 μm, between about 90 μm and about 95 μm, between about 95 μm and about 100 μm, between about 100 μm and about 105 μm, between about 105 μm and about 110 μm, between about 110 μm and about 115 μm, between about 115 μm and about 120 μm, between about 120 μm and about 125 μm, between about 125 μm and about 130 μm, between about 130 μm and about 135 μm, between about 135 μm and about 140 μm, between about 140 μm and about 145 μm, between about 145 μm and about 150 μm, between about 150 μm and about 155 μm, between about 155 μm and about 160 μm, between about 160 μm and about 165 μm, between about 165 μm and about 170 μm, between about 170 μm and about 175 μm, between about 175 μm and about 180 μm, between about 180 μm and about 185 μm, between about 185 μm and about 190 μm, or between about 190 μm and about 200 μm. In other aspects, the distance between each first addressing channel and/or between each second addressing channel can be about 0.2 mm, about 0.3 mm, about 0.4 mm, about 0.5 mm, about 0.6 mm, about 0.7 mm, about 0.8 mm, about 0.9 mm, about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, or about 2.0 mm. In yet other aspects, the distance between each first addressing channel and/or between each second addressing channel can be between about 0.2 mm and about 0.3 mm, between about 0.3 mm and about 0.4 mm, between about 0.4 mm and about 0.5 mm, between about 0.5 mm and about 0.6 mm, between about 0.6 mm and about 0.7 mm, between about 0.7 mm and about 0.8 mm, between about 0.8 mm and about 0.9 mm, between about 0.9 mm and about 1.0 mm, between about 1.0 mm and about 1.1 mm, between about 1.1 mm and about 1.2 mm, between about 1.2 mm and about 1.3 mm, between about 1.3 mm and about 1.4 mm, between about 1.4 mm and about 1.5 mm, between about 1.5 mm and about 1.6 mm, between about 1.6 mm and about 1.7 mm, between about 1.7 mm and about 1.8 mm, between about 1.8 mm and about 1.9 mm, or between about 1.9 mm and about 2.0 mm. In certain other aspects, the distance between each first addressing channel and/or between each second addressing channel can be about 2.2 mm, about 2.4 mm, about 2.6 mm, about 2.8 mm, about 3.0 mm, about 3.2 mm, about 3.4 mm, about 3.6 mm, about 3.8 mm, about 4.0 mm, or greater than about 4.0 mm.

Creation of devices according to the present disclosure that have various numbers of sites, various sizes of site areas, and/or different spacing between sites will allow assays of tissues at varying resolutions in order to observe long-range and short-range variation in expression levels. In some embodiments, the microfluidic devices disclosed herein can be used to address areas of the size of or even smaller than a single cell.

Figure 13:
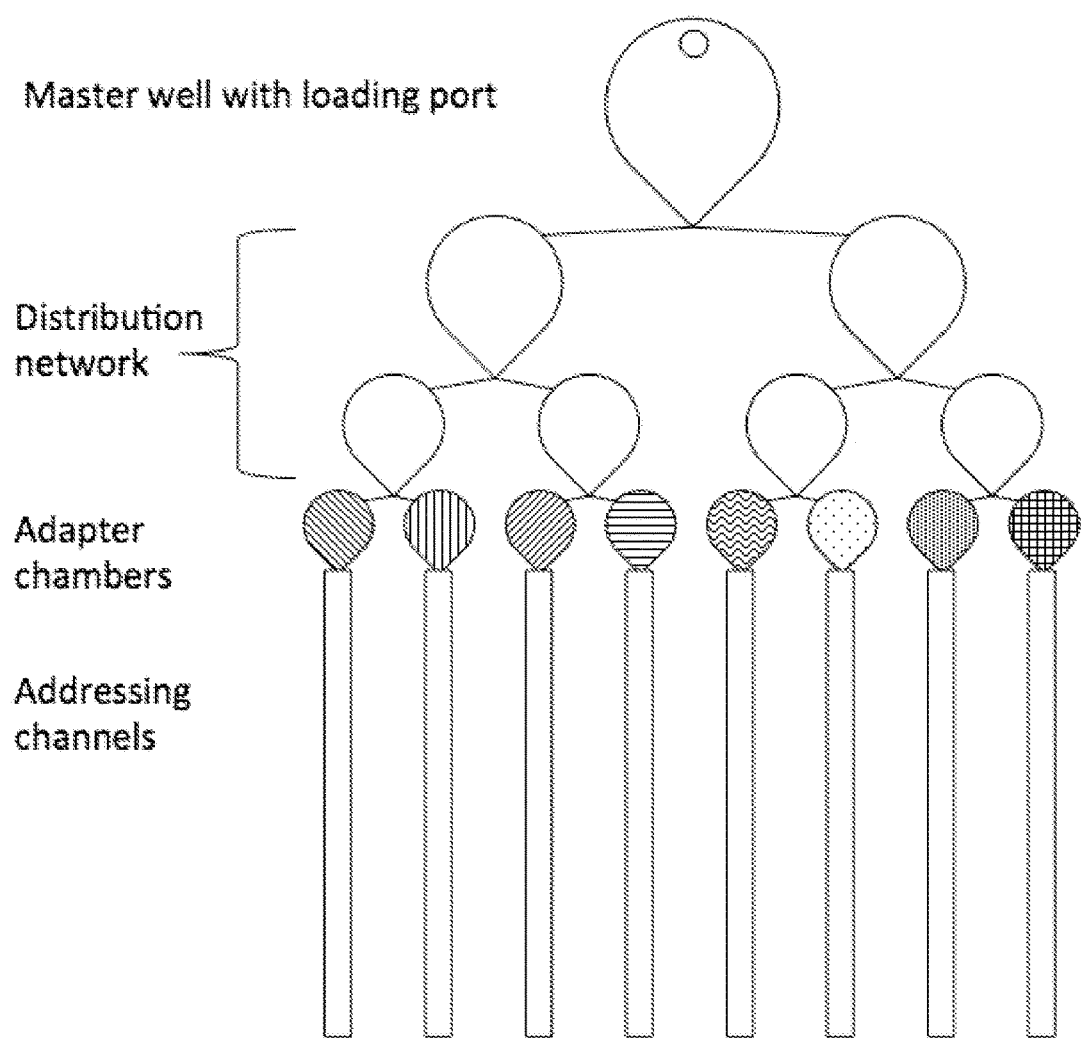
FIG. 13 illustrates a microfluidic channel network, according to one embodiment of the present disclosure.

In certain embodiments, a user of the present device prepares and loads into each reservoir for each addressing channel a different reagent, for example, an address tag. For instance, for a 32×32 microfluidic device, a total of 64 different address tag mixes for each experiment may need to be prepared and correctly loaded. A relatively costly component (DNA ligase) may also be wasted during the individual preparation and loading processes. Provided herein are methods and designs that decease the risk of pipetting error and help save time and cost. In certain embodiments, the microfluidic device may be pre-loaded with the address tags prior to use, and users may then only need to add a single master mix comprising enzymes and other reagents. In certain aspects, the master mix can be pipetted into all wells or reservoirs without risk of mix-ups, and in other aspects, only a single master well or reservoir may need to be loaded with master mix, which would be distributed within the microfluidic device to each addressing channel. Delivery of the master mix or any other reagent of the present disclosure may be implemented by using a connected microfluidic channel network device. For example, a set of microfluidic channels on a microfluidic device can be connected together so as to achieve a desired function (mix, pump, redirect and/or allow chemical reactions). The network of microfluidic channels can be connected to the outside by inputs and outputs, through which liquid or gas reagents are injected and/or removed from the connected microfluidic channel network. Exemplary microfluidic channel network devices are described in U.S. Pat. No. 7,223,371, the disclosure of which is incorporated herein by reference for all purposes. One such arrangement is shown in FIG. 13. In this embodiment, a single master well is loaded with a precise volume of master mix through a loading port. The mix travels through a network of chambers and channels where it is divided into smaller volumes at each level of the network until it reaches the adaptor chambers, which have been preloaded with addressing adaptors. These adaptors are then resuspended in the master mix as it travels into the addressing channels. A somewhat similar approach for distributing a master mix within a microfluidic system has been employed by the 384-well microfluidic card Taqman gene expression assays developed by Applied Biosciences (Custom TaqMan® Array Cards, Life Technologies, Inc., Carlsbad, Calif.).

Under suitable conditions, DNA oligonucleotides can be stored dry for long periods of time. In certain aspects, provided herein is a liquid carrier formulation of the address tags (oligonucleotides) that can be added to the device and subsequently dried down in situ. In preferred embodiments, the carrier is chemically compatible with the device and reagents and is capable of being delivered and dried without adversely affecting the device or oligos. Upon drying, the oligos may be robustly fixed in location and are stable during long-term storage under suitable conditions. In preferred embodiments, the oligos can be easily resuspended when a master mix is added, for example, months later. In another aspect, the address tag mixes can be loaded into the devices and then stored frozen. In certain aspects, a master mix is added to resuspend the dried oligonucleotides rapidly and efficiently. In one aspect, passive mixing may be sufficient. In another aspect, an active resuspension procedure may be needed. For example, the active resuspension procedure may be accomplished by pipetting up and down upon addition. In another aspect, the active resuspension procedure may involve building additional mixing functionality into the device, preferably without introducing unnecessary complexity.

In one embodiment, the assay systems and devices disclosed herein can discriminate different tissue types on the basis of tissue-specific differences in gene expression. In one aspect, the assay systems and devices disclosed herein can be used to assay and discriminate mRNA and hnRNA, and therefore can be used for parallel analysis of RNA processing in situ. In one aspect, probes are designed to target introns and/or exons. In one aspect, intronic probes give signal from hnRNA, but not from mRNA. The gDNA background signal can be measured using selective pretreatments, with DNase and/or RNase. In one aspect, splice-site specific probes that are selective for spliced RNAs may be designed and used. In certain embodiments, a combination of intronic probes, exonic probes, and/or splice-site specific probes may be used to identify the relative level of processing intermediates and their differences between different cells in a tissue section. In general, RNA may be bound to proteins of various types, and hnRNA, in particular, is complexed with proteins to form hnRNP (heterogeneous nuclear ribonucleoprotein). In one embodiment, the devices and assay systems disclosed herein can be used to perform highly parallel in situ footprinting experiments. In certain aspects, instead of targeting 1,000 different RNAs, probes can be tiled densely through a smaller number of RNAs in order to generate a signal profile along the molecule. Relative changes in this profile between cell types would then indicate differences in availability of the RNA, at the specific locations assayed.

In certain embodiments, two probes that bind to the same target molecule (for example, two polynucleotide probes that hybridize to adjacent sites on a nucleic acid target) may be assayed by extension followed by ligation (the extension-ligation assay). The extension-ligation assay allows certain target sequence to be determined de novo. For example, if the primer and the downstream oligo are separated by 20 bases and reverse transcriptase is used to fill this 20-base gap, 20 bases of sequence of the RNA target can be obtained. In certain embodiments, by using the extension-ligation assay in the present methods or assay systems, regions of sequence that are of particular interest may be characterized. For example, these regions may comprise mutations or variations, for example, with implications in cancer, MHC variations, and RNA editing.

Figure 14:
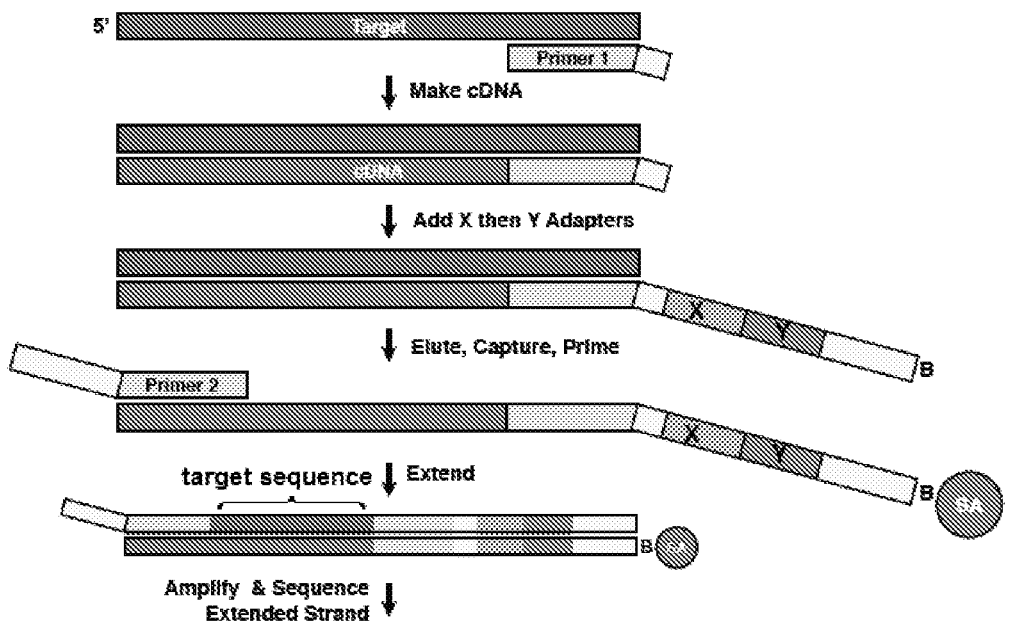
FIG. 14 illustrates an extension assay, according to one embodiment of the present disclosure.

In any of the embodiments disclosed herein, an extension assay may also be used and may allow certain target sequences to be determined de novo. In one embodiment, an extension assay of the present disclosure may be performed as shown in FIG. 14. First, Primer 1 is used to make cDNA from a target sequence. In certain embodiments, the primer can be a random primer (e.g., random hexamer) or a sequence-specific primer. A random primer can be used to make cDNA from the entire transcriptome, while a sequence-specific primer may be used to make cDNA from a specific target sequence. In certain aspects, the primer may comprise a universal priming site for amplification of the assay products, an adaptor to enable sequence identification by sequencing techniques, and/or an adaptor for attaching address tags. Here in FIG. 14, Primer 1 is conjugated to an adaptor for attaching address tags. The X and Y address tags are then coupled to Primer 1 via the adaptor. Note that in this case the X and Y address tags are coupled to the same side relative to the target sequence, and this configuration may be used in any of embodiments disclosed herein. The Y address tag in this case is further linked to a universal priming site or an adaptor for sequencing coupled to biotin (shown as "B" in the figure). The cDNA with conjugated X and Y address tags are then eluted and captured on a streptavidin bead (shown as "SA" in the figure), and Primer 2 is then installed. Installation of Primer 2 can be by more than one means, e.g. hybridizing Primer 2 and extending it using a polymerase, or by ligating an adaptor that contains the Primer 2 priming site. In some embodiments, capture of the polynucleotide sequence can be based on other hapten-binder combinations other than biotin-streptavidin, or be sequence-based. In certain embodiments, Primer 2 can be a random primer (e.g., random hexamer) or a sequence-specific primer. In certain aspects, the primer may comprise a universal priming site for amplification of the assay products, an adaptor to enable sequence identification by sequencing techniques, and/or an adaptor for attaching address tags. Here in FIG. 14, Primer 2 may be conjugated to a universal priming site or an adaptor for sequencing. Together with the priming site or adaptor coupled to biotin, the sequence can be extended from Primer 2, amplified, and sequenced. The target sequence in the product following extension is indicated in FIG. 14.

The methods and assay systems disclosed herein may comprise an amplification step, and in particular, a nucleic acid amplification step. In certain aspects, the amplification step is performed by PCR. In some embodiments, linear amplification (e.g., by T7 RNA polymerase) may be used instead of PCR or as a partial replacement for PCR. In one aspect, linear amplification of polynucleotides may cause less distortion of the relative abundances of different sequences. This can be accomplished by including a T7 RNA pol promoter in one of the universal portions of the sequence. In this case, the promoter itself and regions upstream of the promoter are not copied. In yet other embodiments, other amplification methods may be used in the methods and assay systems disclosed herein. For some sequencing methods (e.g., nanopore sequencing), amplification may be optional.

Various methods can be used to form an amplifiable construct, for example, by using ligation of proximal probes followed by sequential ligation of a pair of spatial encoding adaptors (address tags) as shown in FIG. 15A. In one embodiment, two DNA probes are hybridized proximal to one another on an RNA target (or template). The probes are subsequently ligated to one another and the quantity of the ligated pair is taken as a measure of the amount of the target present in the sample. In certain cases, however, the efficiency of T4 DNA ligase is reduced when the ligation reaction occurs on an RNA template as compared to a DNA template. In other cases, the ligation efficiency is dependent on the sequence of the DNA probes that are being joined, the particularly on the identity of the first few bases on either side of the junction. In some embodiments, a method disclosed herein mitigates both problems. FIG. 15B shows the general principle of the method. In this case, instead of using probes that hybridize in direct proximity on an RNA target, the probes are separated by some distance with non-hybridizing overhanging sequences on their proximal ends. These overhanging sequences are designed to be complementary to a short DNA splint. This splint can be universal for all the probe pairs in a multiplexed assay or can be specific for a given probe pair or subset of probe pairs. The distance between the two probes in a pair can be adjusted to optimize ligation efficiency. There is flexibility in this distance, which provides an additional degree of freedom when designing probes versus the use of proximal probes. Once the probes are hybridized to the RNA target, excess probes are washed away. The splint is hybridized to the overhanging regions at the proximal ends of the probes, and the probes are joined by enzymatic ligation. After ligation, the remaining steps of the assay are performed, for example, ligating the spatial encoding adaptors to each end of the ligated probe pair. In certain aspects, since DNA splinted ligation is more efficient than RNA splinted ligation, a method disclosed herein improves the efficiency at which the two probes are joined. In addition, using a universal splint eliminates the sequence-dependent variation in ligation efficiency between the multiple probe sets in a multiplexed in situ assay. In another aspect, probes can be more easily designed, and more suitable probe sets can be designed, due to increased freedom of varying the distance between probes.

The T7 RNA polymerase based amplification is a commonly used protocol for mRNA amplification originally described by van Gelder et al., Proc. Natl. Acad. Sci. USA 87, 1663-1667 (1990). The protocol consists of the synthesis of a cDNA complementary to the mRNA ("first strand synthesis"), effected by reverse transcription, followed by second strand synthesis to yield double-stranded cDNA, and in vitro transcription using the double-stranded cDNA as template effected with T7 RNA polymerase. The last step provides single-stranded antisense RNA (aRNA), which may be labeled in case labeled nucleotides are provided. The nucleotides may be labeled by radioactive labeling or non-radioactive labeling methods. Eberwine et al. (Proc. Natl. Acad. Sci. USA 89, 3010-3014 (1992)) extended van Gelder's method by adding a second round of amplification using the RNA obtained in the first round as template. Wang et al. (Nature Biotechnol. 18, 457-459 (2000)) provided a variant of the original T7 method, characterized by a modified second strand synthesis method. The second strand synthesis method of Wang et al. is known in the art as the SMART™ technology (Clontech) for cDNA synthesis. Baugh et al. (Nucleic Acids Res. 29, E29 (2001)) describe an optimized variant of the method according to van Gelder et al. and analyze the performance on Affymetrix DNA chips (GeneChip®). Affymetrix GeneChips are designed to probe the anti-sense strand. Any other DNA chip or microarray probing the anti-sense strand may be envisaged when performing a T7 RNA amplification, wherein labeling occurs during the in vitro transcription step.

In other embodiments, amplification techniques such as rolling circle amplification (RCA) and circle to circle amplification (C2CA) may be used for probe, target, tag, and/or signal amplification of the present disclosure. RCA is a linear-isothermal process in the presence of certain DNA polymerases, using an ssDNA mini-circle as a template (Fire and Xu, Proc. Natl. Acad. Sci., 92: 4641-4645 (1995); Daubendiek et al., J. Am. Chem. Soc. 117:77818-7819 (1995)). In certain aspects, a polynucleotide sequence can be replicated about 500 to 1000 times, depending on the amplification time. For example, in a dual targeting assay for a target protein as discussed supra, a linear ligated product is formed (e.g., when two antibodies bind to adjacent domains on a target protein, the antibodies' oligonucleotide tags can be ligated), and can be cut by restriction enzymes and then re-ligated to form a DNA circle by a DNA ligase and a template. In certain embodiments, phi29 DNA polymerase can be used to extend the primer, which is also the template, to form a long ssDNA containing a number of sequences complementary to the initial DNA circle. C2CA is based on RCA, and may include three steps: replication, monomerization and ligation (Dahl et al., Proc. Natl. Acad. Sci., 101: 4548-4553 (2004)). The original circular DNA is considered as the positive polarity. After one step of replication (RCA reaction), the product is converted into the opposite polarity. Restriction oligos with the positive polarity ($RO^+$) can form duplex regions with the RCA product, and the duplex regions can be cleaved by restriction enzymes to generate monomers. Then the monomers can be guided into a ligation step and circularized. These circles serve as the templates for the next round of RCA, primed by the $RO^+$. The process can be further repeated to produce around 100-fold higher concentration of target sequences than conventional PCR.

In an optional embodiment, the assay system comprises imaging means to determine features and organization of the biological sample of interest. The images obtained, e.g., may be used to design the delivery pattern of the reagents. Imaging means are optional, as an individual can instead view the biological sample using, e.g., a microscope, analyze the organization of the biological sample, and specify a spatial pattern for delivery assay reagents. If included, the delivery system can comprise a microcircuit arrangement including an imager, such as a CCD or IGFET-based (e.g., CMOS-based) imager and an ultrasonic sprayer for reagent delivery such as described in US Pub. No. 20090197326, which is incorporated herein by reference. Also, it should be noted that although an X-Y grid configuration is illustrated herein, other configurations can be used, such as, e.g., following the topology of a tissue sample; targeting certain groups of cells, cell layers and/or cell types in a tissue, and the like.

In yet another alternative, semiconductor techniques such as masking and spraying may be used in conjunction with the reagent delivery methods and systems disclosed herein, in order to control the delivery of reagents to specific locations on a biological sample surface. Specific areas of a biological sample can be protected from exposure to reagents through use of a mask to protect specific areas from exposure. The reagents may be introduced to the biological sample using conventional techniques such as spraying or fluid flow. The use of masked delivery results in a patterned delivery scheme on the substrate surface.

In order to target specific sites of interest, an informative image of the biological sample to be assayed may be used to assist in the reagent delivery methods and associated encoding scheme. Sample regions of the biological sample can be identified using image processing (e.g., images of cell types differentiated by immunohistochemistry or other staining chemistries) integrated with other features of the assay system. In some aspects, software is used to automatically translate image information into a reagent delivery pattern. In some embodiments, a mechanism to register and align very precisely the biological sample for reagent delivery is an important component of the assay systems. Mechanisms such as the use of fiducial markers on slides and/or other very accurate physical positioning systems can be adapted to this purpose.

The present methods and assay systems may comprise a complete suite of software tailored to the methods or assay systems. Optionally, oligonucleotide design software is used to design the encoding nucleotides (and in embodiments where nucleic acids are assayed, the target-specific oligonucleotides) for the specific assay to be run, and may be integrated as a part of the system. Also optionally, algorithms and software for reagent delivery and data analysis (i.e., sequence analysis) may be integrated to determine assay results. Integrated data analysis is particularly useful, as the type of dataset that is generated may be massive as a consequence of scale. Algorithms and software tools that are specifically designed for analysis of the spatially-associated data generated by the assay systems, including pattern-analysis software and visualization tools, enhance the value of the data generated by the assay systems.

In certain aspects, the assay system comprises processes for making and carrying out the quality control of reagents, e.g., the integrity and sequence fidelity of oligonucleotide pools. In particular, reagents are formulated according to factors such as volatility, stability at key temperatures, and chemical compatibility for compatibility with the reagent delivery instrumentation and may be analyzed by instrumentation integrated within the assay system.

Applications of Assay System

It will be apparent to one skilled in the art upon reading the present disclosure that there are numerous important areas of biological research, diagnostics, and drug development that will benefit from a high throughput multiplexed assay system that can measure simultaneously the amount and spatial location of a biological target in a biological sample. For example, combining the ability to estimate the relative abundance of different RNA transcripts with the ability to reconstruct an image of spatial patterns of abundance across many locations, which may be as small as or even smaller than individual cells, in a tissue enables many different areas of basic research. The following are exemplary uses and are by no means meant to be limiting in scope.

In one example, 3-dimensional patterns of gene expression are determined by analyzing a series of tissue sections, in a manner analogous to image reconstruction in CT scanning. Such a method can be used to measure changes in gene expression in disease pathology, e.g., in cancerous tissue and/or a tissue upon injury, inflammation, or infection. With the assay systems of the invention, more detailed information on gene expression and protein localization in complex tissues is obtained, leading to new insights into the function and regulation both in normal and diseased states, and provides new hypotheses that can be tested. For example, an assay system of the invention may enable some of the insights gained from many individual studies and larger programs like ENCODE (Birney, et al., Nature, 447: 799-816 (2007)) and modENCODE to be integrated at the tissue level. The assay systems also aid computational efforts to model interacting networks of gene expression in the field of systems biology.

The assay systems also provide a novel approach to analysis of somatic variation, e.g., somatic mutations in cancer or variability in response to infectious organisms. For example, tumors are typically highly heterogeneous, containing cancer cells as well as genetically normal cells in an abnormal local environment. Cancer cells undergo mutation and selection, and in this process it is not unusual for local clones to develop. Identifying relatively rare somatic mutations in the context of tumors may enable the study of the role of key mutations in the selection of clonal variants. Transcriptional patterns associated with angiogenesis, inflammation, or other cancer-related processes in both cancer and genetically normal cells can be analyzed for insights into cancer biology and assist in the development of new therapeutic agents for the treatment of cancers. In another example, individuals have varying susceptibility to infectious organisms, and the assay systems of the invention can be used to study the interaction between microbes and tissues or the various cell types within the tissue.

Importantly, in addition to providing spatially-associated information, the invention allows a great increase in the sensitivity of detecting rare mutations, as signal to noise can be dramatically increased since only a small location is assayed in any given reaction. In a typical assay for rare mutations in a mixed sample, the sample is treated in bulk, i.e., nucleic acids are extracted from many cells into a single pool. Thus, if a mutation is present in one cell in 10,000, it must be detected against a background of normal DNA from ~10,000 cells. In contrast, with the assay systems of the invention many cells can be analyzed, but individual cells or small groups of cells would be identified by the spatial coding system. Therefore, in the assay systems of the present invention, background is reduced by orders of magnitude, greatly increasing sensitivity. Furthermore, the spatial organization of mutant cells can be observed, which may be particularly important in detecting key mutations in tissue sections in cancer. Already molecular histological analyses are yielding insights into cancer biology and may have potential for use in diagnostics. The technology of the invention promises to greatly increase the power of such approaches.

The following exemplary embodiments and examples are intended to further describe and illustrate various aspects of the invention, but not to limit, the scope of the invention in any manner, shape, or form, either explicitly or implicitly.

Example 1 Proof of Concept of the Addressing Scheme and Scalability

A model system was developed using a microarray to demonstrate a working multiplexed spatially encoded abundance assays for polynucleotide targets. The basic design validates the concept of the assay, and the addressing scheme, and establishes a working assay prior to addressing issues related to the analysis of a more complicated biological sample.

A microarray was used as a proxy for a tissue section. The target sequences of the microarray were fully specified, so that the composition of the targets was known and was varied systematically, simplifying analysis by next-generation sequencing. One of skill in the art would appreciate that similar assays can be performed on various samples including tissue sections, and for various targets including polynucleotide or protein targets, as well as other biological targets, according to the present disclosure.

A 16-Plex×8-Site Assay Using 8-Section Microarray as Artificial Sample

This 16-plex×8-site assay was performed using a custom DNA microarray (Agilent) as an artificial sample. Eight sites were used because of the commercial availability of 8-section microarrays. Sixteen different target sequences were each assayed over a 128-fold range in DNA amount. Differences in DNA amount were obtained by varying the surface area over which each sequence was synthesized. Differences in DNA amount were detected over the entire range for all sixteen targets, using next-generation sequencing as the readout. This example demonstrated a working multiplex assay using a microarray as an artificial sample, and the spatial encoding accuracy for the model system.

Example 2 A Demonstration of Spatial Encoding Using a Spotted Microarray

Scalability of both the spatial addressing and assay systems is demonstrated by carrying out a 24-plex×24-site assay using a microarray model system.

The amount of biological target, here a DNA target sequence, at each assay location is systematically varied on the microarray substrate. For example, in a microarray with 50 micron spot size (center to center), a 1 $mm^2$ area contains ~400 spots. The region around each site is optionally occupied by a region that is devoid of these spots to allow individual resolvability of the target sequences. Alternatively, the spots may be clustered, with two or more directly adjacent spots surrounded by or adjacent to a region that is devoid of target sequences.

In order to demonstrate that spatial addressing or encoding is accurate, the sites comprise different target compositions to show that the assay readout matches the expected composition of each site. With 24 target sequences, a simple digital pattern is made with each site having a different set of 12 targets present and 12 targets absent, to make a binary code (0=absent, 1=present). The assay readout is then determined to show that the detected regions match the expected signal after spatial decoding. In this particular example, the code (address tag) space is large enough ($2^{24}$) so that even a few errors would not result in different codes being mixed up. Moreover, this design allows identification of errors and allows estimation not only of accuracy of spatial encoding but also of accuracy calling the presence or absence of target sequences.

The ability to detect quantitative differences is evaluated by generating dose-response curves for each of the 24 assays that are carried out at each site in a 24-site assay. This allows estimation of the limit of detection, dynamic range, and power to detect a given fold-change across the range.

In one aspect, a latin square design is used to represent individual targets at different ratios by varying the number of features for each target. In other words, with multiple spots in a site, the number of spots allocated to each of the 24 target sequences can be varied and each of the 24 sites can have a different composition. A 1×3 inch microarray is sufficiently large to permit multiple replicates. This larger set of 24 sequences will require deconvolution, and this is accomplished by using high throughput techniques such as next-generation sequencing technologies (e.g., SOLiD™ technology (Life Technologies, Inc., Carlsbad, Calif.) or Genome Analyzer (I lumina, Inc., San Diego, Calif.)). The use of the 24-plex assay demonstrates both the accuracy of spatial encoding and decoding, and the quantitative response of the assay system.

Example 3 Assays for Preserved Samples and Biological Samples

Genomic DNA is assayed in order to characterize variation in coding and regulatory sequences, such as single nucleotide polymorphisms (SNPs) or mutations, small insertions and deletions (indels), copy number variants such as gene deletions or amplifications, and genetic rearrangements such as translocations, all of which may be functionally significant in cancer and other diseases. Genomic sequence variation as a function of position in the sample may indicate somatic mosaicism in the sample. In cancer samples, mutations may provide prognostic or diagnostic markers that may be useful in determining the best course of treatment. Mutations may identify regions of the sample that contain cancer cells and assist in distinguishing them from normal cells, or cells in the tumor microenvironment that are genetically normal at the sequence level but perturbed in other ways as a result of the influence of cancer cells. In order to distinguish signal generated from DNA targets from those generated by RNA targets, probes can be designed to hybridize to non-coding sequences that are not transcribed. Alternatively, or in order to confirm the specificity of DNA targeting, RNA may be degraded by treatment with RNase. Genomic DNA is also assayed in order to obtain information about its organization and to provide information on the state of activation of certain genes. For example, the ability of probes to bind to DNA may be used as an indicator of whether DNA is condensed or otherwise inaccessible, or whether DNA is in an open conformation for transcription. This type of determination can benefit from comparative analysis of samples in which genes are differentially active. Similarly it may be useful to relate information about RNA and/or protein abundance to information about the activation state of genes. Other types of information are obtained from analysis of epigenetic markers associated with genomic DNA, such as methylation state and the presence of histones and other proteins and modifications.

The handling of small absolute numbers of product molecules generated from very small or compromised samples are enhanced to counter the issue of low recovery efficiency; that is, elution is efficient and losses resulting from adsorption of molecules to surfaces are prevented. An approach to addressing the latter issue is to include a carrier material, such as glycogen or carrier nucleic acids.

In order to adapt the assay to a biological sample and make the tissue section RNA assays as informative as possible, pre-existing information on expression levels in specific tissues to target transcripts across a range of abundances are used in the assay design. Both high abundance transcripts, as well as some medium and low abundance transcripts, are targeted to enable an initial assessment of the quantitative performance characteristics of the assay. In this assay, a control RNA template is immobilized to a solid support in order to create an artificial system. The assay is performed using T4 DNA ligase, which can repair nicks in DNA/RNA hybrids. Assays are carried out on matched slides, or different sections of the same slide, where in one case gDNA is assayed and in the other RNA is assayed. When assaying gDNA the slide can be pretreated with RNase, and when assaying RNA the slide is pretreated with DNase. Results of the assay are confirmed by extracting gDNA or RNA and quantitating the relative amounts by qPCR or RT-qPCR, respectively.

Example 4 Multiplex Spatially Encoded Polynucleotide Abundance Assays

This example describes representative multiplex spatially encoded abundance assays for polynucleotide targets. One of skill in the art would appreciate that similar assays can be performed for protein targets, as well as other biological targets, according to the present disclosures.

A 57-Plex Assay Using Formalin-Fixed, Paraffin-Embedded (FFPE) Samples

A scheme using ligation of proximal probes followed by sequential ligation of a pair of spatial encoding adaptors (address tags) was used to form an amplifiable construct. For example, as shown in FIG. 15A, two target-specific probe oligos were ligated together following in situ hybridization. A unique adaptor or address tag encoding the X position was introduced via a microfluidic channel and ligated to the 5' end of the probes. A second address tag encoding the Y position was similarly installed at the 3' end of the probes. The address tags contained universal priming sites that allowed installation of additional sequencing adaptors via PCR. The final construct was a substrate for next-generation sequencing.

A 57-plex assay was performed using a pool of probes for 57 targets on commercially sourced FFPE sections of normal human liver and pancreas (Pantomics). The pool included probes for 18 liver specific targets, 19 pancreas specific targets, 4 housekeeping targets, 6 custom-generated negative controls sequences, and 10 pluripotency markers. All liver-specific probes were strongly enriched in liver and all but 3 of the pancreas-specific probes were strongly enriched in pancreas. These 3 probes had very few total counts so it is likely that they were sequences that hybridized or ligated inefficiently and thus were not reporting accurately. The results of this assay were consistent with published data for expression in normal liver and pancreas (BioGPS, available at biogps.org/#goto=welcome).

Figure 16:
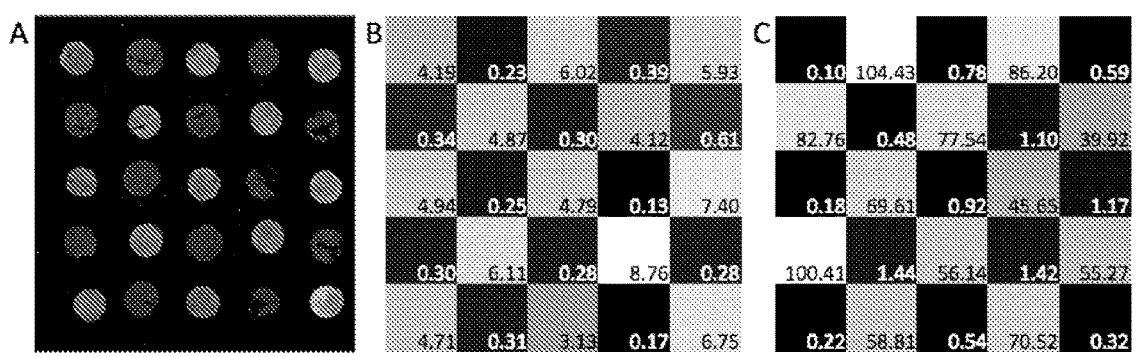
FIG. 16 provides an immunofluorescence image (FIG. 16A) and representative expression maps (FIG. 16B-C) generated according to some embodiments of the present disclosure.

A set of microfluidic devices with a 5-site×5-site layout was fabricated, to match a set of custom-designed tissue microarrays (TMAs) that contained a corresponding 5×5 checkerboard pattern was produced. The TMAs contained the same commercially sourced FFPE sections of normal human liver and pancreas (Pantomics) used above in this example, arranged in a checkerboard pattern. This known pattern of tissue spots on the array was used to verify the accuracy of the spatial encoding system. FIG. 16 shows an immunofluorescence image of a TMA as well as expression maps generated by the assay system using the microfluidic reagent delivery system. FIG. 16A shows immunofluorescence (IF) image of a custom TMA stained with two liver specific antibodies: PYGL, specific to hepatocytes and Annexin A2, specific to bile-duct cells. The reference was Protein Atlas, available at www.proteinatlas.org. The brightly stained spots are liver tissue and dim spots are pancreas. FIG. 16B shows a map of the sum of the 22 most abundant liver-specific genes by abundance, normalized to housekeeping genes (GAPDH and ActB). Each square corresponds to the signal mapped to one junction, a 500 µm×500 µm area centered on one of the tissue cores of the TMA. FIG. 16C shows a map of the sum of the 22 most abundant pancreas genes by abundance, normalized by housekeeping genes. The addressing channels of the microfluidic devices used are 500 µm wide at a 2 mm pitch with a depth of 50 µm, which corresponds to a "virtual-volume" of 12.5 nL that encompasses the intersection of the perpendicular channels.

These results demonstrate that mapped sequencing data using the multiplex system reproduced the expected expression pattern of the tissue sample, and that the multiplex assay is compatible with immunofluorescence imaging, allowing the determination of cell types based on protein markers and correlation with gene expression data.

A 134-Plex Assay Using Formalin-Fixed, Paraffin-Embedded (FFPE) Samples

A probe pool and two device layouts were developed. The probe pool consisted of 134 targets representing 69 unique genes shown in Table 1. When reading out expression by sequencing, a few highly expressed genes can account for the majority of the reads, limiting dynamic range of the assay. This issue was mitigated by attenuating some of the most highly expressed genes in the pool. This was accomplished by adding in attenuator probes in known ratios with the active probes. An attenuator probe lacks a 5' phosphate necessary for ligation, preventing production of an amplifiable product and thus decreasing the signal from that target. Table 2 shows the results of attenuation of the top 5 genes. Before attenuation they accounted for 73% of the reads whereas afterwards they accounted for less than 18%. This strategy can be used to achieve very high levels of multiplexing with current sequencing technology while still achieving high dynamic range.

TABLE 1

List of genes and number of unique targets per gene in 134-plex probe pool.

| | |
|---|---|
| Pluripotency | |
| AURKB | 3 |
| HMGB3 | 2 |
| JARID2 | 3 |
| LIN28A | 1 |
| SOX2 | 1 |
| Housekeeping | |
| ACTB | 2 |
| GAPDH | 2 |
| H2AFX | 2 |
| Controls | |
| 18S | 3 |
| Rand Neg | 3 |
| Other | |
| FXR1 | 2 |
| Liver | |
| AGXT | 2 |
| ALDO | 2 |
| APOB | 2 |
| BHMT | 2 |
| CPB2 | 2 |
| CYP2A6 | 2 |
| CYP2C8 | 2 |
| HPX | 2 |
| SAA4 | 2 |
| SERPIND1 | 2 |
| VTN | 2 |
| CA9 | 2 |
| EPB41L2 | 2 |
| HNF1B | 2 |
| KRT19 | 2 |
| KRT7 | 2 |

TABLE 1-continued

List of genes and number of unique targets per gene in 134-plex probe pool.

| | |
|---|---|
| MCAM | 2 |
| MYH9 | 2 |
| POGZ | 2 |
| SMARCA4 | 2 |
| ALB | 2 |
| ARG1 | 2 |
| CD14 | 2 |
| MBL2 | 2 |
| PYGL | 2 |
| SLC27A5 | 2 |
| STOM | 2 |
| Pancreas | |
| AQP8 | 2 |
| CARS | 2 |
| CEL | 2 |
| CLPS | 2 |
| CPA1 | 2 |
| GCG | 2 |
| INS | 1 |
| PNLIP | 2 |
| PNLIPRP2 | 2 |
| PPP4C | 2 |
| REG1B | 2 |
| SEL1L | 2 |
| CA12 | 2 |
| CPA2 | 2 |
| DPEP1 | 2 |
| GP2 | 2 |
| PRSS1 | 2 |
| SOX9 | 2 |
| WDR38 | 2 |
| ASB9 | 2 |
| CHGA | 2 |
| GAD2 | 2 |
| INSM1 | 2 |
| NCAM1 | 2 |
| PAX6 | 2 |
| PPY | 2 |
| SV2A | 2 |
| UCHL1 | 2 |

TABLE 2

Attenuation of top 5 assay targets

| Probe | Fraction of Reads | | Atten. |
|---|---|---|---|
| Name | w/o Atten. | w/Atten. | Factor |
| PNLIP_2 | 0.253 | 0.048 | 5.268 |
| PNLIP_1 | 0.203 | 0.035 | 5.871 |
| PRSS1_2 | 0.114 | 0.034 | 3.343 |
| CPA1_2 | 0.111 | 0.023 | 4.841 |
| CLPS_2 | 0.051 | 0.037 | 1.373 |
| Sum | 0.732 | 0.177 | |

Example 5 Elution and Preparation of Spatially Encoded Probes for Next Generation Sequencing Using the methods described supra, a 134-plex pool of probe pairs was hybridized to an FFPE sample, ligated and spatially encoded with X-positional and Y-positional adaptors. In preparation for elution, a hybridization chamber (Agilent) was applied to the slide and clamped in place to form a leakproof chamber containing the FFPE tissue sample. Using syringes, this chamber was filled with deionized water and the assembly was heated to 80° C. for 30 minutes after which time the eluate was removed using a syringe and transferred to a tube.

The spatially encoded constructs were purified by two rounds of positive selection using magnetic beads to isolate them from any un-encoded probes, leftover positional-encoding adaptors, or malformed constructs. In the first round of purification, the eluate was hybridized to a biotinylated capture probe comprising a sequence that was complementary to a sequence spanning the junction of the X positional adaptor (address tag) and the 5' end of the joined probe pair. This capture probe was then captured on streptavidin functionalized magnetic beads, which were then washed extensively to remove unbound material. Constructs hybridized to capture probes were then eluted by heating in an elution buffer containing a blocking oligonucleotide that was complementary to the capture probe. The eluate was separated from the magnetic beads using a magnet, transferred to a new container, and hybridized with a biotinylated capture probe comprising a sequence that was complementary to a sequence spanning the junction of the 3' end of the joined probe pair and the Y positional adaptor (address tag). This capture probe, together with hybridized constructs, was subsequently captured on streptavidin functionalized magnetic beads and washed.

The beads were transferred directly into a PCR mix that included primers comprising sequences that enable sequencing of the PCR products on an Illumina MiSeq instrument. The primers also comprised TruSeq barcodes to allow demultiplexing of multiple samples in a single sequencing run. A fraction of the PCR product was analyzed by gel electrophoresis to verify the presence of the amplified spatially encoded constructs. The remaining product was purified using a Qiagen PCR purification Kit. Finally, the spatially encoded constructs were purified by size selection using either a conventional gel electrophoresis device or the Pippen Prep System (Sage Science).

The purified encoded construct was sequenced using an Illumina MiSeq instrument and the data were used to generate expression maps.

Example 6 Spatially Encoded Protein In Situ Assays

This example describes a spatially encoded protein in situ assay. A highly multiplexable protein detection assay was carried out on a tissue microarray like the ones described supra containing a checkerboard pattern of liver and pancreas tissue cores. In this case a two-plex assay was encoded using a 5-site×5-site addressing scheme. The assay was performed by first applying a typical immunostaining procedure with two different primary antibodies, one specific to exocrine cells in the pancreas and one specific to hepatocytes in the liver. Two antibody-DNA conjugates were used as secondary antibodies and were applied to the entire tissue microarray. The conjugates included an oligonucleotide comprising an identity tag as well as an upstream and downstream splint region to allow ligation of X and Y address tags. After applying the primary antibody and secondary antibody conjugate to the entire sample and washing sufficiently, a pair of microfluidic channel devices was used to deliver sequentially the X and Y address tags, which were ligated to the oligonucleotide on the conjugate. The conjugates were eluted from the sample and the combined X and Y tags plus the intervening identity tag formed an amplifiable construct which was amplified, purified and subjected to next generation sequencing to identify the abundance of the antibody targets at each spatially encoded location.

Example 7 Spatially Encoded Protein In Situ Assays

This example describes a spatially encoded protein in situ assay. As shown in FIG. 6A, a highly multiplexable protein detection assay can be carried out on a sample that preserves the spatial organization of cells in a tissue, e.g., a paraffin-embedded or fresh-frozen tissue section fixed to a glass slide. Assay reagents are protein binders (e.g. antibodies) that are identified via linked DNA tags that can be further encoded with tag sequences that encode positional or address information (in this example, indicated as "X" dimension and "Y" dimension). The address tags X and Y are flanked by universal sequences (UP1 and UP2) that can be used as PCR priming sites, adaptors for next-generation sequencing, or both.

As shown in FIG. 6B, the binders, for example, the DNA-labeled antibody probes in this example, are delivered over the entire sample surface in a bulk process. The X and Y address tags are then delivered to the sample and coupled to the probes, so that the probes are encoded by the X and Y address tags in a spatially defined pattern. In this example, two sets of tags (i.e., a set of 10 X address tags, namely X1, X2, X3, . . . , X10, and a set of 10 Y address tags, namely Y1, Y2, Y3, . . . , Y10) are used in a combinatorial fashion, and 100 sites in the sample can be uniquely identified by the combinations of X and Y address tags. For example, a site in the sample shown in Figure XB is uniquely identified as (X9, Y1).

Once the in situ assay is completed, the assay products are eluted and sequenced. The address tag sequence information identifies the site at which the assay is performed, and the probe sequence information identifies the protein that is targeted. The frequency of a particular assay product in the digital readout can be used to infer the relative abundance of its target sequence in the sample. This information can then be associated with other information, including conventional histological information, and/or transcript abundance obtained via the related spatially encoded genomic assay.

Figure 17:
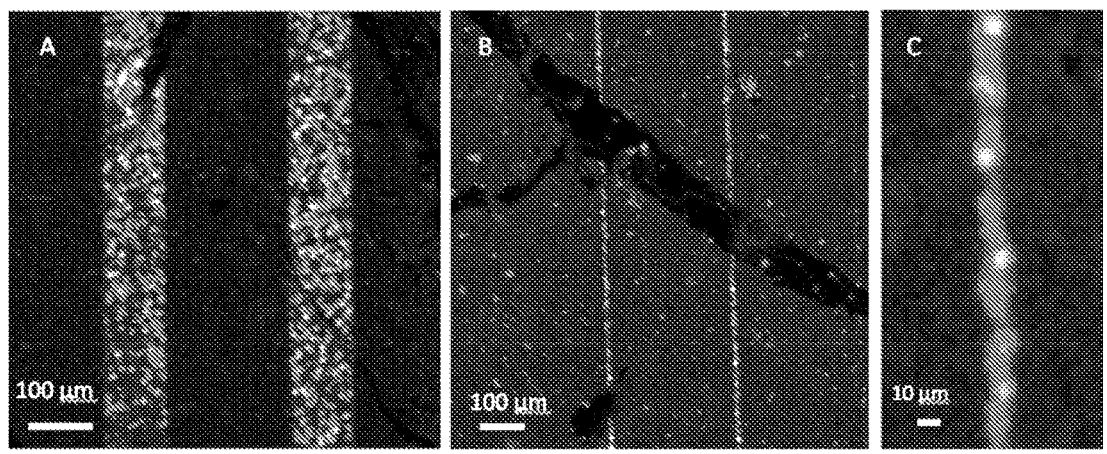
FIG. 17 illustrates fluorescence images of a sample addressed with microfluidic devices with different channel width, according to some embodiments of the present disclosure.

Example 8 Microfluidic Device Layouts with Decreased Size and Increased Number of Sites Four different pairs of microfluidic addressing devices were fabricated, each with a different layout. Each pair of devices comprised and X-axis device and a Y-axis device, each device in the pair having an equal number of parallel channels with the same size and pitch. The first pair had sixteen 100 µm wide channels at 300 µm pitch per device. The second device design had sixteen 10 µm wide channels at 300 µm pitch. The third design had twelve 50 µm wide channels at 100 µm pitch and the fourth had sixteen 25 µm channels at 50 µm pitch. The first two designs were tested on tissue sections by using fluorescent probes to visualize the area addressed by the addressing channels. It was found that channel width provided an accurate measure of the addressed area. FIG. 17 shows fluorescence image of FFPE sample after addressing with 100 µm wide channels using fluorescent-labeled spatial encoding oligo (FIG. 17A), and fluorescence image of FFPE sample after addressing with 10 µm wide channels using fluorescent-labeled spatial encoding oligo (FIG. 17B-C). The 10 µm channel device samples an area of ~100 µm$^2$, on the order of the area of a single cell. In both cases, the width of the addressed area matches the physical width of the addressing channel. These results suggest that in this case, diffusion did not cause the effective addressing width to be much larger than the physical channels, and that the technique may be able to address areas smaller than a single cell.

Figure 18:
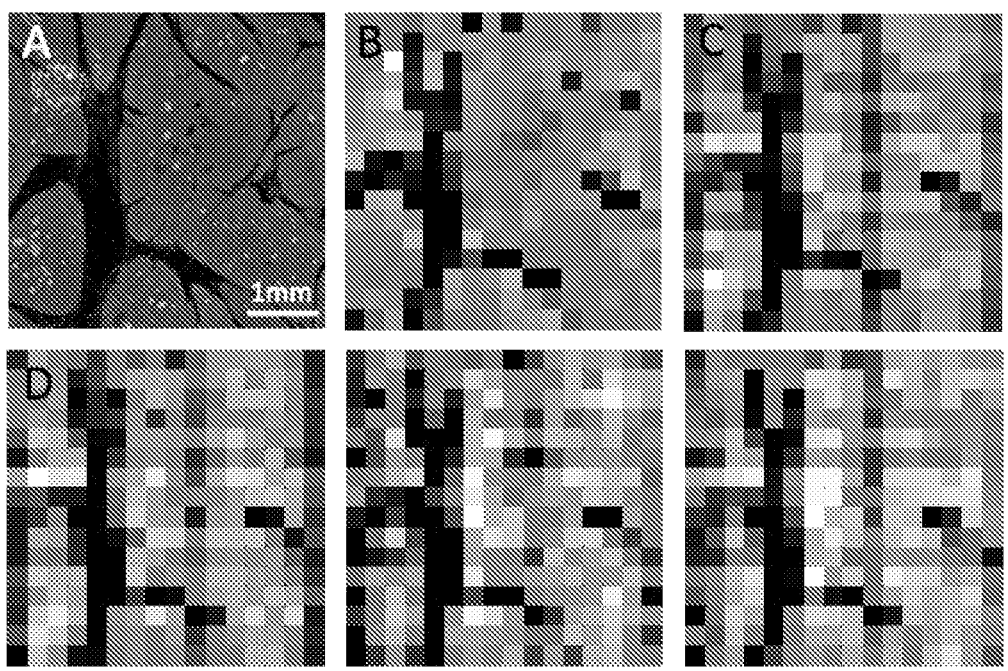
FIG. 18 illustrates a fluorescence image and expression maps of targets in a sample, according to some embodiments of the present disclosure.

Each of the device pairs was also used to assay a pancreas sample. Gene expression maps generated for the FFPE tissue sample were correlated with immunofluorescence (IF) data. FIG. 18 shows maps generated using the first device design. FIG. 18A shows the IF image stained with CARS, FIG. 18B shows IF intensity sampled at each microfluidic junction and plotted as an expression map, FIG. 18C shows expression map of sum of all targets, and FIG. 18D shows expression maps of three individual targets. When the IF data was sampled at the location of each microfluidic junction and plotted as an expression map, the major features (lobes and voids) of the tissue were recognizable even at the low resolution. These features were reproduced in the gene expression map when all genes are summed and even for individual genes, although the images became somewhat noisy.

Figure 19:
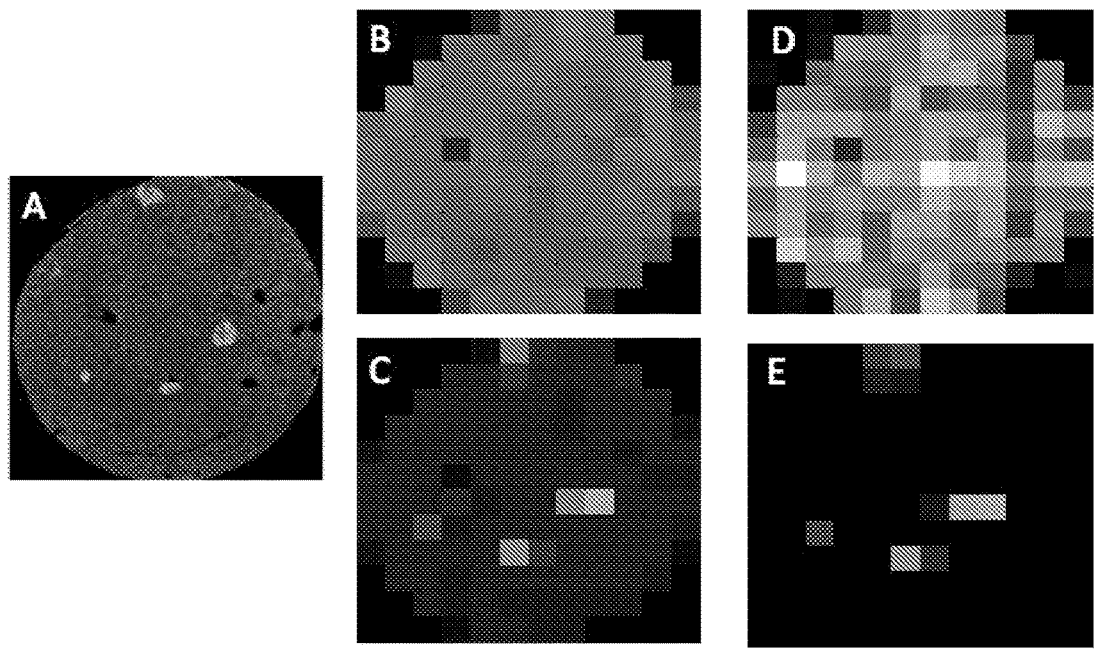
FIG. 19 illustrates a fluorescence image and expression maps of targets in a sample, according to some embodiments of the present disclosure.

A similar experiment was performed using the third device design. Anti-CARS and Anti-Insulin antibodies were used to stain a pancreas section and identify Islets of Langerhans within the sample. Islets are identifiable as the four small bright "dots" in FIG. 19A. The islets were sparsely distributed throughout the tissue and were roughly the size of one or two channel junctions. FIG. 19B shows a protein expression map of CARS, and FIG. 19C shows a protein expression map of Insulin. Gene expression maps were also generated for the sum of all genes (FIG. 19D) assayed as well as for Insulin (FIG. 19E showing Insulin mRNA levels). The sum of all genes reproduces the overall shape of the tissue core (large circle) while the insulin expression map identifies each of the islets present in the protein expression map, providing a correlation between gene and protein expression.

Example 9 A Method to Reduce Background and Increase Signal-to-Noise Ratio

This example describes a method of detecting rare variant sequences in a mixed population of nucleic acids. The method can be integrated into the methods and assay systems disclosed herein, for example, to reduce the background contributed by random errors and thus to increase the signal to noise ratio (S/N).

Parallel clonal amplification methods in combination with digital sequencing have permitted large-scale analysis of variation at resolutions in the range of 1% (Druley et al., 2009, Nat. Methods 6: 263-65), but not much below. Although next-generation sequencing enables de novo discovery and holds great promise for deep analysis of variation across the genome, a combination of factors at various steps in the sequencing process have made it difficult to obtain very low error rates at readout. These factors include cross-talk between detection channels, incomplete reactions leading to signal loss, increased background as a result of loss in synchronicity of nucleotide addition, and noise and errors in image processing and signal extraction, which worsen significantly at higher sequencing densities. Thus the sequencing readout error rate is far above intrinsic rates exhibited by the high fidelity polymerases used in sequencing reactions. For example, an error rate of $4.4 \times 10^{-7}$ is estimated for Pfusion™ polymerase (New England Biolabs, Ipswich, Mass.).

The method described in this example addresses the above technical issues, by using tags to identify target sequences that are "identical by descent." As illustrated in FIG. 20A, sequence reads can be partitioned into related groups on this basis.

FIG. 20A shows the concept of the rare variant assay, and FIG. 20B provides exemplary configurations of probes that can be used to integrate the rare variant assay in the spatially encoded assays of the present disclosure. The top panel of FIG. 20A shows a target sequence of interest flanked by adaptors that contain Illumina adaptor sequences for surface PCR (labeled a and b). The target can be obtained from a variety of sources, for example, a PCR amplicon. The adaptors contain a variable tag region (labeled z). Both strands are shown to illustrate that the Illumina adaptors are asymmetric. The tagged adaptors are used to construct libraries for sequencing. Single molecules are amplified to form "clusters" on the surface of a flowcell. Sequences are determined for each target region and its associated tag regions. In the final step shown, reads are grouped according to their tag regions, based on the assumption that reads with the same tag sequences are identical by descent, given that z is sufficiently long. The groupings are then analyzed to identify rare variant sequences (e.g. targets in the last set numbered 4 are shown in darker color compared to those in sets 1-3 to indicate that the target sequence differs from those in sets 1-3). Similar methods for rare variant sequence detection have been described in Fu et al., 2011, Proc. Natl. Acad. Sci., 108: 9026-9031, and in Schmitt et al., 2012, Proc. Natl. Acad. Sci., 109: 14508-14513, the disclosures of which are incorporated by reference herein for all purposes.

With this strategy, the contribution of random sequencing errors can be virtually eliminated. Therefore, barring contamination, the ability to detect a rare variant will be limited in theory by the sample size.

Note that although the design shown in FIG. 20A references the Illumina adaptors and surface amplification methodology, the method is general and can be used with other sequencing platforms such as the SOLiD platform (Life Technologies), the 454 platform (Roche), and the Pacific Biosciences and Ion Torrent library constructions methods.

A model system was established to quantitate the improvements in the limit of detection over standard sequencing with the Illumina GAIIx instrument. The model system consisted of a wild-type 100-mer oligo and a mutant sequence containing a unique, single point mutation in the wild-type sequence. Synthetic oligos were cloned into an *E. coli* plasmid vector and individual clones were picked and sequence verified in order to obtain constructs that contained the desired sequences, providing pure, well defined sequence constructs free from oligonucleotide chemical synthesis errors (typically in the range of 0.3-1%). The 100-mer of interest was then excised from the plasmid clone by restriction digestion. Mutant and wild-type oligos were quantitated and mixed at ratios of 1:0, 1:20, 1:1000, 1:10,000, 1:100,000 and 1:1,000,000, and 0:1 to simulate the presence of a rare variant in a wild-type DNA background.

Next, custom adaptors containing random 10-mer tags were designed and synthesized. Libraries were prepared from the defined oligo mixtures, and sequenced on an Illumina GAIIx instrument according to the constructs and steps outlined in FIG. 20A. The data were first analyzed without utilizing the tag information (tag z as shown in FIG. 20A). This resulted in detection of the point mutation only in the 1:20 sample. A second round of analysis utilizing the tags was done using only high quality reads in which tag1/tag2 pairs were retained if the tags were grouped with each other >99% of the time and had >2 replicates. In order for a tag group to be scored as a mutation, at least 90% of reads in the group had to agree.

The mutant allele was also successfully detected in the 1:10,000, 1:100,000, and 1:1,000,000 samples as shown in Table 3. Mutant allele frequencies within a factor of 2 of the expected value were observed, and this difference was accounted for in dilution and pipetting error. The power to observe a mutation in the wild-type (negative control) sample with ~7.5 M tag groups is greater than 0.999. Therefore, the difference between the 1:1,000,000 spiked sample and the negative control was highly significant.

TABLE 3

Demonstration of ability to detect a mutant allele over~6 orders of magnitude

| Mutant:WT | Number of Tag Groups Assayed | Number of Mutant Alleles Observed | Estimated Allele Frequency |
|---|---|---|---|
| 1:20 | 3,433 | 273 | 0.08 |
| 1:1,000 | 2,539 | 6 | 0.0024 |
| 1:10,000 | 157,431 | 26 | 1.65E-04 |
| 1:100,000 | 1,752,922 | 33 | 1.88E-05 |
| 1:1,000,000 | 4,186,545 | 5 | 1.19E-06 |
| (Negative Ctrl) 1:0 | 7,488,853 | 0 | 0 |

The power to observe a mutant with frequency f is $1-(1-f)^{\#tags}$, so additional sequencing depth can increase the detection power. The limit of detection in this model system is determined only by sample size and any background contamination that might be present.

This method can be used to distinguish in vitro amplification errors from rare variants present in the original sample. For example, a simple threshold that the mutation frequency within a tag group must be >0.9 can be used to exclude PCR amplification errors from the analysis. This is based on the observation that the expected fraction of copies containing an error at that particular location equals 0.5, conditional on the error occurring in the very first cycle and neglecting the chance of consecutive PCR errors at the same position. No tags in the negative control pass this criterion.

This method can be integrated into the methods and assay systems for determining a spatial pattern of a target abundance, expression, or activity, in order to reduce the background contributed by random errors and thus to increase the signal to noise ratio (S/N). Non-limiting exemplary configurations of probes that integrate the X and Y address tags and the variable tag region z are shown in FIG. 20B.

Example 10 Analysis of Brain Tissue

This example describes production of an at least 24-plex protein assay panel and confirmation of its tissue/cell-type specificity by correlation with fluorescent labeling and by analysis of tissue microarrays.

A set of 26 antigens is selected. These antigens are expressed in neurons, astrocytes, oligodendrocytes, microglia or proliferating cells, and antibodies that have been raised against the antigens are commercially available (Table 4). These antibodies have been successfully used, in conjunction with well-established staining techniques, to mark different cell types and regions within brain sections (Lyck, et al., 2008, J Histochem Cytochem 56, 201-21). For the purposes of the assay it is necessary to avoid procedures for antibody binding that damage RNA.

Antigen accessibility is addressed by exploring systematically a range of "antigen retrieval" protocols and testing their compatibility with RNA. See, MacIntyre, 2001, Br J Biomed Sci. 58, 190-6; Kap et al., 2011, PLoS One 6, e27704; Inoue and Wittbrodt, 2011, PLoS One 6, e19713. A panel of antibody assays rather than any individual assay are explored to identify a suitable subset for use in a multiplexed panel.

The assay system is also validated by using spatially-encoded and conventional IHC fluorescence data and spatially encoded RNA data, applied to brain tissue. High-dimensional protein and mRNA data from 32×32 sites in sections of human brain tissue are generated and compared with published data and brain atlas data.

The Allen Brain Atlas (www.brain-map.org) can be used to select target genes for production of a panel of gene expression assays with high information content, using the methods and assay systems of the present disclosure. The "Differential Search" tool is used to interrogate the rich spatial expression dataset (generated by in situ hybridization), it is identified that ~200 genes are present at a range of abundances in at least one structure/compartment of the brain, and/or are strongly differentially expressed between the different structures/compartments. The selection is reviewed to incorporate any new information or criteria. Probes against the set of ~200 mRNAs are designed and tested for their performance in the multiplexed assay, using the online gene expression data as a reference.

Protein panels and RNA assay panels are applied simultaneously to analyze sections of normal human brain. For example, the abundance of at least 24 proteins and 192 mRNA analytes over a 32×32 grid of 50 μm pixels from sections of healthy human brain is analyzed. The results are used to generate a rich map of the brain's spatially-organized molecular terrain, and are amenable to analysis in various ways, including those that reveal:

1. The organization of brain into distinct sub-structures: both at the anatomical scale, and at the lower-level multi-cellular level;
2. Spatial variation in the representation of different cell types across the tissue (e.g. using sets of proteins/mRNAs known to be specific to particular cell types); and
3. The relation between mRNA and protein expression from the same gene at different tissue locations.

TABLE 4

Candidate proteins to differentiate brain tissues, which have been used in immunohistochemistry and have commercially available antibodies.

| Protein | Observed Specificity {Lyck, 2008} |
|---|---|
| b-tubulin III | Neuropil and neuronal bodies |
| CD11b | None |
| CD14 | Perivascular macrophages |
| CD34 | Endothelium and white blood cells |
| CD39 | Endothelium, astroglia, and macrophages |
| CD45 | Microglia, macrophages, and lymphocytes |
| CD68 | Microglia and macrophages |
| CD169 | Endothelial and perivascular macrophages |
| CNPase | Myelinated fibers and round cell bodies |
| GFAP | Astroglia in white matter and neocortex |
| HLA-DR | Microglia/macrophages and lymphocytes |
| Ki-67 | Perivascular space and sub-ventricular zone |
| MAP-2 | Neurons and proximal part of apical dendrites |
| MBP | Myelinated fibers |
| Nestin | Endothelial cells/vessel wall |
| NeuN | Neuronal cell bodies |
| Neurofilament | Neuronal cell processes |
| NG2 | None |

TABLE 4-continued

Candidate proteins to differentiate brain tissues, which have been used in immunohistochemistry and have commercially available antibodies.

| Protein | Observed Specificity {Lyck, 2008} |
|---|---|
| Nkx-2.2 | None |
| NSE | Neuropil |
| O4 sulfatide | Myelinated fibers |
| PDGFa-R | None |
| p25a | Neuropil and round cell bodies |
| S100b | Astroglia in white matter and neocortex |
| TOAD-64 | Neuropil |
| Vimentin | Astroglia and endothelial cells/vessel wall |

All headings are for the convenience of the reader and should not be used to limit the meaning of the text that follows the heading, unless so specified.

Citation of the above publications or documents is not intended as an admission that any of them is pertinent prior art, nor does it constitute any admission as to the contents or date of these publications or documents.

While various embodiments of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can, be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

We claim:

1. A method of determining a spatial pattern of abundance, expression and/or activity of a biological target in a sample, comprising:
   (a) delivering a probe for the biological target to the sample, the probe comprising a binding moiety capable of binding to the biological target, wherein the probe comprises an identity tag that identifies the biological target or target-binding moiety;
   (b) affixing the sample from step (a) to a first microfluidic device to form multiple first addressing channels between the sample and the first microfluidic device, wherein each first addressing channel identifies a first area in the sample;
   (c) delivering a first address tag through each of the first addressing channels to each first area in the sample, wherein each first address tag is to be coupled to the probe;
   (d) affixing the sample from step (c) to a second microfluidic device to form multiple second addressing channels between the sample and the second microfluidic device, wherein each second addressing channel identifies in the sample a second area that intersects with the first area at an angle greater than 0 degree;
   (e) delivering a second address tag through each of the second addressing channels to each second area in the sample, wherein each second address tag is to be coupled to the probe, whereby the first address tag and the second address tag at each intersection determine the intersection's address;
   (f) analyzing the probe bound to the biological target, the analysis comprising: (1) determining the abundance, expression and/or activity of the biological target by assessing the amount of the probe bound to the biological target; and (2) determining the identities of the identity tag and the first and second address tags at each address; and
   (g) determining the spatial pattern of the biological target abundance, expression and/or activity in the sample based on the analysis of step (f).

2. The method of claim 1, wherein the angle is about 90 degrees, about 80 degrees, about 70 degrees, about 60 degrees, about 50 degrees, about 40 degrees, about 30 degrees, about 20 degrees, or about 10 degrees.

3. The method of claim 1, wherein the multiple first addressing channels substantially parallel each other and the multiple second addressing channels substantially parallel each other.

4. The method of claim 1, wherein the sample is a biological sample selected from the group consisting of a freshly isolated sample, a fixed sample, a frozen sample, an embedded sample, a processed sample, or a combination thereof.

5. The method of claim 1, wherein the first addressing channels are disposed on the same device as the second addressing channels.

6. The method of claim 1, wherein the first addressing channels are disposed on a separate device from the second addressing channels.

7. The method of claim 1, wherein the first and/or second microfluidic device is manufactured by soft-lithographic techniques.

8. The method of claim 1, wherein the number of the first and/or second addressing channels is n, n being an integer between 100 and 150, between 150 and 200, between 200 and 250, between 250 and 300, between 300 and 350, between 350 and 400, between 400 and 450, between 450 and 500, between 500 and 550, between 550 and 600, between 600 and 650, between 650 and 700, between 700 and 750, between 750 and 800, between 800 and 850, between 850 and 900, between 900 and 950, between 950 and 1000, or greater than 1000.

9. The method of claim 1, wherein the width of the first and/or second addressing channels is about 5 µm, about 10 µm, about 50 µm, about 100 µm, about 150 µm, about 200 µm, about 250 µm, about 300 µm, about 350 µm, about 400 µm, about 450 µm, or about 500 µm.

10. The method of claim 1, wherein the depth of the first and/or second addressing channels is about 5 µm, about 10 µm, about 50 µm, about 100 µm, about 150 µm, about 200 µm, about 250 µm, about 300 µm, about 350 µm, about 400 µm, about 450 µm, or about 500 µm.

11. The method of claim 1, wherein the distance between each first addressing channel and/or between each second addressing channel is about 5 µm, about 10 µm, about 50 µm, about 100 µm, about 150 µm, about 200 µm, about 250 µm, about 300 µm, about 350 µm, about 400 µm, about 450 µm, about 500 µm, about 550 µm, about 600 µm, about 650 µm, about 700 µm, about 750 µm, about 800 µm, about 850 µm, about 900 μm, about 950 μm, about 1.0 mm, about 1.2 mm, about 1.3 mm, about 1.4 mm, about 1.5 mm, about 1.6 mm, about 1.7 mm, about 1.8 mm, about 1.9 mm, or about 2.0 mm.

12. The method of claim 1, wherein the first and/or second address tag comprises an oligonucleotide.

13. The method of claim 1, wherein the identity tag comprises an oligonucleotide.

14. The method of claim 1, wherein the biological target is a nucleic acid and the probe for the biological target comprises an oligonucleotide.

15. The method of claim 1, wherein the biological target is a nucleic acid and two probes for the nucleic acid target are used.

16. The method of claim 1, wherein the biological target is a protein, and the probe for the target protein comprises an oligonucleotide and a target-binding moiety, which is a protein.

17. The method of claim 1, wherein the biological target comprises an enzyme.

18. The method of claim 1, wherein the binding moiety of the probe for the biological target comprises an antibody, an aptamer, or a small molecule.

19. The method of claim 1, wherein the analyzing step is performed by nucleic acid sequencing or high-throughput sequencing.

20. The method of claim 1, wherein spatial patterns of the abundance, expression and/or activity of multiple biological targets in the sample are determined in parallel.

21. The method of claim 1, wherein the number of biological targets being assayed is x and the number of the multiple sites being assayed in the sample is y, and the value of x×y is greater than 20, 50, 75, 100, 1,000, 10,000, 100,000, or 1,000,000.

22. The method of claim 1, wherein at least one hundred thousand, at least five hundred thousand, or at least one million probes bound to the biological target are analyzed in parallel.

23. The method of claim 1, wherein software programmed hardware performs at least two steps of the delivering steps, the affixing steps, the analyzing step and the determining step.

24. The method of claim 1, wherein a known percentage of the probe for the biological target is an attenuator probe.

25. The method of claim 24, wherein the attenuator probe prevents production of an amplifiable product.

26. The method of claim 24, wherein the attenuator probe lacks a 5' phosphate.

27. The method of claim 1, wherein the address tag is coupled to the probe for the biological target by ligation, by extension, by extension followed by ligation, or any combination thereof.

28. The method of claim 1, wherein:
step (a) comprises delivering to the sample an adaptor that specifically binds to the probe, and the adaptor comprises the identity tag that identifies the biological target or target-binding moiety,
step (c) comprises delivering the first address tag through each of the first addressing channels to each first area in the sample, wherein each first address tag is to be coupled to the adaptor,
step (e) comprises delivering the second address tag through each of the second addressing channels to each second area in the sample, wherein each second address tag is to be coupled to the adaptor, whereby the first address tag and the second address tag at each intersection determine the intersection's address, and (f) analyzing the adaptor bound to the biological target, the analysis comprising: (1) determining the abundance, expression and/or activity of the biological target by assessing the amount of the adaptor bound to the biological target; and (2) determining the identities of the identity tag and the first and second address tags at each address.

29. A method of determining a spatial pattern of abundance, expression and/or activity of a biological target in a sample, comprising:
(a) affixing the sample to a first microfluidic device to form multiple first addressing channels between the sample and the first microfluidic device, wherein each first addressing channel identifies a first area in the sample;
(b) delivering a first probe for the biological target through each of the first addressing channels to each first area in the sample, the probe comprising: (1) a first binding moiety capable of binding to the biological target; (2) a first address tag that identifies an area in the sample to which the first probe is delivered; and (3) a first identity tag that identifies the biological target or the first binding moiety;
(c) affixing the sample from step (b) to a second microfluidic device to form multiple second addressing channels between the sample and the second microfluidic device, wherein each second addressing channel identifies in the sample a second area that intersects with the first area at an angle greater than 0 degree;
(d) delivering a second probe for the biological target through each of the second addressing channels to each second area in the sample, the probe comprising: (1) a second binding moiety capable of binding to the biological target; (2) a second address tag that identifies an area in the sample to which the first probe is delivered; and (3) a second identity tag that identifies the biological target or the second binding moiety, whereby the first address tag and the second address tag at each intersection determine the intersection's address;
(e) analyzing the probes bound to the biological target, the analysis comprising: (1) determining the abundance, expression and/or activity of the biological target by assessing the amount of the probes bound to the biological target; and (2) determining the identities of the first and second identity tags and the first and second address tags at each address; and
(f) determining the spatial pattern of the biological target abundance, expression and/or activity in the sample based on the analysis of step (e).

30. A method of determining a spatial pattern of abundance, expression and/or activity of a biological target in a sample, comprising:
(a) affixing the sample to a first microfluidic device to form multiple first addressing channels between the sample and the first microfluidic device, wherein each first addressing channel identifies a first area in the sample;
(b) delivering a probe for the biological target through each of the first addressing channels to each first area in the sample, the probe comprising a binding moiety capable of binding to the biological target, wherein the probe comprises: (1) a first address tag that identifies an area in the sample to which the probe is delivered; and (2) an identity tag that identifies the biological target or the binding moiety;
(c) affixing the sample from step (b) to a second microfluidic device to form multiple second addressing channels between the sample and the second microfluidic device, wherein each second addressing channel identifies in the sample a second area that intersects with the first area at an angle greater than 0 degree;
(d) delivering a second address tag through each of the second addressing channels to each second area in the sample, wherein each second address tag is to be coupled to the probe, whereby the first address tag and the second address tag at each intersection determine the intersection's address;
(e) analyzing the probe bound to the biological target, the analysis comprising: (1) determining the abundance, expression and/or activity of the biological target by assessing the amount of the probe bound to the biological target; and (2) determining the identities of the identity tag and the first and second address tags at each address; and
(f) determining the spatial pattern of the biological target abundance, expression and/or activity in the sample based on the analysis of step (e).

31. The method of claim 30, wherein:
step (b) comprises delivering an adaptor that specifically binds to the probe, wherein the adaptor comprises: (1) the first address tag that identifies the area in the sample to which the adaptor is delivered; and (2) the identity tag that identifies the biological target or the binding moiety,
step (d) comprises delivering the second address tag through each of the second addressing channels to each second area in the sample, wherein each second address tag is to be coupled to the adaptor, whereby the first address tag and the second address tag at each intersection determine the intersection's address,
step (e) comprises analyzing the adaptor bound to the biological target, the analysis comprising: (1) determining the abundance, expression and/or activity of the biological target by assessing the amount of the adaptor bound to the biological target; and (2) determining the identities of the identity tag and the first and second address tags at each address.

32. A method of address coding multiple sites in a sample, comprising:
(a) providing the sample affixed to a first microfluidic device to form multiple first addressing channels between the sample and the first microfluidic device, wherein each first addressing channel identifies a first area in the sample;
(b) delivering a first probe capable of binding to a target in the sample through each of the first addressing channels to each first area in the sample;
(c) affixing the sample from step (b) to a second microfluidic device to form multiple second addressing channels between the sample and the second microfluidic device, wherein each second addressing channel identifies in the sample a second area that intersects with the first area at an angle greater than 0 degree;
(d) delivering a second probe capable of binding to the target in the sample through each of the second addressing channels to each second area in the sample; and
(e) determining an address of each intersection based on the first probe and the second probe bound to the target at the intersection.

33. The method of claim 32, wherein the angle is about 90 degrees, about 80 degrees, about 70 degrees, about 60 degrees, about 50 degrees, about 40 degrees, about 30 degrees, about 20 degrees, or about 10 degrees.

34. The method of claim 32, wherein the first addressing channels substantially parallel each other and the second addressing channels substantially parallel each other.

35. The method of claim 32, wherein the sample is a biological sample selected from the group consisting of a freshly isolated sample, a fixed sample, a frozen sample, an embedded sample, a processed sample, or a combination thereof.

36. The method of claim 32, wherein the first addressing channels are disposed on the same device as the second addressing channels.

37. The method of claim 32, wherein the first addressing channels are disposed on a separate device from the second addressing channels.

38. The method of claim 32, wherein the first or second microfluidic device is manufactured by soft-lithographic techniques.

39. The method of claim 32, wherein the number of the first or second addressing channels is n, n being an integer between 100 and 150, between 150 and 200, between 200 and 250, between 250 and 300, between 300 and 350, between 350 and 400, between 400 and 450, between 450 and 500, between 500 and 550, between 550 and 600, between 600 and 650, between 650 and 700, between 700 and 750, between 750 and 800, between 800 and 850, between 850 and 900, between 900 and 950, between 950 and 1000, or greater than 1000.

40. The method of claim 32, wherein the width of the first or second addressing channels is about 5 µm, about 10 µm, about 50 µm, about 100 µm, about 150 µm, about 200 µm, about 250 µm, about 300 µm, about 350 µm, about 400 µm, about 450 µm, or about 500 µm.

41. The method of claim 32, wherein the depth of the first or second addressing channels is about 5 µm, about 10 µm, about 50 µm, about 100 µm, about 150 µm, about 200 µm, about 250 µm, about 300 µm, about 350 µm, about 400 µm, about 450 µm, or about 500 µm.

42. The method of claim 32, wherein the distance between each first addressing channel or between each second addressing channel is about 5 µm, about 10 µm, about 50 µm, about 100 µm, about 150 µm, about 200 µm, about 250 µm, about 300 µm, about 350 µm, about 400 µm, about 450 µm, about 500 µm, about 550 µm, about 600 µm, about 650 µm, about 700 µm, about 750 µm, about 800 µm, about 850 µm, about 900 µm, about 950 µm, about 1.0 mm, about 1.2 mm, about 1.3 mm, about 1.4 mm, about 1.5 mm, about 1.6 mm, about 1.7 mm, about 1.8 mm, about 1.9 mm, or about 2.0 mm.

43. The method of claim 32, wherein the first probes are different from each other, and the second probes are different from each other and different from the first probes.

* * * * *